US006875751B2

(12) United States Patent
Imbach et al.

(10) Patent No.: US 6,875,751 B2
(45) Date of Patent: Apr. 5, 2005

(54) 3'-PRODRUGS OF 2'-DEOXY-β-L-NUCLEOSIDES

(75) Inventors: Jean-Louis Imbach, Montpellier (FR); Martin L. Bryant, Carlisle, MA (US); Gilles Gosselin, Montpellier (FR)

(73) Assignees: Idenix Pharmaceuticals, Inc., Cambridge, MA (US); CNRS, Paris (FR); L'Universite Montpellier II, Montpellier (FR)

( * ) Notice: Subject to any disclaimer, the term of this patent is extended or adjusted under 35 U.S.C. 154(b) by 187 days.

(21) Appl. No.: 09/883,033

(22) Filed: Jun. 15, 2001

(65) Prior Publication Data

US 2003/0083306 A1 May 1, 2003

Related U.S. Application Data
(60) Provisional application No. 60/212,100, filed on Jun. 15, 2000.

(51) Int. Cl.⁷ .............................................. A61K 31/70

(52) U.S. Cl. ........................... 514/49; 514/42; 536/28.5

(58) Field of Search ........................... 536/28.5; 514/49, 514/42

(56) References Cited

U.S. PATENT DOCUMENTS

| | | | |
|---|---|---|---|
| 4,916,122 A | | 4/1990 | Chu |
| 4,957,924 A | | 9/1990 | Beauchamp |
| 5,149,794 A | | 9/1992 | Yatvin et al. |
| 5,190,926 A | | 3/1993 | Chu |
| 5,194,654 A | | 3/1993 | Hostetler et al. |
| 5,223,263 A | | 6/1993 | Hostetler et al. |
| 5,256,641 A | | 10/1993 | Yatvin et al. |
| 5,411,947 A | | 5/1995 | Hostetler et al. |
| 5,416,203 A | * | 5/1995 | Letsinger ................ 536/25.34 |
| 5,463,092 A | | 10/1995 | Hostetler et al. |
| 5,470,838 A | | 11/1995 | von Borstel et al. |
| 5,539,116 A | | 7/1996 | Liotta |
| 5,543,389 A | | 8/1996 | Yatvin et al. |
| 5,543,390 A | | 8/1996 | Yatvin et al. |
| 5,543,391 A | | 8/1996 | Yatvin et al. |
| 5,554,728 A | | 9/1996 | Basava et al. |
| 5,559,101 A | * | 9/1996 | Weis et al. .................... 514/45 |
| 5,565,438 A | * | 10/1996 | Chu et al. ..................... 514/50 |
| 5,567,688 A | | 10/1996 | Chu |
| 5,587,362 A | * | 12/1996 | Chu et al. ..................... 514/46 |
| 5,703,058 A | | 12/1997 | Schinazi et al. |
| 5,736,531 A | | 4/1998 | von Borstel et al. |
| 5,939,402 A | | 8/1999 | Weis et al. |
| 5,968,914 A | | 10/1999 | von Borstel et al. |
| 6,020,322 A | | 2/2000 | von Borstel et al. |
| 6,025,335 A | | 2/2000 | Weis et al. |
| 6,194,391 B1 | | 2/2001 | Schinazi et al. |
| 6,245,749 B1 | | 6/2001 | Schinazi et al. |
| 6,258,795 B1 | | 7/2001 | von Borstel et al. |
| 6,297,222 B1 | | 10/2001 | von Borstel et al. |

FOREIGN PATENT DOCUMENTS

| | | |
|---|---|---|
| EP | 0 352 248 | 1/1990 |
| EP | 0 350 287 | 10/1990 |
| EP | 0 494 119 | 7/1992 |
| EP | 0 355 131 B1 | 9/1996 |
| WO | WO 89/03838 A1 | 5/1989 |
| WO | WO 89/02733 | 6/1989 |
| WO | WO 90/00555 | 1/1990 |
| WO | WO 91/16920 | 11/1991 |
| WO | WO 91/18914 | 12/1991 |
| WO | WO 91/19721 | 12/1991 |
| WO | WO 92 08727 | 5/1992 |
| WO | WO 92/08727 | 5/1992 |
| WO | WO 92/15308 | 9/1992 |
| WO | WO 92/18517 | 10/1992 |
| WO | WO 92/18517 A | 10/1992 |
| WO | WO 93/00910 | 1/1993 |
| WO | WO 93/01202 A1 | 1/1993 |
| WO | WO 92/01138 | 1/1994 |
| WO | WO 94/20523 | 9/1994 |
| WO | WO 94/26273 | 11/1994 |
| WO | WO 94/26761 A1 | 11/1994 |
| WO | WO 94/29331 | 12/1994 |
| WO | WO 95/07086 | 3/1995 |
| WO | WO 95/07287 A | 3/1995 |
| WO | WO 95/32984 A | 12/1995 |
| WO | WO 96/11204 | 4/1996 |
| WO | WO 96/13512 | 5/1996 |
| WO | WO 96/15132 | 5/1996 |
| WO | WO 96/40164 | 12/1996 |
| WO | WO 96/40164 A | 12/1996 |
| WO | WO 98/15563 | 10/1997 |
| WO | WO 00/09531 A | 2/2000 |

OTHER PUBLICATIONS

Boudou, V *Nucleosides & Nucleotides*, vol. 18, No. 45, 1999, pp. 607–609.

Skaric, V. *Croatica Chemica ACTA*, vol. 48, No. 3, 1976, 35 1–359.

Ryu, EK et al., *J. of Carbohydrates, Nucleosides Nucleotides*, vol. 4, No. 6(1977), pp. 387–408.

Wang, P. et al., *Antiviral Research*, vol. 46, No. 1/2, 1998, pp. 19–44.

(Continued)

*Primary Examiner*—Howard V Owens
(74) *Attorney, Agent, or Firm*—Sherry M. Knowles, Esq.; King & Spalding LLP

(57) ABSTRACT

The present invention relates to compounds, compositions and methods for the treatment of a host infected with a hepatitis B virus. Specifically, compound and compositions of 3'-esters of 2'-deoxy-β-L-nucleosides are disclosed, which can be administered either alone or in combination with other anti-hepatitis B agents. Compound and compositions of 3',5'-diesters of 2'-deoxy-β-L-nucleosides are disclosed, which can be administered either alone or in combination with other anti-hepatitis B agents, are also disclosed.

25 Claims, 13 Drawing Sheets

OTHER PUBLICATIONS

Beauchamp, L. M., et al., "Amino Acid ester prodrugs of acyclovir. *Antiviral Chem. Chemother.*" 1992, 3(3) 157–164.}.

Bhat, V. et al., "A Simple and Convenient Method for the Selective N–Acylations of Cytosine Nucleosides." *Nucleosides & Nucleotides*, 1989, 8(2), 179–183.

Jones, R. et al., "Minireview: nucleotide prodrugs." *Antiviral Research*, (1995) 27, 1–17.

Lin et al., "Synthesis and Antiviral Activity of Various 3'–Azido Analogues of Pyrimidine Deoxyribonucleosides against Human Immunodeficiency Virus (HIV–1, HTLV–III/LAV." *I. Med. Chem.* 1988, 31(2), 336–340.

Mahmoudian, "Quantitative Structure–Activity Relationships (QSARs) of Pyrimidine Nucleosides as HIV–1 Antiviral Agents." *Pharm. Research* 1991, 8(1), 43–6.

Tsai et al., "Effect of Anti–HIV 2'–B–Fluoro–2',3'–Dideoxynucleoside Analogs on the Cellular Content of Mitochondrial DNA and on Lactate Production." *Biochem. Pharmacol.* 1994,–48(7), 1477–81.

Arner and Eriksson, "Mammalian Deoxyribonucloside Kinases," *Pharm. Ther.*, 1995, 67(2), 155–186.

Berk et al., "A Genetically Distinct Tymidine Kinase in Mammalian Mitochondria," *J Biol Chem*, 1973, 248, 2722–2729.

Bestwick et al., "Selective Expansion of Mitochondrial Nucleoside Triphosphate Pools in Antimetabolite–treated HeLa Cells," *J Biol Chem*, 1982, 257, 9300–9304.

Bloch, et al. "The Role Of The 5'–Hydroxyl Group Of Adenosine In Determining Substrate Specificity For Adenosine Deaminase." *J. Med. Chem.* 10(5), 908–12 (Sep. 1967).

Bridges et al., "Characterization of a dCTP Transport Activity Reconstituted from Human Mitochondria." *J. Biol. Chem*, Feb. 19, 1999, 274(8), 4620–4625.

Bridges et al., "Identification of a novel mitochondrial dNTP carrier and its interaction with anti–HIV nucleoside analogs," *Proc. Am. Assoc. Cancer Res.*, Mar. 1997, 38, 414.

Bridges et al., "Inhibition of Mammalian DNA Polymerase–Associated 3' to 5' Exonuclease Activity by 5'–Monophosphates of 3'–Azido–3'–Deoxythymine and 3'–Amino–3'–Deoxythymidine," *Biochemical Pharmacology*, 1993, 45(8), 1571–1576.

Bryant et al., "Antiviral L–Nucleosides Specific for Hepatitis B Virus Infection," *Antimicrobial Agents and Chemotherapy*, 45(1), 229–235 (Jan. 2001).

Chang et al., "Biochemical Pharmacology of (+)– and (–)–2',3'–Dideoxy–3'–thiacytidine as Anti–hepatitis B Virus Agents," *J Biol Chem*, Nov. 5, 1992, 267(31), 22414–22420.

Chang, et al., "Deoxycytidine Deaminase–resistant Stereoisomer is the Active Form of (–)–2',3'–thiacytidine in the Inhibition of Hepatitis B Virus Replication," *Journal of Biological Chemistry*, vol. 267(20), 13938–13942 (Jul. 15, 1992).

Chariot et al., "Zidovudine–induced mitochondrial disorder with massive liver steatosis myopathy, lactic acidosis, and mitochondrial DNA depletion," *J. Hepatology*, 1999, 30, 156–160.

Chen et al., "Characterization of Pyrimidine Deoxyribonucleoside Kinase (Thymidine Kinase) and Thymidylate Kinase as a Multifunctional Enzyme in Cells Transformed by Herpes Simplex Virus Type 1 and in Cells Infected with Mutant Strains of Herpes Simplex Virus," *J Virol*, Jun. 1979, 30, 942–945.

Chen et al., "Delayed Cytatoxicity and Selective Loss of Mitochondrial DNA in Cells Treated with the Anti–human Immunodeficiency Virus Compound 2',3'–Dideoxycytidine," *J Biol Chem*, 1989, 264, 11934–11937.

Chen et al., "The Role of Cytoplasmic Deoxycytidine Kinase in the Mitochondrial Effects of the Anti–human Immunodeficiency Virus Compound 2',3'–Dideoxycytine," *J Biol Chem*, Feb. 15, 1992, 267(5), 2856–2859.

Cui et al., "Effect of Nucleoside Analogs on Neurite Regeneration and Mitochondrial DNA Synthesis in PC–12 Cells," *J. of Pharmacology and Experimental Therapeutics*, 1997, 280(3), 1228–1234.

Davis et al., "In Situ Localization of Mitochondrial DNA Replication in Intact Mammalian Cells," *J Cell Biol*, 1996, 135, 883–893.

Davisson et al., "Synthesis of Nucleotide 5'–Diphosphates from 5'–O–Tosyl Nucleosides," *J. Org. Chem.*, 52(9), 1794–1801 (1987).

Doong et al., "Inhibition of the replication of hepatitis B virus in vitro by 2',3'–didexoy–3'–thiacytidine and related analogues," *Proc. Natl. Acad. Sci.*, Oct. 1991, 88, 8495–8499.

Du et al, Synthesis, "Anti–Human Immunodeficiency Virus and Anti–Hepatitis B Virus Activities of Novel Oxaselenolane Nucleosides," *J. of Med. Chem.*, (40)19, 2991–2993 (Sep. 12, 1997).

Dutschman et al., "Metabolism of 2',3'–dideoxy–2', 3'–didehydro–β–L–(–)–5–Fluotocytidine and Its Activity in Combination with Clinically Approved Anti–Human Immunodeficiency Virus β–D–(+) Nucleoside Analogs In Vitro," *Antimicrobial Agents and Chemotherapy*, Jul. 1998, 42(7), 1799–1804.

Furman, et al., "The Anti–Hepatitis B Virus Activities, Cytotoxicities, and Anabolic Profiles of the (–) and (+) Enantiomers of cis–5–Fluoro–1–[2–(Hydroxymethyl)–1, 3–oxathiolane–5–yl]–Cytosine" *Antimicrobial Agents and Chemotherapy*, 36(12) 2686–2692 (Dec. 1992).

Glonek, et al. "Full anhydrization of methylenediphosphonic acid and of phosphoric acids by a carbodiimide" Inorg.Chem., 1975 vol. 14(7); 1597–602.

Gosselin, G. et al. "Synthesis and Antiviral Evaluation of β–L–Xylofuranosyl Nucleosides of the Five Naturally Occuring Nucleic Acid Bases", *Journal of Heterocyclic Chemistry*, 1993, 30 (Oct.–Nov.), 1229–1233.

Hernandez–Santiago et al., "Pharmacology of β–L–Thymidine and β–L–2'–Deoxycytidine in HepG2 Cell and Primary Human Hepatocytes: Relevance to Chemotherapeutic Efficacy against Hepatitis B Virus," *Antimicrobial Agents and Chemotherapy*, Jun. 2002, 46(6), 1728–1733.

Hoard, et al., "Conversion of Mono– and Oligodeoxyribonucleotides to 5'–Triphosphates," *J. Am. Chem. Soc.*, 87(8), 1785–1788 (1965).

Holy, "Nucleic Acid Components and Their Analogs. CLIII. Preparation of 2'–deoxy–L–Ribnucleosides of the Pyrimidine Series," *Collect. Czech. Chem. Commun.* (1972), 37(12), 4072–87.

Hostetler, K.Y., et al. "Greatly Enhanced Inhibition Of Human Immunodeficiency Virus Type I Replication In CEM And HT4–6C Cells By 3'–Deoxythymidine Diphosphate Dimyristoylglycerol, A Lipid Prodrug Of 3'–Deoxythymidine." (Sep. 1992) *Antimicrob Agents Chemother.* 36:2025–2029.

Hostetler, K.Y., et al. "Synthesis And Antiretroviral Activity Of Phospholipid Analogs Of Azidothymidine And Other Antiviral Nucleosides." (Apr. 15, 1990) *J. Biol Chem.* 265(11):6112–7.

Imai et al., "Studies on Phosphorylation. IV. Selective Phosphorylation of the Primary Hydroxyl Group in Nucleosides." *J. Org. Chem.*, 34(6), 1547–1550 (Jun. 1969).

Jones, R. et al., "Mini Review: Nucleotide prodrugs," *Antiviral Research*, 27, 1–17 (1995).

Jurovčik and Holy "Metabolism of pyrimidine L–nucleosides," *Nucleic Acids Research*, Aug. 1976, 3(8), 2143–2153.

Korba et al., "A cell culture assay for compounds which inhibit hepatitis B virus replication." *Antiviral Res.*, 15:217 (1991).

Krayevsky and Chernov, "Should the Asymmetric of Enzymatic Active Centers Always Correlate with the Asymmetry of their Substrates?," *J. of Bionolecular Structure & Dynamics*, 1996, 14(2), 225–230.

Kucera, L.S., et al.. "Novel membrane–interactive ether lipid analogs that inhibit infectious HIV–1 production and induce defective virus formation." *AIDS Res Hum Retroviruses*. 6:491–501 (May 1990).

Labenz et al., "Analysis of the TK Enzyme Complex Induced by HSV Types 1 and 2 by Means of Isoelectric Focusing and Polyacyrlamide Gel Electrophoresis," *Arch Virol*, 1982, 71, 235–249.

Lin et al., "Design and Synthesis of 2',3'–Dideoxy–2', 3'–didyhydro–β–L–cytidine (β–L–Fd4C). Two Exceptionally Potent Inhibitors of Human HBV and Potent Inhibitors of HIV In Vitro," *J. Med. Chem.*, 39(9), 1757–1759 (Apr. 26, 1996).

Lin et al., "Synthesis and Biological Evaluation of 2',3'–Dideoxy–L–pyrimidine Nucleosides as Potential Antiviral Agents against HIV and HBV," *J. Med. Chem*, 1994, 97,798–803.

Lin et al., "Synthesis of Several Pyrimidine L–Nucleoside Analogues as Potential Antiviral Agents," *Tetrahedron Letters*, vol. 51(4), 1055,1068 (1995).

Maga et al., "Lack of stereospecificity of acid pseudorabies virus thymidine kinase," *Biochem, J.* , 294(2), 381–385 (Sep. 1, 1993).

Mansour et al., "Stereochemical Aspects of the Anti–HCMV Activity of Cytidine Nucleoside Analogues," *Antiviral Chemistry & Chemotherapy*, 6(3), 138–142 (1995).

Nakayama, C., et al., "Synthetic Nucleosides and Nucleotides, XX, Synthesis of Various 1–β–Xylofuranosyl–5–Alkylurcils and Related Nucleosides." *Nucleoside, Nucleotides*, 1, 139–146 (1982).

Pankiewcz. et al. Efficient synthesis of methylenebis(phosphonate) analogues of P1,P2–disubtituted phyrophospates of biological interest. (Apr. 15, 1997), 119, 3691–3692.

Pankiewicz. et al. "Synthesis of methylenebis(phosphonate) analogs of APP Ribose" Collect. Czech. Chem. Commun. (Sep. 23, 1996), 61; S92–S–95.

Pan–Zhou et al., "Differential Effects of Antiretroviral Nucleoside Analogs on Mitochondrial Function in HepG2 Cells," *Antimicrobial Agents and Chemotherapy*, Mar. 2000, 44(3), 496–503.

Robins, "Selective Deoxygenation and Modification at C2' of Nucleosides," *Nucleic Acids Research Symposium Series*, vol. 11, pp. 1–4, Kyoto, Japan, Nov. 24–26, 1982, A.E. Pritchard (ed), IRL Press, Ltd., Oxford, England, 1982.

Robins, M. J. et al. "Purine nucleosides. XXIX. The synthesis of 2'–deoxy–L–adenosine and 2'–deoxy–L–guanosine and their alpha anomers." *J. Org. Chem.* Mar. 1970, 35, 636–639.

Saneyoshi, M., et al., "Synthetic Nucleosides and Nucleotides. XIII. Stannic Chloride Catalyzed Ribosylation of Several 6–Substituted Purines." *Chem. Pharm. Bull.*, 27, 2518–2521 (1979).

Schinazi, et al., "Selective Inhibition of Human Immunodeficiency Viruses by Racemates and Enantiomers of cis–5–Fluoro–1–[2–(Hydroxmethyl)–1, 3–Oxathiolane–5–yl]Cytosine," *Antimicrobial Agents and Chemotherapy*, 36(11), 2423–2431 (1992).

Schinazi, et al., "Effect of Combinations of Acylovir with Vidarabine or its Monophosphate on Herpes Simplex Viruses in Cell Culture and in Mice," *Antimicrobial Agents and Chemotherapy*, 22(3), 499, (1982).

Shuto, S., et al. "A facile one–step synthesis of 5'–phosphatidylnucleosides by an enzymatic two–phase reaction." *Tetrahedron Letters*. 28. 199–202 (1987).

Soderlund and Arner, "Mitochondrial versus Cytosololic Activities of Deoxyribonucleoside Salvage Enzymes," *Purine and Pyrimidine Metabolism in Man VIII*, A. Shota & M. Taylor (ed.). Plenum Press, New York, 1995, 201–204.

Spadari et al., "L–Thymidine is Phosphorylated by Herpes Simplex Type 1 Thymidine Kinase and Inhibits Viral Growth," *J. Med. Chem.* (1992), 35(22), 4214–4220.

Tyrsted et al. "Inhibition of the synthesis of 5–phosphoribosyl–1–pyrophosphate by 3'–deoxy–adenosine and structurally related nucleoside analogs." *Biochim. Biophys. Acta.* (Feb. 26, 1968), 155(2), 619–22.

Verri et al. "Lack of enantiospecificity of human 2'–deoxycytidine kinase: relevance for the activation of beta–L–deoxycytidine analogs as antineoplastic and antiviral agents," *Molecular Pharmacology*. (Jan. 1997), 51(1), 132–138.

Verri et al., "Relaxed Enantioselectivity of Human Mitochondrial Thymidine Kinase and Chemotherapeutic Uses of L–Nucleoside Analogues," *Biochem. J.* (1997), 328(1), 317–320 (Nov. 15, 1997).

Von Janta–Lipinski et al., "Newly Synthesized L–Enantiomers of 3'–Fluoro–Modified β–2'–Deoxyribonucleoside 5'–Triphosphates Inhibit Hepatitis B DNA Polymerase but not the Five Cellular DNA Polymerases α, β, γ, δ, and ε Nor HIV–1 Reverse Transcriptase," *J. Medicinal Chemistry*. 41(12), 2040–2046 (Jun. 4, 1996).

Zhang, W., et al. "Removal of Silyl Protecting Groups from Hydroxyl Functions with Ammonium Fluoride in Methanol." *Tetrahedron Letter.*, 33, 1177–1180(192).

Zhu et al., "Anti–Hepatitis B Virus Activity and Metabolism of 2',3'–dideoxy–2',3'–didehydro–β–L–(–)–5–Fluorocytidine," *Antimicrobial Agents and Chemotherapy*, Jul. 1998, 42(7), 1805–1810.

Zhu et al., "Incorporation of Nucleoside Analogs into Nuclear or Mitochondrial DNA Is Determined by the Intracellular Phosphorylation Site," *J Biol Chem*, 2000, 275(35), 26727–26731.

* cited by examiner

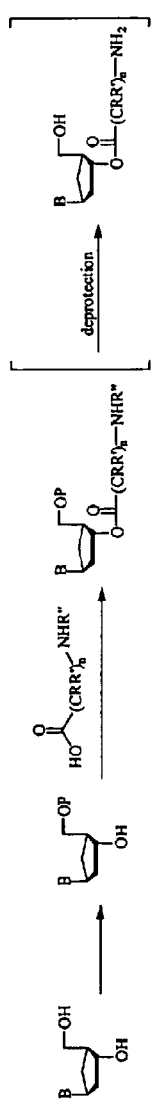
Figure 1a: Synthesis of 3'-valinyl esters of 2'-deoxy-β-L-cytidine
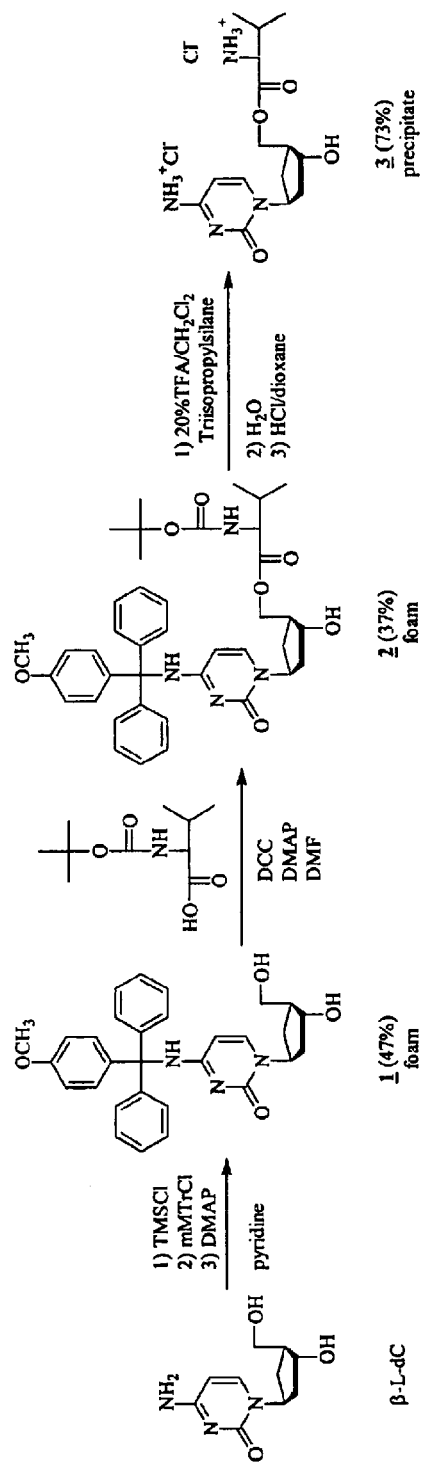
Figure 1b: Synthesis of 5'-valinyl esters of 2'-deoxy-β-L-cytidine
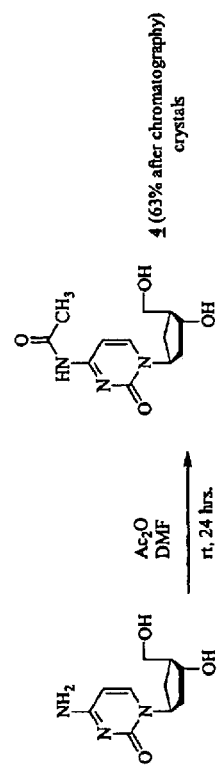
Figure 2: Synthesis of N⁴-acetyl-2'-deoxy-β-L-cytidine

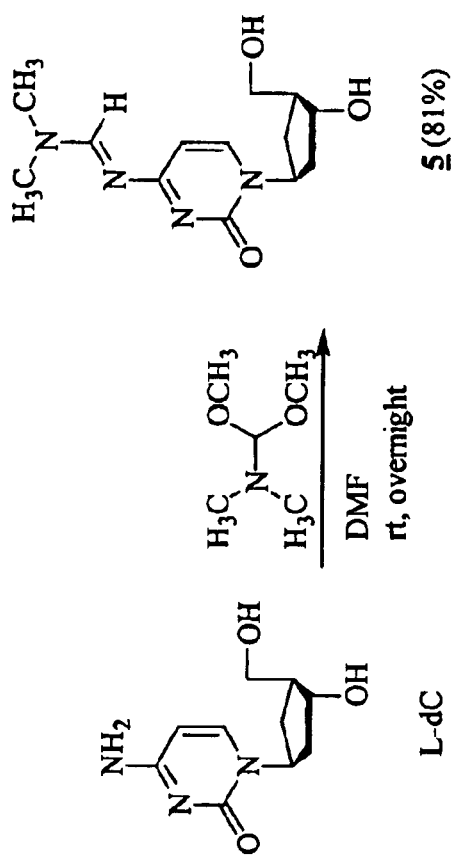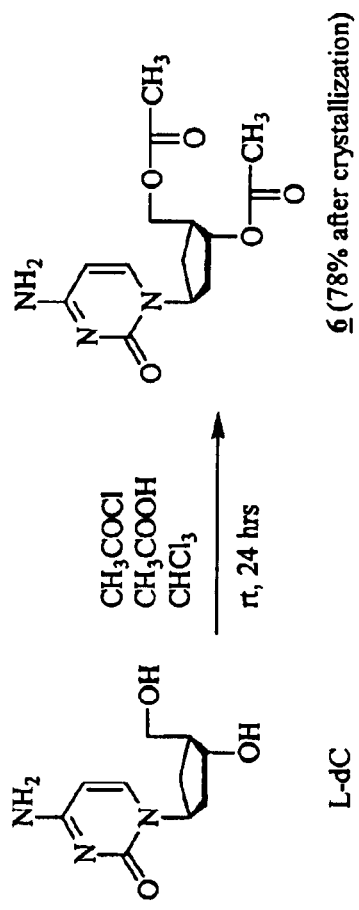
Figure 3: Synthesis of $N^4$-[(dimethylamino)methylene]-2'-deoxy-β-L-cytidine
Figure 4: Synthesis of 3',5'-di-O-acetyl-2'-deoxy-β-L-cytidine

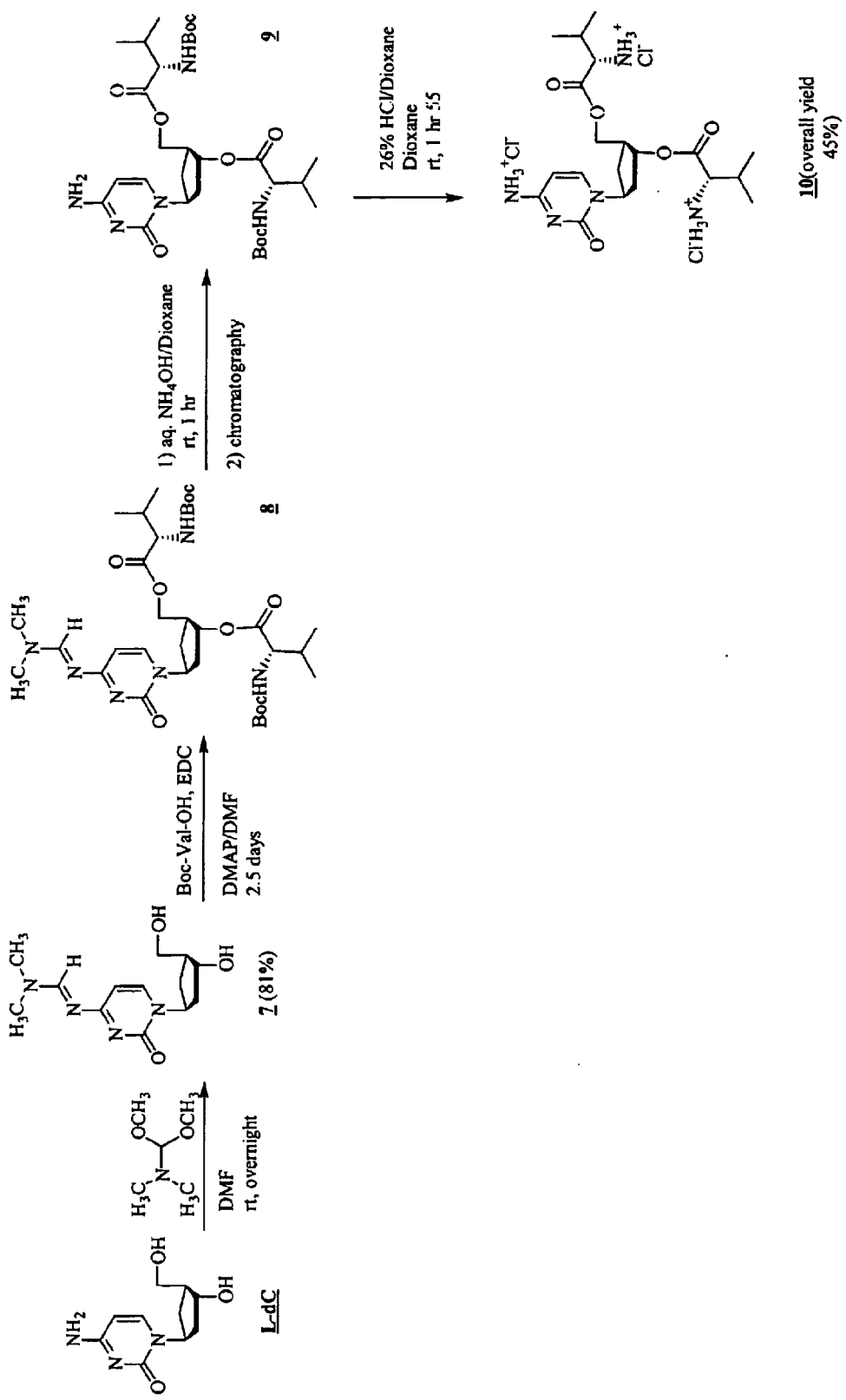
Figure 5: Synthesis of 3',5'-di-O-valinyl esters of 2'-deoxy β-L-cytidine

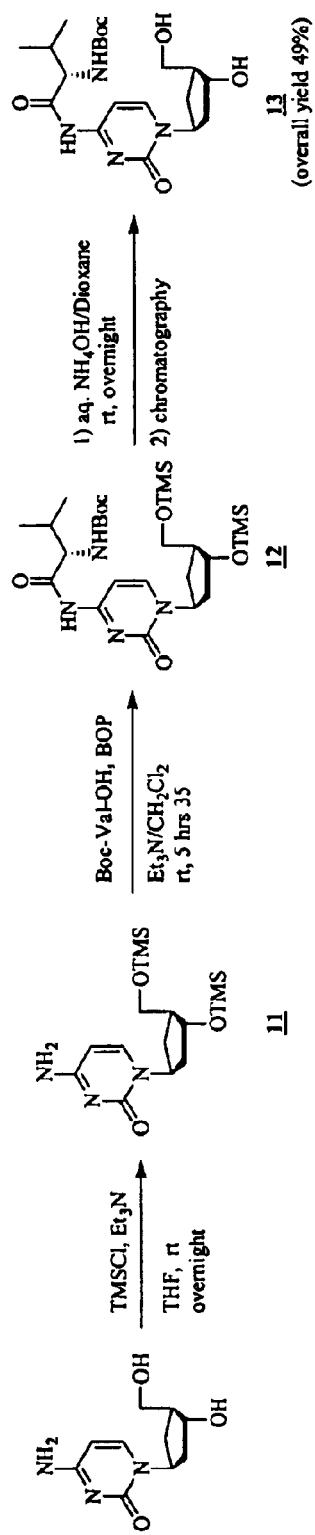
Figure 6: Synthesis of $N^4$-Boc-valinyl ester of 2'-deoxy-β-L-cytidine
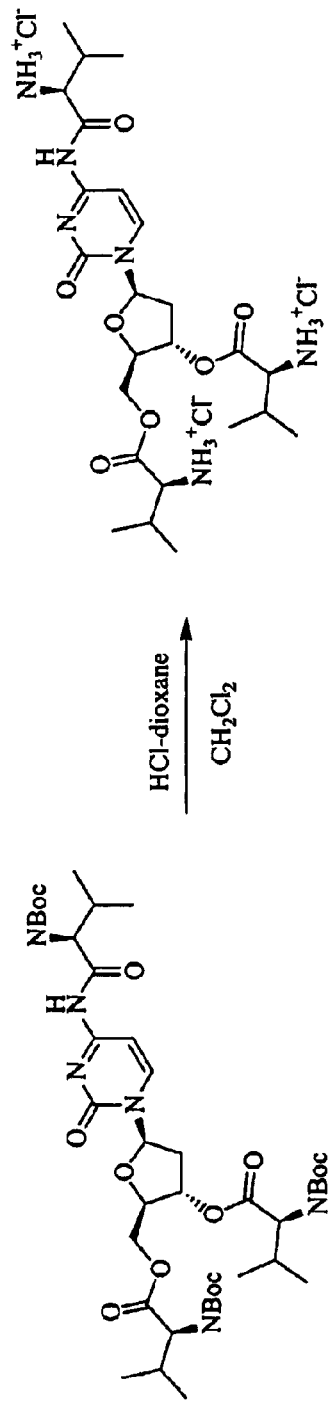
Figure 7: Synthesis of 3',5',$N^4$-tri-(L-valinyl)-L-2'-deoxycytidine

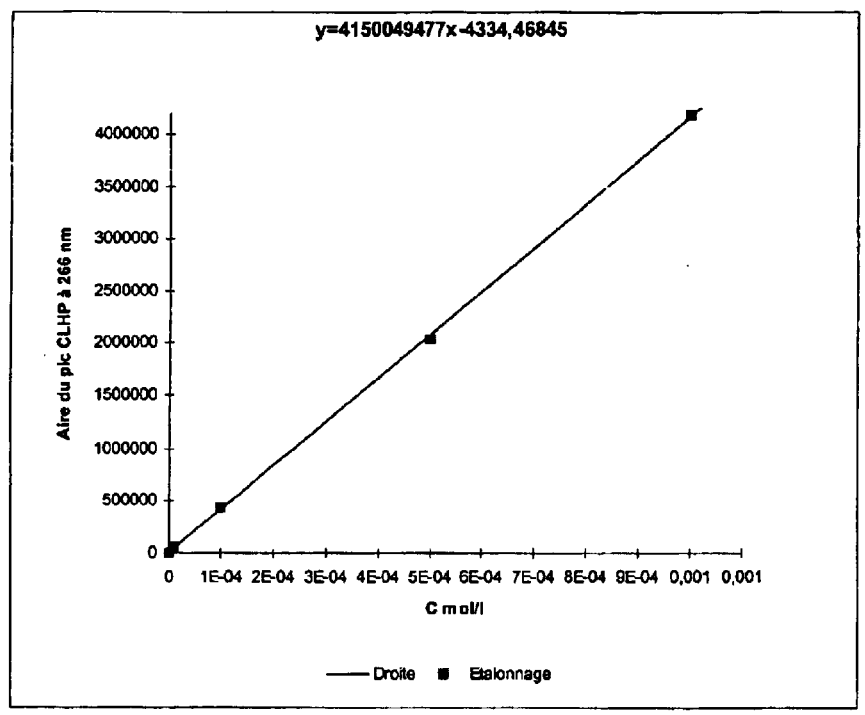
Figure 8a: Solubility Calibration Curve for D-dC
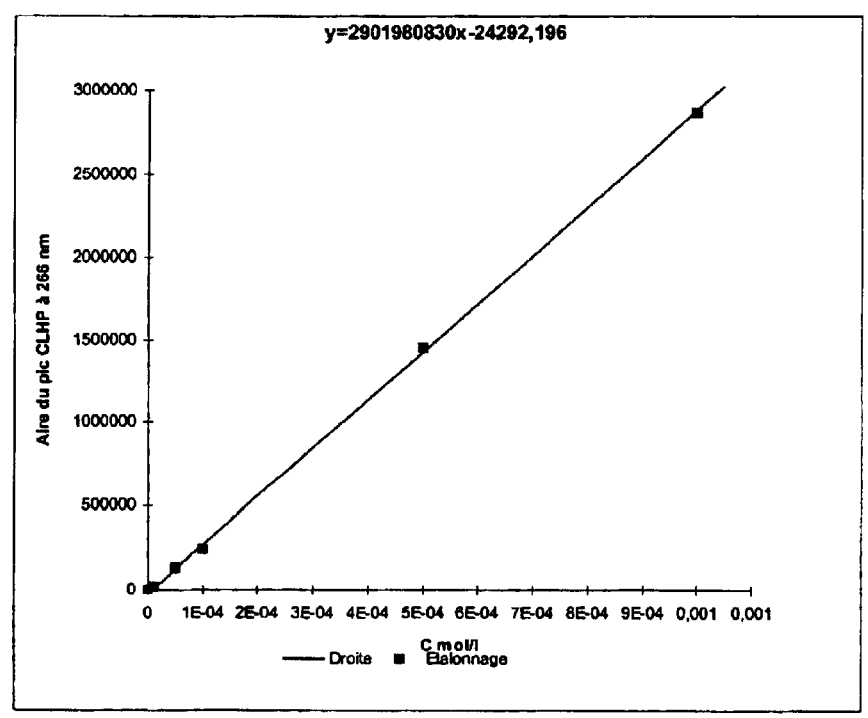
Figure 8b: Solubility Calibration Curve for the 3',5'-Divalinyl Ester of L-dC

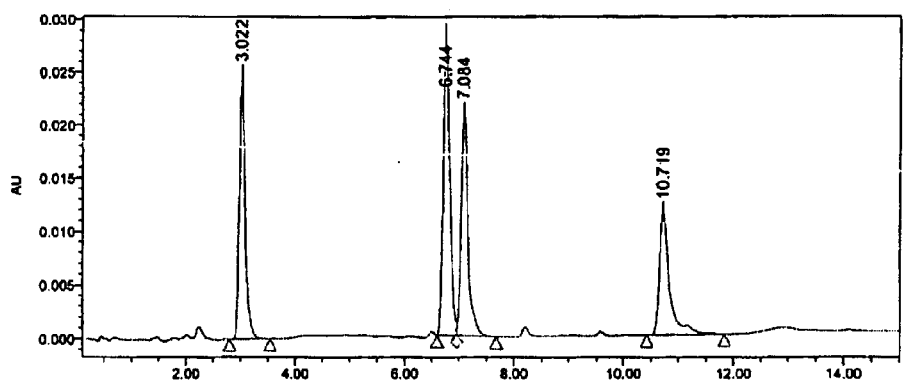
Figure 9a: HPLC profile – 7.5 hours at pH of 7.42
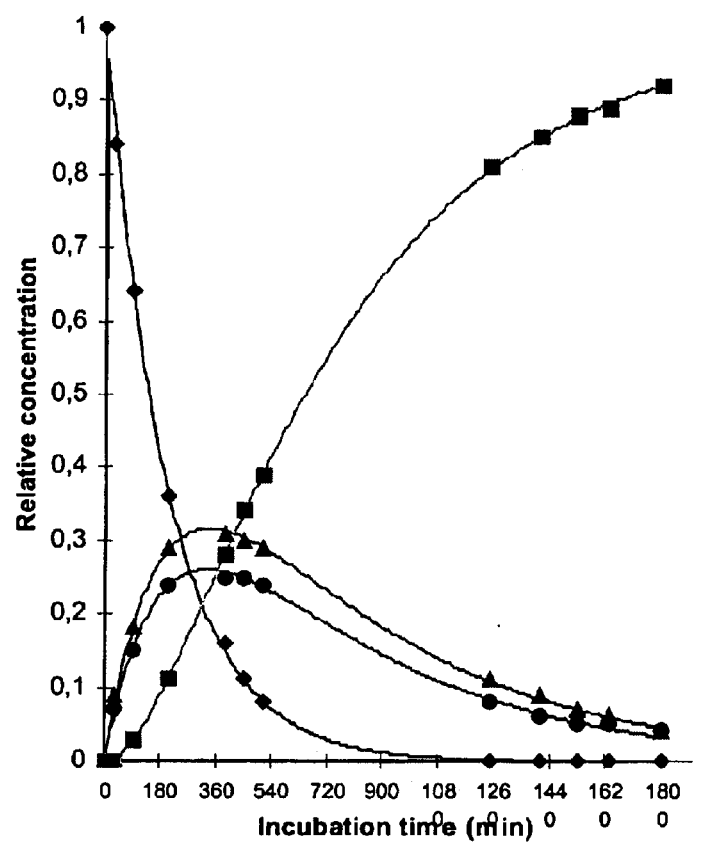
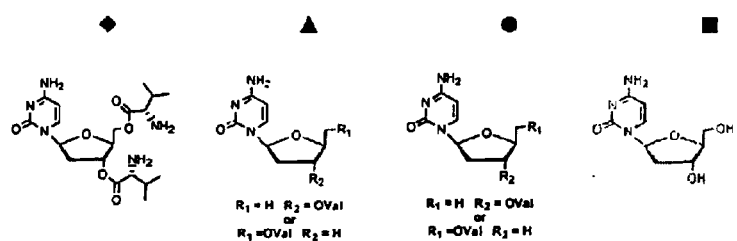
Figure 9b: Kinetics curves at pH of 7.42

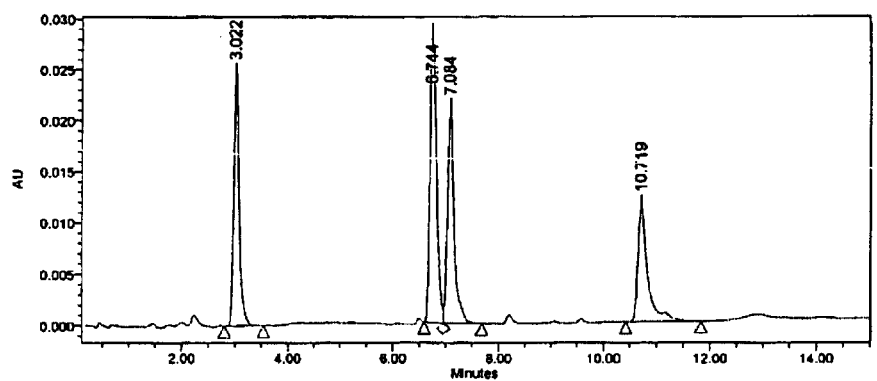
Figure 10a: HPLC profile – 5.33 hours at pH of 7.20
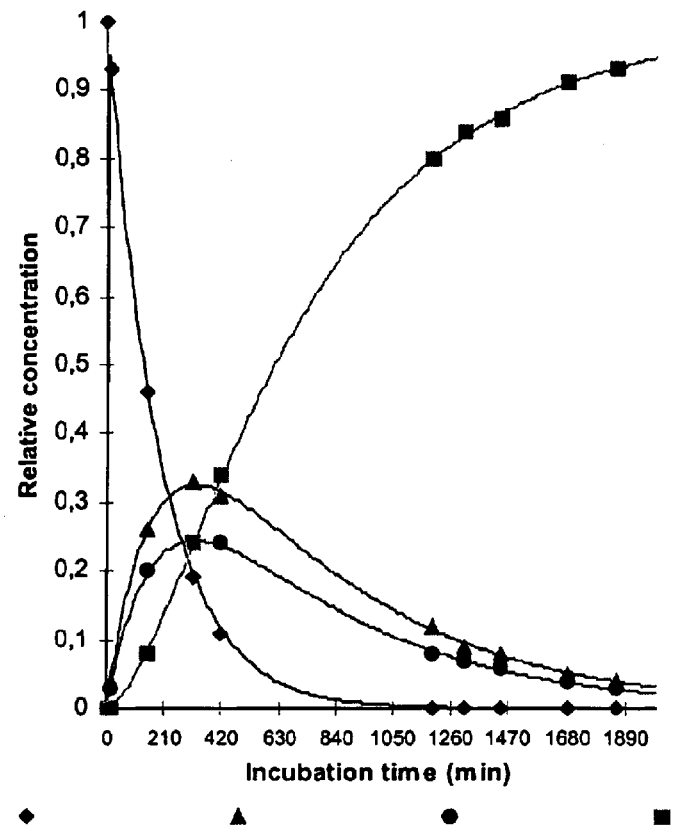
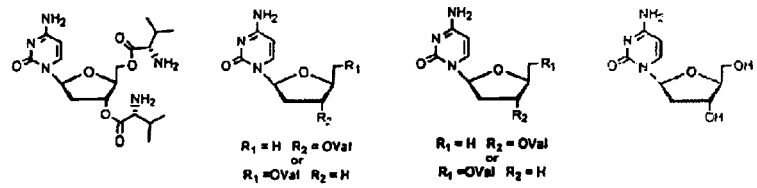
Figure 10b: Kinetics curves at pH of 7.20

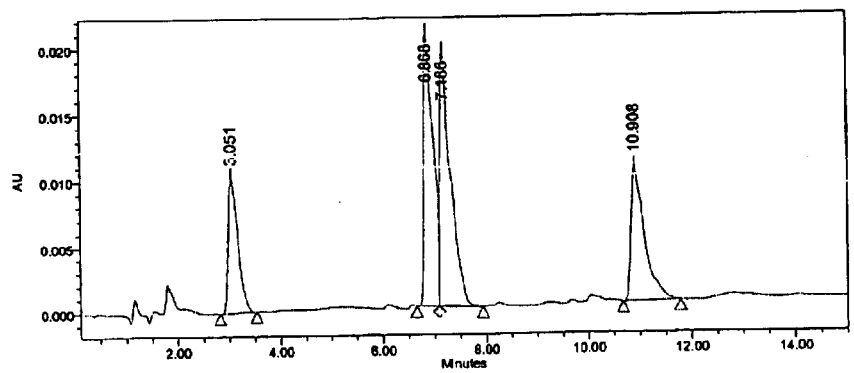
Figure 11a: HPLC profile – 95.7 hours at pH of 4.51
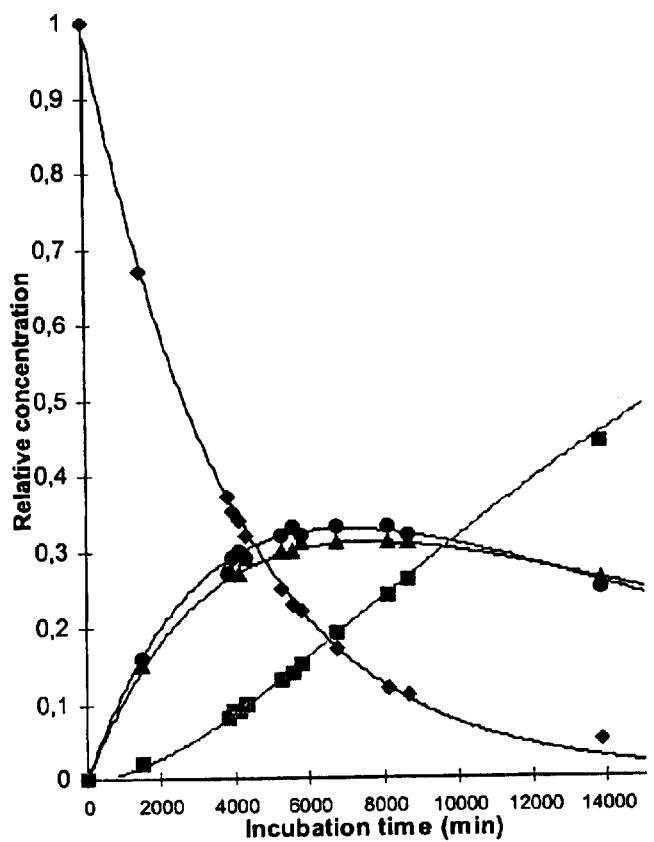
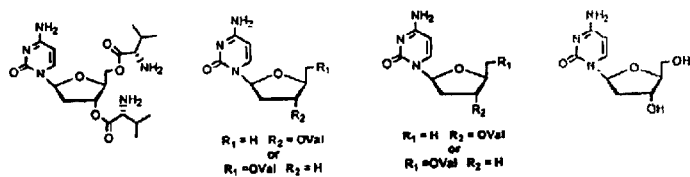
Figure 11b: Kinetics curves at pH of 4.51

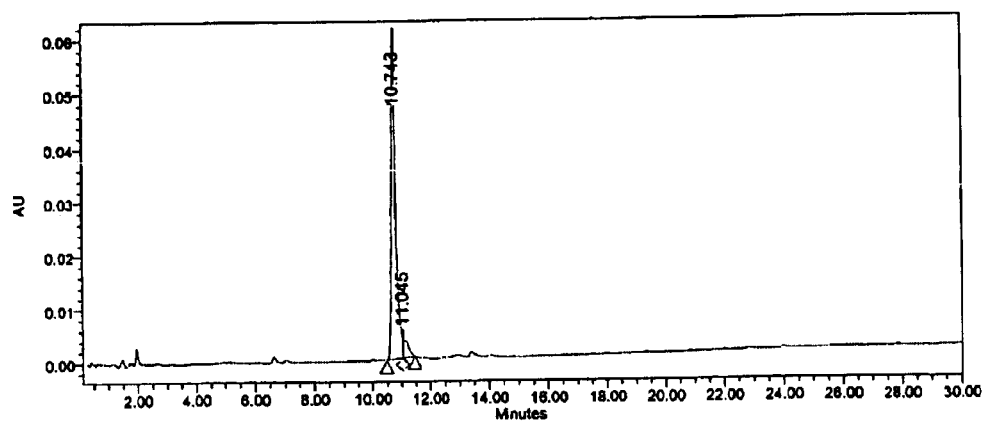
Figure 12: HPLC profile – 48 hours at pH of 1.23
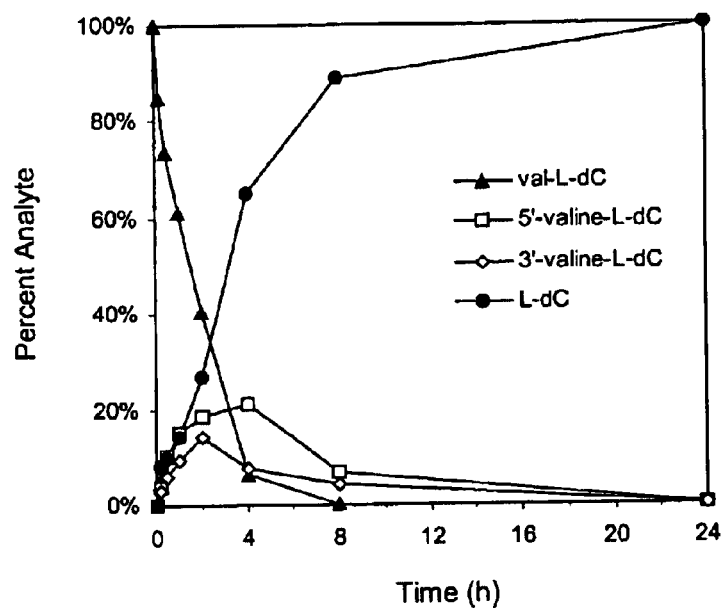
Figure 13 *In Vitro* Metabolism of 3',5'-Dival-L-dC in Human Plasma

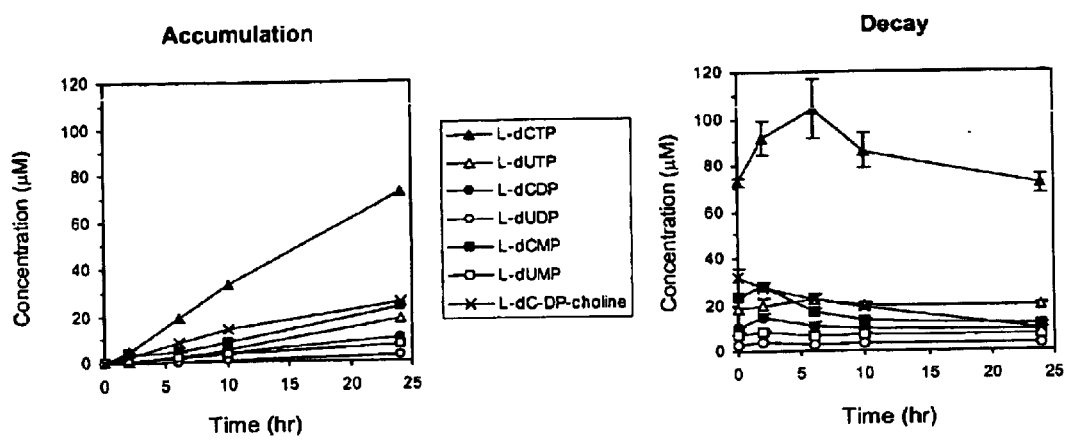
Figure 14 Intracellular Metabolism of L-dC in HepG2 Cells
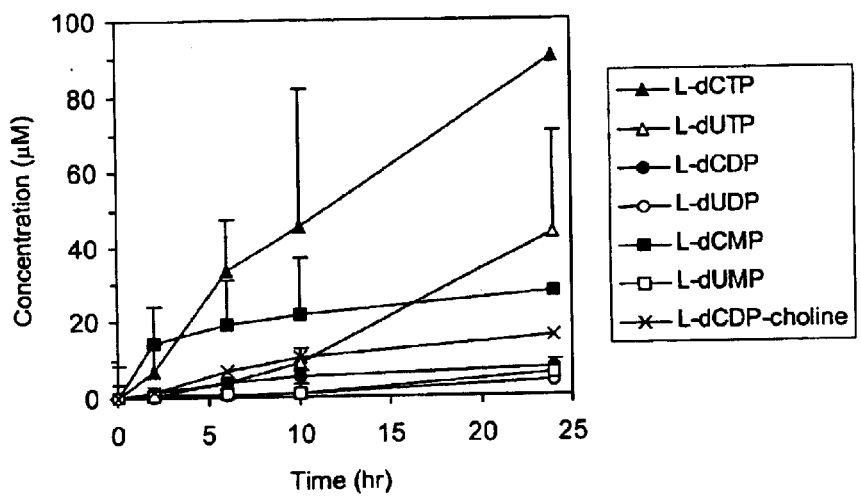
Figure 15 Intracellular Metabolism of L-dC in Primary Human Hepatocytes

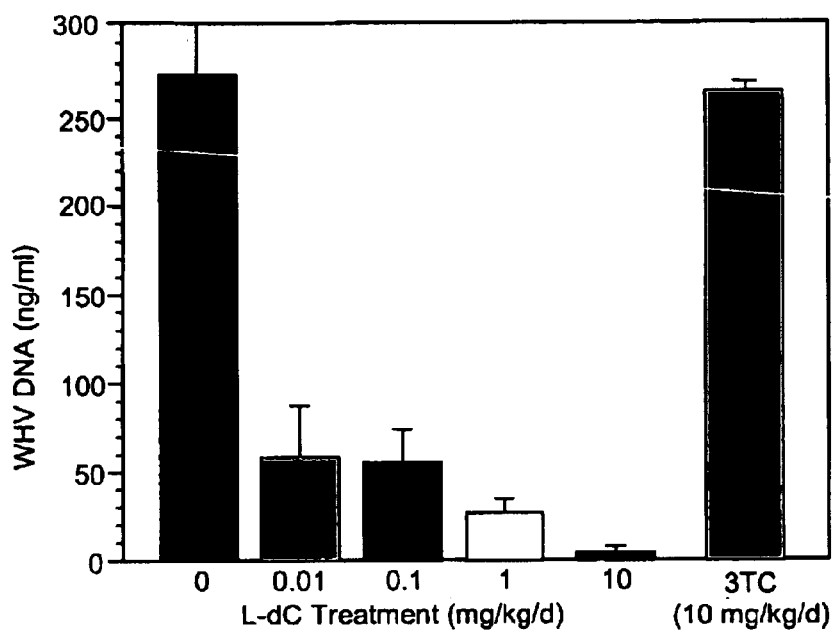
Figure 16    Antiviral Dose Response of L-dC in the Woodchuck Model
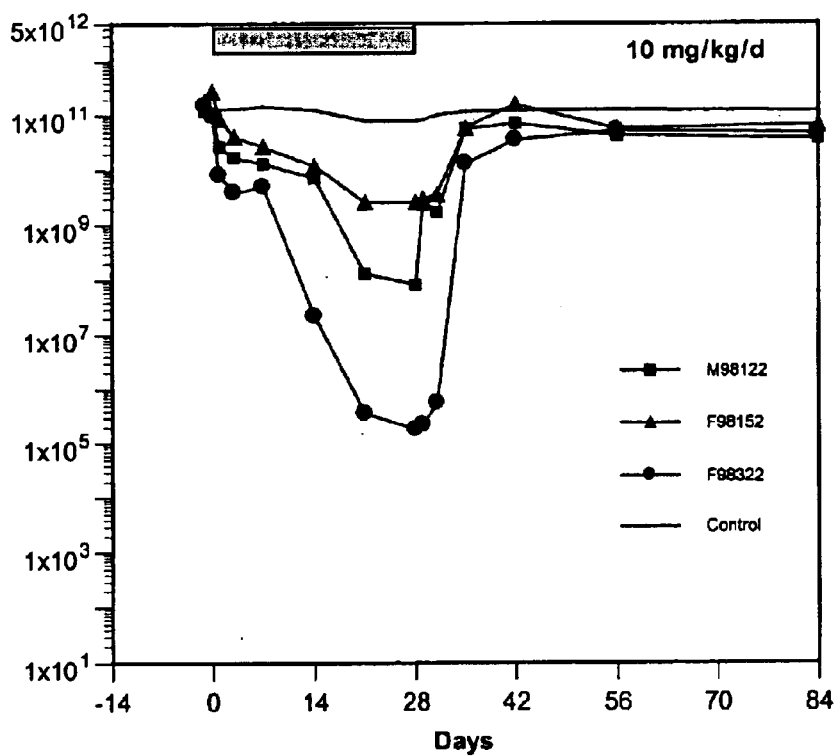
Figure 17    Antiviral Activity of L-dC in the Woodchuck Model

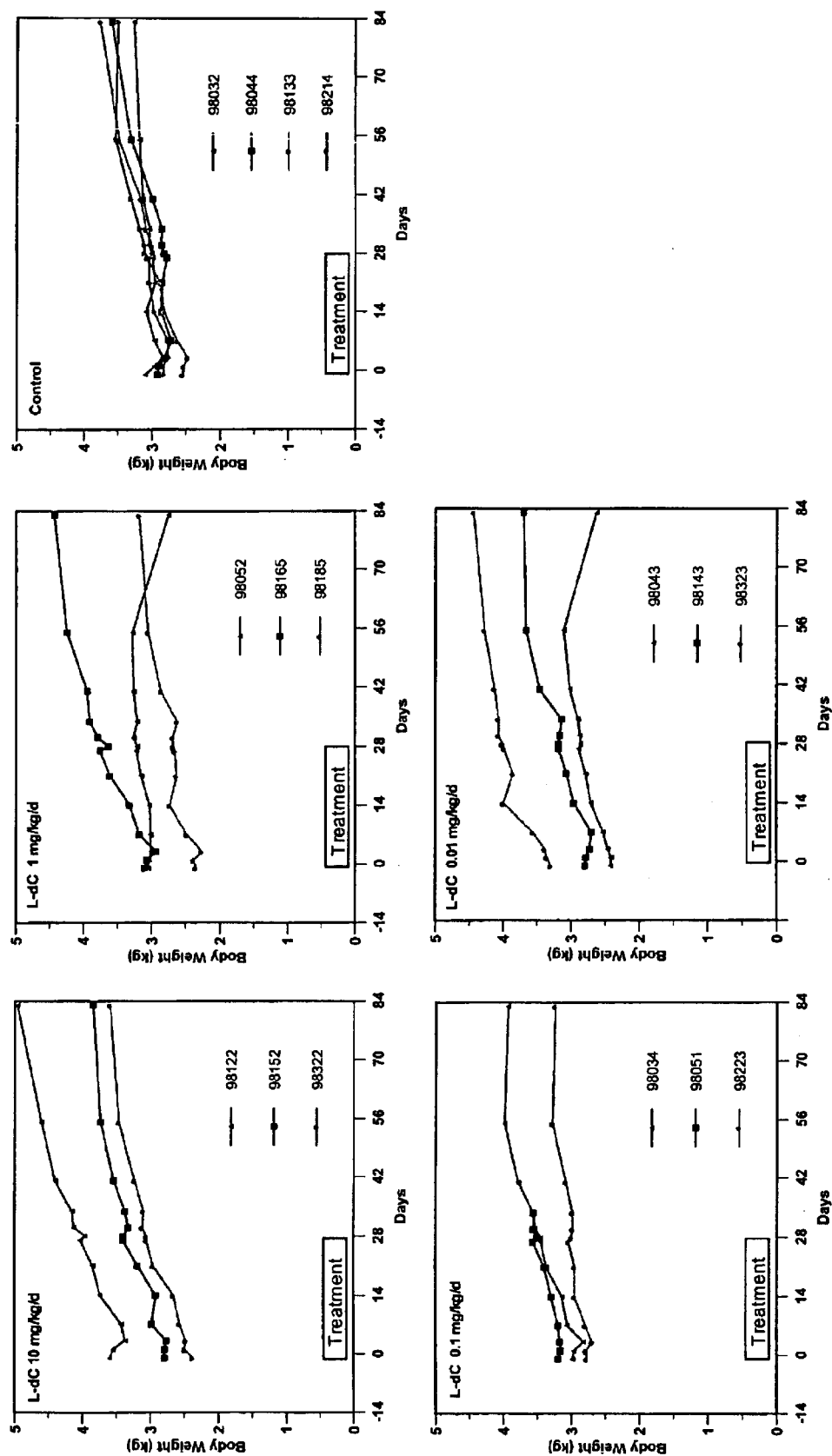
Figure 18 Body Weights of Woodchucks Orally Treated with L-dC – 28 Days

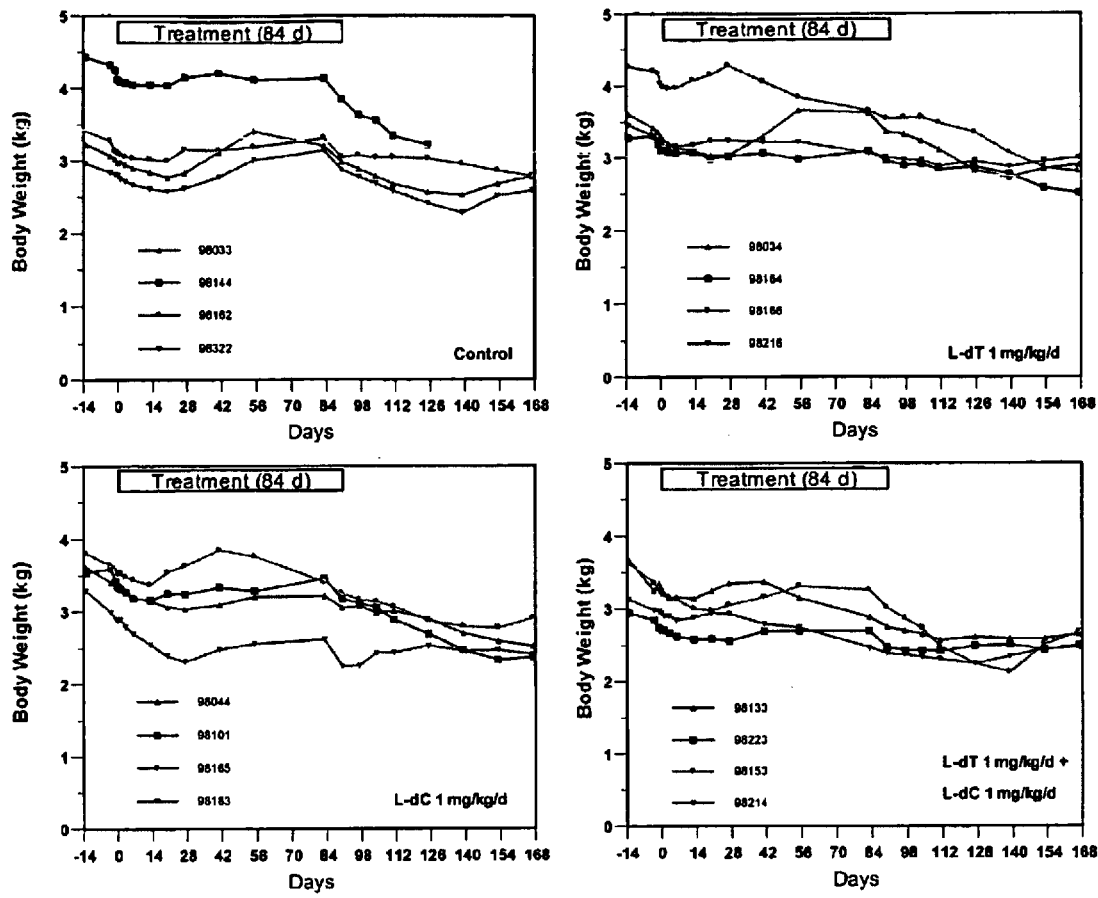
Figure 19  Body Weights of Woodchucks Orally Treated with L-dC – 12 Weeks

3'-PRODRUGS OF 2'-DEOXY-β-L-NUCLEOSIDES

This application claims priority to U.S. provisional application No. 60/212,100, filed on Jun. 15, 2000.

FIELD OF THE INVENTION

The present invention relates to 3'-prodrugs of 2'-deoxy-β-L-nucleosides for the treatment of hepatitis B virus.

BACKGROUND OF THE INVENTION

Hepatitis B virus ("HBV") is second only to tobacco as a cause of human cancer. The mechanism by which HBV induces cancer is unknown, although it is postulated that it may directly trigger tumor development, or indirectly trigger tumor development through chronic inflammation, cirrhosis and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. Chronic persistent hepatitis can cause fatigue, cirrhosis of the liver and hepatocellular carcinoma, a primary liver cancer. In western industrialized countries, high risk groups for HBV infection include those in contact with HBV carriers or their blood samples. The epidemiology of HBV is in fact very similar to that of acquired immunodeficiency syndrome, which accounts for why HBV infection is common among patients with AIDS or HIV-associated infections. However, HBV is more contagious than HIV.

Daily treatments with α-interferon, a genetically engineered protein, have shown promise. A human serum-derived vaccine has also been developed to immunize patients against HBV. Vaccines have been produced through genetic engineering. While the vaccine has been found effective, production of the vaccine is troublesome because the supply of human serum from chronic carriers is limited, and the purification procedure is long and expensive. Further, each batch of vaccine prepared from different serum must be tested in chimpanzees to ensure safety. In addition, the vaccine does not help the patients already infected with the virus.

An essential step in the mode of action of purine and pyrimidine nucleosides against viral diseases, and in particular, HBV and HIV, is their metabolic activation by cellular and viral kinases, to yield the mono-, di- and triphosphate derivatives. The biologically active species of many nucleosides is the triphosphate form, which inhibits DNA polymerase or reverse transcriptase, or causes chain termination.

A number of synthetic nucleosides have been identified which exhibit activity against HBV. The (-)-enantiomer of BCH-189 (2',3'-dideoxy-3'-thiacytidine), known as 3TC, claimed in U.S. Pat. No. 5,539,116 to Liotta, et al., is currently in clinical trials for the treatment of hepatitis B. See also EPA 0 494 119 A1 filed by BioChem Pharma, Inc.

β-2-Hydroxymethyl-5-(5-fluorocytosin-1-yl)-1,3-oxathiolane ("FTC"), claimed in U.S. Pat. Nos. 5,814,639 and 5,914,331 to Liotta et al., exhibits activity against HBV. See Furman et al., "The Anti-Hepatitis B Virus Activities, Cytotoxicities, and Anabolic Profiles of the (-) and (+) Enantiomers of cis-5-Fluoro-1-{2-(Hydroxymethyl)-1,3-oxathiolane-5-yl}-Cytosine" *Antimicrobial Agents and Chemotherapy*, December 1992, page 2686–2692; and Cheng, et al., *Journal of Biological Chemistry*, Volume 267(20), 13938–13942 (1992).

U.S. Pat. Nos. 5,565,438, 5,567,688 and 5,587,362 (Chu, et al.) disclose the use of 2'-fluoro-5-methyl-β-L-arabinofuranolyluridine (L-FMAU) for the treatment of hepatitis B and Epstein Barr virus.

Penciclovir (PCV; 2-amino-1,9-dihydro-9-{4-hydroxy-3-(hydroxymethyl)butyl}-6H-purin-6-one) has established activity against hepatitis B. See U.S. Pat. Nos. 5,075,445 and 5,684,153.

Adefovir (9-{2-(phosphonomethoxy)ethyl}adenine, also referred to as PMEA or {{2-(6-amino-9H-purin-9-yl)ethoxy}methylphosphonic acid), also has established activity against hepatitis B. See, for example, U.S. Pat. Nos. 5,641,763 and 5,142,051.

Yale University and The University of Georgia Research Foundation, Inc. disclose the use of L-FDDC (5-fluoro-3'-thia-2',3'-dideoxycytidine) for the treatment of hepatitis B virus in WO 92/18517.

Other drugs explored for the treatment of HBV include adenosine arabinoside, thymosin, acyclovir, phosphonoformate, zidovudine, (+)-cyanidanol, quinacrine, and 2'-fluoroarabinosyl-5-iodouracil.

U.S. Pat. Nos. 5,444,063 and 5,684,010 to Emory University disclose the use of enantiomerically pure β-D-1,3-dioxolane purine nucleosides to treat hepatitis B.

WO 96/40164 filed by Emory University, UAB Research Foundation, and the Centre National de la Recherche Scientifique (CNRS) discloses a number of β-L-2',3'-dideoxynucleosides for the treatment of hepatitis B.

WO 95/07287 also filed by Emory University, UAB Research Foundation, and the Centre National de la Recherche Scientifique (CNRS) discloses 2' or 3' deoxy and 2',3'-dideoxy-β-L-pentofuranosyl nucleosides for the treatment of HIV infection.

WO96/13512 filed by Genencor International, Inc., and Lipitek, Inc., discloses the preparation of L-ribofuranosyl nucleosides as antitumor agents and virucides.

WO095/32984 discloses lipid esters of nucleoside monophosphates as immuno-suppresive drugs.

DE 4224737 discloses cytosine nucleosides and their pharmaceutical uses.

Tsai et al., in Biochem. Pharmacol. 1994, 48(7), 1477–81, disclose the effect of the anti-HIV agent 2'-β-D-F-2',3'-dideoxynucleoside analogs on the cellular content of mitochondrial DNA and lactate production.

Galvez, J. Chem. Inf. Comput. Sci. 1994, 35(5), 1198–203, describes molecular computation of β-D-3'-azido-2',3'-dideoxy-5-fluorocytidine.

Mahmoudian, Pharm. Research 1991, 8(1), 43–6, discloses quantitative structure-activity relationship analyses of HIV agents such as β-D-3'-azido-2',3'-dideoxy-5-fluorocytidine.

U.S. Pat. No. 5,703,058 discloses (5-carboximido or 5-fluoro)-(2',3'-unsaturated or 3'-modified) pyrimidine nucleosides for the treatment of HIV or HBV.

Lin et al., discloses the synthesis and antiviral activity of various 3'-azido analogues of β-D-nucleosides in J. Med. Chem. 31(2), 336–340 (1988).

WO 00/3998 filed by Novirio Pharmaceuticals, Ltd. discloses methods of preparing substituted 6-benzyl-4-oxopyrimidines, and the use of such pyrimidines for the treatment of HIV.

Novirio Pharmaceuticals, Ltd. was also first to disclose 2'-deoxy-β-L-erythropentofuranonucleosides, and their use in the treatment of HBV in WO 00/09531. A method for the treatment of hepatitis B infection in humans and other host animals is disclosed that includes administering an effective amount of a biologically active 2'-deoxy-β-L-erythropentofuranonucleoside (alternatively referred to as β-L-dN or a β-L-2'-dN) or a pharmaceutically acceptable salt or prodrug thereof, including β-L-deoxyribothymidine (β-L-dT), β-L-deoxyribocytidine (β-L-dC), β-L-deoxyribouridine (β-L-dU), β-L-deoxyribo-guanosine (β-L-dG), β-L-deoxyriboadenosine (β-L-dA) and β-L-deoxyriboinosine (β-L-dI), administered either alone or in combination, optionally in a pharmaceutically acceptable carrier. 5' and $N^4$ (cytidine) or $N^6$ (adenosine) acylated or alkylated derivatives of the active compound, or the 5'-phospholipid or 5'-ether lipids were also disclosed.

Various prodrugs of antivirals have been attempted. Most notably, U.S. Pat. No. 4,957,924 to Beauchamp discloses various therapeutic esters of acyclovir.

In light of the fact that hepatitis B virus has reached epidemic levels worldwide, and has severe and often tragic effects on the infected patient, there remains a strong need to provide new effective pharmaceutical agents to treat humans infected with the virus that have low toxicity to the host.

Therefore, it is an object of the present invention to provide compounds, compositions and methods for the treatment of human patients or other hosts infected with HBV.

SUMMARY OF THE INVENTION

3'-Prodrugs of 2'-deoxy-β-L-nucleosides, or their pharmaceutically acceptable salts or pharmaceutically acceptable formulations containing these compounds are useful in the prevention and treatment of hepatitis B infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

A method for the treatment of a hepatitis B viral infection in a host, including a human, is also disclosed that includes administering an effective amount of a 3'-prodrug of a biologically active 2'-deoxy-β-L-nucleoside or a pharmaceutically acceptable salt thereof, administered either alone or in combination or alternation with another anti-hepatitis B virus agent, optionally in a pharmaceutically acceptable carrier. The term 2'-deoxy, as used in this specification, refers to a nucleoside that has no substituent in the 2'-position. The term 3'-prodrug, as used herein, refers to a 2'-deoxy-β-L-nucleoside that has a biologically cleavable moiety at the 3'-position, including, but not limited to acyl, and in one embodiment, an L-amino acid.

In one embodiment, the 2'-deoxy-β-L-nucleoside 3'-prodrug includes biologically cleavable moieties at the 3' and/or 5' positions. Preferred moieties are amino acid esters including valyl, and alkyl esters including acetyl. Therefore, this invention specifically includes 3'-L-amino acid ester and 3',5'-L-diamino acid ester of 2'-β-L-deoxy nucleosides with any desired purine or pyrimidine base, wherein the parent drug has an $EC_{50}$ of less than 15 micromolar, and preferably less than 10 micromolar in 2.2.15 cells; 3'-(alkyl or aryl ester)- or 3',5'-L-di(alkyl or aryl ester)-2'-β-L-deoxy nucleosides with any desired purine or pyrimidine base, wherein the parent drug has an $EC_{50}$ of less than 10 or 15 micromolar in 2.2.15 cells; and prodrugs of 3',5'-diesters of 2'-deoxy-β-L-nucleosides wherein (i) the 3' ester is an amino acid ester and the 5'-ester is an alkyl or aryl ester; (ii) both esters are amino acid esters; (iii) both esters are independently alkyl or aryl esters; and (iv) the 3' ester is independently an alkyl or aryl ester and the 5'-ester is an amino acid ester, wherein the parent drug has an $EC_{50}$ of less than 10 or 15 micromolar in 2.2.15 cells.

Examples of prodrugs falling within the invention are 3'-L-valine ester of 2'-deoxy-β-L-cytidine; 3'-L-valine ester of 2'-deoxy-β-L-thymine; 3'-L-valine ester of 2'-deoxy-β-L-adenosine; 3'-L-valine ester of 2'-deoxy-β-L-guanosine; 3'-L-valine ester of 2'-deoxy-β-L-5-fluoro-cytidine; 3'-L-valine ester of 2'-deoxy-β-L-uridine; 3'-acetyl ester of 2'-deoxy-β-L-cytidine; 3'-acetyl ester of 2'-deoxy-β-L-thymine; 3'-acetyl ester of 2'-deoxy-β-L-adenosine; 3'-acetyl ester of 2'-deoxy-β-L-guanosine; 3'-acetyl ester of 2'-deoxy-β-L-5-fluoro-cytidine; and 3'-esters of 2'-deoxy-β-L-(cytidine, 5-fluorocytidine, guanosine, uridine, adenosine, or thymine) wherein (i) the 3' ester is an amino acid ester; or (ii) the 3' ester is an alkyl or aryl ester.

Additional examples of prodrugs falling within the invention are 3',5'-L-divaline ester of 2'-deoxy-β-L-cytidine (dival-L-dC); 3',5'-L-divaline ester of 2'-deoxy-β-L-thymine; 3',5'-L-divaline ester of 2'-deoxy-β-L-adenosine; 3',5'-L-divaline ester of 2'-deoxy-β-L-guanosine; 3',5'-L-divaline ester of 2'-deoxy-β-L-5-fluoro-cytidine; 3',5'-L-divaline ester of 2'-deoxy-β-L-uridine; 3',5'-diacetyl ester of 2'-deoxy-β-L-cytidine; 3',5'-diacetyl ester of 2'-deoxy-β-L-thymine; 3',5'-diacetyl ester of 2'-deoxy-β-L-adenosine; 3',5'-diacetyl ester of 2'-deoxy-β-L-guanosine; 3',5'-diacetyl ester of 2'-deoxy-β-L-5-fluoro-cytidine; and 3',5'-diesters of 2'-deoxy-β-L-(cytidine, 5-fluorocytidine, guanosine, uridine, adenosine, or thymine) wherein (i) the 3' ester is an amino acid ester and the 5'-ester is an alkyl or aryl ester; (ii) both esters are amino acid esters; (iii) both esters are independently alkyl or aryl esters; or (iv) the 3' ester is an alkyl or aryl ester and the 5'-ester is an amino acid ester.

In a second embodiment the invention provides the β-L nucleoside 3'-prodrug defined by formula (I):

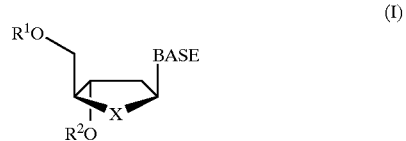

(I)

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

X is O, S, SO$_2$ or CH$_2$; and

BASE is a purine or pyrimidine base that may optionally be substituted.

In a preferred embodiment, X is O.

In one embodiment, R$^1$ and/or R$^2$ are an amino acid residue.

In one embodiment, the amino acid residue is of the formula C(O)C(R$^8$)(R$^9$)(NR$^{10}$R$^{11}$), wherein R$^8$ is the side chain of an amino acid and wherein, as in proline, R$^8$ can optionally be attached to R$^{10}$ to form a ring structure; or alternatively, R$^8$ is an alkyl, aryl, heteroaryl or heterocyclic moiety;

R$^9$ is hydrogen, alkyl (including lower alkyl) or aryl; and

R$^{10}$ and R$^{11}$ are independently hydrogen, acyl (including an acyl derivative attached to R$^8$) or alkyl (including but not limited to methyl, ethyl, propyl, and cyclopropyl).

In another embodiment of the present invention, the β-L nucleoside 3'-prodrug is a β-L-2'-deoxypurine of the formula:

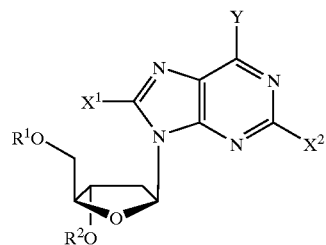

or its pharmaceutically acceptable salt thereof, wherein

R$^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

R$^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is OR$^3$, NR$^3$R$^4$ or SR$^3$; and

X$^1$ and X$^2$ are independently selected from the group consisting of H, straight chained, branched or cyclic alkyl, CO-alkyl, CO-aryl, CO-alkoxyalkyl, halogen, OR$^5$, NR$^5$R$^6$ or SR$^5$; and R$^3$, R$^4$, R$^5$ and R$^6$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In one embodiment, the amino acid residue is of the formula C(O)C(R$^8$)(R$^9$)(NR$^{10}$R$^{11}$), wherein R$^8$ is the side chain of an amino acid and wherein, as in proline, R$^8$ can optionally be attached to R$^{10}$ to form a ring structure; or alternatively, R$^8$ is an alkyl, aryl, heteroaryl or heterocyclic moiety;

R$^9$ is hydrogen, alkyl (including lower alkyl) or aryl; and

R$^{10}$ and R$^{11}$ are independently hydrogen, acyl (including an acyl derivative attached to R$^8$) or alkyl (including but not limited to methyl, ethyl, propyl, and cyclopropyl).

In a particular embodiment, the β-L nucleoside 3'-prodrug is a β-L-2'-deoxyadenosine of the formula:

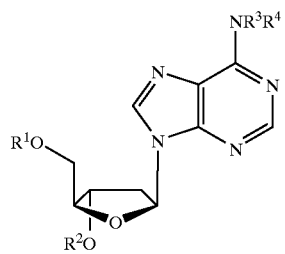

or its pharmaceutically acceptable salt thereof, wherein

R$^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

R$^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and R$^3$ and R$^4$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, R$^1$ is H.

In one embodiment, the amino acid residue is of the formula C(O)C(R$^8$)(R$^9$)(NR$^{10}$R$^{11}$), wherein R$^8$ is the side chain of an amino acid and wherein, as in proline, R$^8$ can optionally be attached to R$^{10}$ to form a ring structure; or alternatively, R$^8$ is an alkyl, aryl, heteroaryl or heterocyclic moiety;

R$^9$ is hydrogen, alkyl (including lower alkyl) or aryl; and

R$^{10}$ and R$^{11}$ are independently hydrogen, acyl (including an acyl derivative attached to R$^8$) or alkyl (including but not limited to methyl, ethyl, propyl, and cyclopropyl).

In another preferred embodiment, R$^2$ is an amino acid residue, and in particular L-valinyl.

In one embodiment, R$^3$ is hydrogen, and R$^4$ is dimethylaminomethylene.

In another embodiment, R$^3$ is hydrogen, and R$^4$ is acetyl.

In another embodiment, R$^3$ is hydrogen, and R$^4$ is L-valinyl.

In another particular embodiment, the β-L nucleoside 3'-prodrug is β-L-2'-deoxyguanosine of the formula:

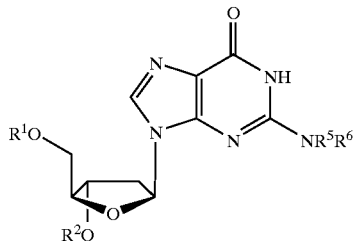

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^5$ and $R^6$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

In one embodiment, $R^5$ is hydrogen, and $R^6$ is dimethylaminomethylene.

In another embodiment, $R^5$ is hydrogen, and $R^6$ is acetyl.

In another embodiment, $R^5$ is hydrogen, and $R^6$ is L-valinyl.

In another particular embodiment, the β-L nucleoside 3'-prodrug is β-L-2'-deoxyinosine or pharmaceutically acceptable salt or prodrug thereof of the formula:

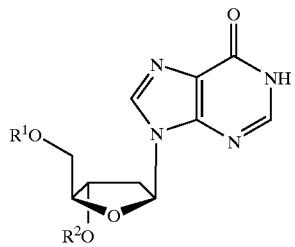

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

In another embodiment of the present invention, the β-L nucleoside 3'-prodrug is β-L-2'-deoxypyrimidine of the formula:

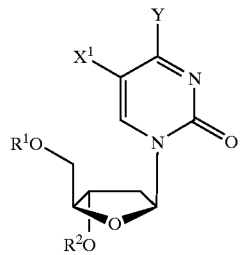

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is $OR^3$, $NR^3R^4$ or $SR^3$;

$X^1$ is selected from the group consisting of H, straight chained, branched or cyclic alkyl, CO-alkyl, CO-aryl, CO-alkoxyalkyl, halogen, $OR^5$, $NR^5R^6$ or $SR^5$; and $R^3$, $R^4$, $R^5$ and $R^6$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In one particular embodiment, the β-L nucleoside 3'-prodrug is β-L-2'-deoxycytidine of the formula:

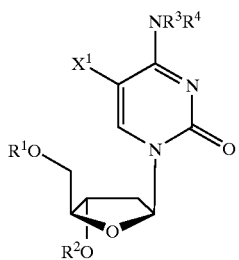

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$X^1$ is selected from the group consisting of H, straight chained, branched or cyclic alkyl, CO-alkyl, CO-aryl, CO-alkoxyalkyl, halogen, $OR^5$, $NR^5R^6$ or $SR^5$; and $R^3$, $R^4$, $R^5$ and $R^6$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In one embodiment, $X^1$ is hydrogen.

In another embodiment, $X^1$ is a halogen, namely fluorine, chlorine, bromine or iodine.

In a preferred embodiment, $R^1$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

In one embodiment, $R^3$ is hydrogen, and $R^4$ is dimethylaminomethylene.

In another embodiment, $R^3$ is hydrogen, and $R^4$ is acetyl.

In another embodiment, $R^3$ is hydrogen, and $R^4$ is L-valinyl.

In another embodiment, the β-L-nucleoside 3'-prodrug is β-L-2'-deoxyuridine of the formula:

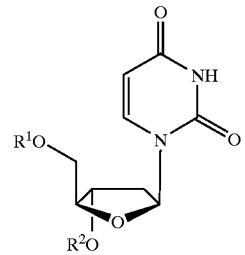

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ is H.

In one embodiment, the amino acid residue is of the formula $C(O)C(R^8)(R^9)(N^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

In another embodiment, the β-L-nucleoside 3'-prodrug is β-L-thymidine of the formula:

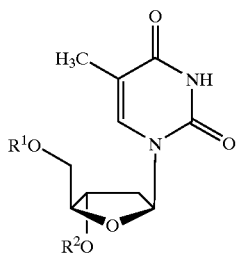

or its pharmaceutically acceptable salt thereof, wherein

R$^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and R$^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, R$^1$ is H.

In one embodiment, the amino acid residue is of the formula C(O)C(R$^8$)(R$^9$)(NR$^{10}$R$^{11}$), wherein R$^8$ is the side chain of an amino acid and wherein, as in proline, R$^8$ can optionally be attached to R$^{10}$ to form a ring structure; or alternatively, R$^8$ is an alkyl, aryl, heteroaryl or heterocyclic moiety;

R$^9$ is hydrogen, alkyl (including lower alkyl) or aryl; and

R$^{10}$ and R$^{11}$ are independently hydrogen, acyl (including an acyl derivative attached to R$^8$) or alkyl (including but not limited to methyl, ethyl, propyl, and cyclopropyl).

In another preferred embodiment, R$^2$ is an amino acid residue, and in particular L-valinyl.

The invention also provides combinations of at least two of the herein described prodrugs.

The invention further provides at least one of the described 3'-prodrugs in combination or alternation with a second nucleoside that exhibits activity against hepatitis B, including but not limited to a parent drug of any of the prodrugs defined herein, i.e. 2'-deoxy-β-L-nucleosides, including 2'-deoxy-β-L-cytidine; 2'-deoxy-β-L-thymine; 2'-deoxy-β-L-adenosine; 2'-deoxy-β-L-guanine; 2'-deoxy-β-L-5-fluorocytidine. Alternatively, the 3'-prodrugs can be administered in combination or alternation with other anti-hepatitis B virus agent such as (−)-cis-2',3'-dideoxy-3'-thiacytidine; cis-2'3'-dideoxy-3'-thia-5-fluorocytidine; L-FMAU; adefovir; famciclovir; and entecivir, or any other compound that exhibits an EC$_{50}$ of less than 10 or 15 micromolar in 2.2.15 cells; or their prodrugs or pharmaceutically acceptable salts.

The invention further includes administering the prodrug in combination or alternation with an immune modulator or other pharmaceutically active modifer of viral replication, including a biological material such as a protein, peptide, oligonucleotide, or gamma globulin, including but not limited to interfereon, interleukin, or an antisense oligonucleotides to genes which express or regulate hepatitis B replication.

The efficacy of the parents of the anti-HBV compound can be measured according to the concentration of compound necessary to reduce the replication rate of the virus in vitro, according to methods set forth more particularly herein, by 50% (i.e. the compound's EC$_{50}$). In preferred embodiments the parent of the prodrug compound exhibits an EC$_{50}$ of less than 15 or preferably, less than 10 micromolar in vitro, when tested in 2.2.15 cells transfected with the hepatitis virion.

BRIEF DESCRIPTION OF THE FIGURES

FIGS. 1a and 1b are non-limiting illustrative examples according to the present invention of the synthesis of 3'- and 5'-valinyl esters of 2'-deoxy-β-L-cytidine (β-L-dC) from 2'-deoxy-β-L-cytidine, respectively.

FIG. 2 is a non-limiting illustrative example according to the present invention of the synthesis of N$^4$-acetyl-2'-deoxy-β-L-cytidine from 2'-deoxy-β-L-cytidine.

FIG. 3 is a non-limiting illustrative example according to the present invention of the synthesis of N$^4$-[(dimethylamino)methylene]-2'-deoxy-β-L-cytidine from 2'-deoxy-β-L-cytidine.

FIG. 4 is a non-limiting illustrative example according to the present invention of the synthesis of 3',5'-di-O-acetyl-2'-deoxy-β-L-cytidine from 2'-deoxy-β-L-cytidine.

FIG. 5 is a non-limiting illustrative example according to the present invention of the synthesis of 3',5'-di-O-valinyl ester of 2'-deoxy-β-L-cytidine from 2'-deoxy-β-L-cytidine.

FIG. 6 is a non-limiting illustrative example according to the present invention of the synthesis of N$^4$-(Boc-valinyl) ester of 2'-deoxy-β-L-cytidine from 2'-deoxy-β-L-cytidine.

FIG. 7 is a non-limiting illustrative example according to the present invention of the synthesis of 3',5',N$^4$-tri-(L-valinyl)-2'-deoxy-β-L-cytidine from 3',5',N$^4$-tri-(Boc-L-valinyl)-2'-deoxy-β-L-cytidine.

FIG. 8 is a line graph depicting a standard calibration technique useful for the determination of solubility of various nucleosides. FIG. 8a is the calibration curve determined for nature β-D-deoxyribocytosine. FIG. 8b is the calibration curve determined for the 3',5'-divalinyl ester of β-L-deoxyribocytosine.

FIG. 9a is a non-limiting example of a HPLC profile used to assess the stability of the 3',5'-divalinyl ester of β-L-deoxyribocytosine at a pH of 7.42. The HPLC profile indicates the presence of the 3',5'-divalinyl ester of β-L-deoxyribocytosine along with 3 active metabolites, the 3'-valinyl ester of β-L-deoxyribocytosine, the 5'-valinyl ester of β-L-deoxyribocytosine and L-dC. FIG. 9b is a line graph depicting the relative concentrations of the 3',5'-divalinyl ester of β-L-deoxyribocytosine and its metabolites over time.

Similarly, FIGS. 10a and 11a are non-limiting examples of HPLC profiles used to assess the stability of the 3',5'-divalinyl ester of β-L-deoxyribocytosine at a pH of 7.20 and 4.51, respectively. At these pH's, the HPLC profile indicates the presence of the 3',5'-divalinyl ester of β-L-deoxyribocytosine along with 3 active metabolites, the 3'-valinyl ester of β-L-deoxyribocytosine, the 5'-valinyl ester of β-L-deoxyribocytosine and L-dC. FIGS. 10b and 11b are line graphs depicting the relative concentrations of the 3',5'-divalinyl ester of β-L-deoxyribocytosine and its metabolites over time.

FIG. 12 is a non-limiting example of a HPLC profile used to assess the stability of the 3',5'-divalinyl ester of β-L-deoxyribocytosine at a pH of 1.23. At this pH, the HPLC profile only indicates the presence of the 3',5'-divalinyl ester of β-L-deoxyribocytosine without any decomposition into any of its 3 active metabolites.

FIG. 13 is a line graph depicting the in vitro metabolism of 3',5'-divalinyl ester of β-L-deoxyribocytosine in human plasma.

FIG. 14 is a line graph depicting the intracellular metabolism of β-L-deoxyribocytosine (L-dC) in HepG2 cells.

FIG. 15 is a line graph depicting the intracellular accumulation of L-dC in primary human hepatocytes.

FIG. 16 is a bar graph depicting the antiviral dose response of L-dC upon treatment of a chronic hepatitis B virus infection for 28 days in the woodchuck model of chronic Hepatitis B virus infection.

FIG. 17 is a line graph depicting the antiviral activity of L-dC in the woodchuck model of chronic hepatitis B virus infection.

FIG. 18 are line graphs indicating the body weights of individual woodchucks treated for 28 days with L-dC (0.01–10 mg/kg/day) orally.

FIG. 19 are line graphs indicating the body weights of individual woodchucks treated for 12 Weeks with L-dC (1 mg/kg/day) orally.

DETAILED DESCRITPTION OF THE INVENTION

The invention as disclosed herein is a compound, a method and composition for the treatment of hepatitis B virus in humans and other host animals. The method includes the administration of an effective HBV treatment amount of a 3'-prodrug of a β-L-nucleoside as described herein or a pharmaceutically acceptable salt thereof, optionally in a pharmaceutically acceptable carrier. The compound of this invention either possesses antiviral (i.e., anti-HBV) activity, or is metabolized to a compound that exhibits such activity.

In summary, the present invention includes the following features:

(a) β-L-2'-deoxy-nucleoside 3'-prodrugs, as described herein, and pharmaceutically acceptable salts, esters and compositions thereof;

(b) β-L-2'-deoxy-nucleoside 3'-prodrugs as described herein, and pharmaceutically acceptable salts, esters and compositions thereof for use in the treatment or prophylaxis of a hepatitis B infection, especially in individuals diagnosed as having a hepatitis B infection or being at risk of becoming infected by hepatitis B;

(c) use of these β-L-2'-deoxy-nucleoside 3'-prodrugs, and pharmaceutically acceptable salts, esters and compositions thereof in the manufacture of a medicament for treatment of a hepatitis B infection;

(d) pharmaceutical formulations comprising the β-L-2'-deoxy-nucleoside 3'-prodrugs or pharmaceutically acceptable salts thereof together with a pharmaceutically acceptable carrier or diluent;

(e) β-L-2'-deoxy-nucleoside 3'-prodrugs, or their pharmaceutically acceptable salts, esters and compositions as described herein substantially in the absence of the opposite enantiomers of the described nucleoside, or substantially isolated from other chemical entities;

(f) processes for the preparation of β-L-2'-deoxy-nucleoside 3'-prodrugs, as described in more detail below;

(g) processes for the preparation of β-L-2'-deoxy-nucleoside 3'-prodrugs substantially in the absence of enantiomers of the described nucleoside, or substantially isolated from other chemical entities;

(h) the treatment of a host infected with hepatitis B that includes the administration of an effective amount of a 3'-prodrug of a β-L-2'-deoxy-nucleoside, its pharmaceutically acceptable salt, ester or composition with a second anti-hepatitis B agent;

(i) the treatment of a host infected with hepatitis B that includes the administration of an effective amount of a 3'-prodrug of a β-L-2'-deoxy-nucleoside, its pharmaceutically acceptable salt, ester or composition with the parent of a different β-L-2'-deoxynucleoside;

(j) the treatment of a host infected with hepatitis B that includes the administration of an effective amount of a 3'-prodrug of a β-L-2'-deoxy-cytidine, its pharmaceutically acceptable salt or ester with the parent of a second anti-hepatitis B agent;

(k) the treatment of a host infected with hepatitis B that includes the administration of an effective amount of the 3',5'-divalyl or diacetyl ester of β-L-2'-deoxy-cytidine, or its pharmaceutically acceptable salt or ester thereof, with a second anti-hepatitis B agent; and (l) the treatment of a host infected with hepatitis B that includes the administration of an effective amount of the 3',5'-divalyl or diacetyl ester of β-L-2'-deoxy-cytidine, or its pharmaceutically acceptable salt or ester thereof, with β-L-2'-deoxy-thymidine, or its pharmaceutically acceptable salt.

A particularly preferred combination is the 3',5'-prodrug of β-L-dC (also referred to as L-dC) with the parent β-L-dT (also referred to as L-dT), and in particular, the 3',5'-divalyl or 3',5'-diacetyl ester of β-L-dC in combination with β-L-dT. The oral bio-availability of L-dC as the neutral base and the HCl salt is low in rodents and non-human primates. It has been discovered that there is significant competition of L-dC with other nucleosides or nucleoside analogs for absorption, or transport, from the gastrointestinal tract and competition of other nucleosides or nucleoside analogs for the absorption with L-dC. In order to improve oral bioavailability and reduce the potential for drug-drug interaction, a pharmacokinetic screen in monkeys was established. This screen identified 3'-prodrugs of L-dC that had higher oral bioavailability than the parent molecule and a reduced effect on the bioavailability of other nucleosides or nucleoside analogs used in combination. Examples of such nucleo sides or nucleo side analogs used in combination with the prodrugs of L-dC are L-dT, L-dA, lamivudine or FTC.

It was discovered using this approach, that the 3',5'-divaline ester of L-dC had higher oral bioavailability than the parent L-dC and a reduced interaction with other nucleosides or nucleoside analogs when used in combination as compared to L-dC. Pharmacokinetic studies also showed that the 3',5'-divaline ester of L-dC was converted to the parent L-dC through de-esterification in the gastrointestinal mucosa, blood or liver.

The 3',5'-divaline ester of L-dC is apparently actively transported from the gastrointestinal lumen after oral delivery into the bloodstream by an amino acid transporter function in the mucosa of the gastrointestinal tract. This accounts for the increase in oral bioavailability compared to the parent L-dC that would be transported primarily by a nucleoside transporter function. It would also explain the reduced competition for uptake of the 3',5'-divaline ester of L-dC with other nucleosides or nucleoside analogs that are transported by the nucleoside transporter finction and not the amino acid transporter function. As partial de-esterification of the divaline ester of L-dC occurs prior to complete absorption, the monovaline ester continues to be absorbed using the amino acid transporter function. Therefore, the desired outcome of better absorption, or bioavailability, and reduced competition with other nucleosides or nucleoside analogs for uptake into the bloodstream is maintained.

I. Compounds Defined by this Invention

In a first embodiment, the 2'-deoxy-β-L-nucleoside 3'-prodrug includes biologically cleavable moieties at both the 3' and 5' positions. Preferred moieties are L-amino acid esters such as L-valyl, and alkyl esters such as acetyl. This invention specifically includes 3',5'-L-amino acid-β-L-2'-deoxy nucleosides with any desired purine or pyrimidine base, wherein the parent drug has an $EC_{50}$ of less than 15 micromolar, and preferably less than 10 micromolar, in 2.2.15 cells; 3',5'-(alkyl or aryl)-β-L-2'-deoxy nucleosides with any desired purine or pyrimidine base, wherein the parent drug has an $EC_{50}$ of less than 15, and preferably less than 10 micromolar in 2.2.15 cells; and prodrugs of 3',5'-diesters of 2'-deoxy-β-L-nucleosides wherein (i) the 3' ester is an amino acid ester and the 5'-ester is an alkyl or aryl ester; (ii) both esters are amino acid esters, (iii) both esters are independently alkyl or aryl esters, and (iv) the 3' ester is independently an alkyl or aryl ester and the 5'-ester is an amino acid ester, wherein the parent drug has an $EC_{50}$ on dosing of less than 15 micromolar in 2.2.15 cells;

Examples of 3'-prodrugs falling within the invention are 3',5'-L-valine ester of 2'-deoxy-β-L-cytidine; 3',5'-L-valine ester of 2'-deoxy-β-L-thymine; 3',5'-L-valine ester of 2'-deoxy-β-L-adenosine; 3',5'-L-valine ester of 2'-deoxy-β-L-guanosine; 3',5'-L-valine ester of 2'-deoxy-β-L-5-fluoro-cytidine; 3',5'-L-valine ester of 2-deoxy-β-L-uridine; 3',5'-acetyl ester of 2'-deoxy-β-L-cytidine; 3',5'-acetyl ester of 2'-deoxy-β-L-thymine; 3',5'-acetyl ester of 2'-deoxy-β-L-adenosine; 3',5'-acetyl ester of 2'-deoxy-β-L-guanosine; 3',5'-acetyl ester of 2'-deoxy-β-L-5-fluoro-cytidine; and 3',5'-diesters of 2'-deoxy-β-L-(cytidine, 5-fluorocytidine, guanosine, uridine, adenosine, or thymine) wherein (i) the 3' ester is an amino acid ester and the 5'-ester is an alkyl or aryl ester; (ii) both esters are amino acid esters, (iii) both esters are independently alkyl or aryl esters or (iv) the 3' ester is an alkyl or aryl ester and the 5'-ester is an amino acid ester.

In one embodiment, the invention provides the β-L nucleoside 3'-prodrug defined by formula (I):

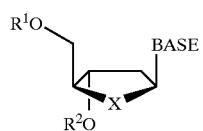

(I)

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

X is O, S, $SO_2$ or $CH_2$; and

BASE is a purine or pyrimidine base that may optionally be substituted.

In a preferred embodiment, X is O.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In a first subembodiment $R^2$ is C(O)-alkyl (including lower alkyl) or aryl, and BASE is adenine, protected adenine, cytosine, protected cytosine or thymine.

In a second subembodiment $R^2$ is C(O)-lower alkyl and BASE is adenine, protected adenine, cytosine, protected cytosine or thymine.

In a third subembodiment $R^2$ is C(O)-methyl and BASE is adenine, protected adenine, cytosine, protected cytosine or thymine.

In a fourth subembodiment $R^2$ is $C(O)C(R^8)(H)(NR^{10}R^{11})$, and BASE is adenine, protected adenine, cytosine, protected cytosine or thymine.

In a fifth subembodiment $R^2$ is $C(O)C(R^8)(H)(NR^{10}R^{11})$, $R^8$ is isopropyl, at least one of $R^{10}$ and $R^{11}$ is hydrogen, and BASE is adenine, protected adenine, cytosine, protected cytosine or thymine.

In a sixth subembodiment $R^2$ is $C(O)C(R^8)(H)(NR^{10}R^{11})$, $R^8$ is an amino acid side chain, and BASE is adenine, protected adenine, cytosine, protected cytosine, or thymine.

In a seventh subembodiment $R^2$ is $C(O)C(R^8)(H)(NR^{10}R^{11})$; $R^8$ is a nonpolar amino acid side chain and BASE is adenine, protected adenine, cytosine, protected cytosine or thymine.

Nonlimiting examples of subembodiments can be defined by formula (I) in which:

(1) $R^2$ is C(O)-methyl and BASE is adenine.
(2) $R^2$ is C(O)-methyl and BASE is protected adenine.
(3) $R^2$ is C(O)-methyl and BASE is cytosine.
(4) $R^2$ is C(O)-methyl and BASE is protected cytosine.
(5) $R^2$ is C(O)-methyl and BASE is thymine.
(6) $R^2$ is $C(O)C(R^8)(H)(NH_2)$; $R^8$ is isopropyl and BASE is adenine.
(7) $R^2$ is $C(O)C(R^8)(H)(NH_2)$; $R^8$ is isopropyl and BASE is protected adenine.
(8) $R^2$ is $C(O)C(R^8)(H)(NH_2)$; $R^8$ is isopropyl and BASE is cytosine.
(9) $R^2$ is $C(O)C(R^8)(H)(NH_2)$; $R^8$ is isopropyl and BASE is protected cytosine.
(10) $R^2$ is $C(O)C(R^8)(H)(NH_2)$; $R^8$ is isopropyl and BASE is thymine.

In a eighth subembodiment X is O, $R^2$ is C(O)-alkyl (including lower alkyl) or aryl, and BASE is adenine, protected adenine, cytosine, protected cytosine, or thymine.

In a ninth subembodiment X is O, $R^2$ is C(O)-lower alkyl and BASE is adenine, protected adenine, cytosine, protected cytosine or thymine.

In a tenth subembodiment X is O, $R^2$ is C(O)-methyl and BASE is adenine, protected adenine, cytosine, protected cytosine or thymine.

In an eleventh subembodiment X is O, $R^2$ is $C(O)C(R^8)(H)(NR^{10}R^{11})$, and BASE is adenine, protected adenine, cytosine, protected cytosine or thymine.

In a twelfth subembodiment X is O, $R^2$ is $C(O)C(R^8)(H)(NR^{10}R^{11})$, $R^8$ is isopropyl, at least one of $R^{10}$ and $R^{11}$ is hydrogen, and BASE is adenine, protected adenine, cytosine, protected cytosine or thymine.

In a thirteenth subembodiment X is O, $R^2$ is $C(O)C(R^8)(H)(NR^{10}R^{11})$, $R^8$ is an amino acid side chain, and BASE is adenine, protected adenine, cytosine, protected cytosine, or thymine.

In a fourteenth subembodiment X is O, $R^2$ is $C(O)C(R^8)(H)(NR^{10}R^{11})$; $R^8$ is a nonpolar amino acid side chain; at least one of $R^5$ and $R^6$ is hydrogen and B is adenine, protected adenine, cytosine, protected cytosine or thymine.

Nonlimiting examples of subembodiments can be defined by formula (I) in which:

(1) X is O, $R^2$ is C(O)-methyl and BASE is adenine.
(2) X is O, $R^2$ is C(O)-methyl and BASE is protected adenine.
(3) X is O, $R^2$ is C(O)-methyl and BASE is cytosine.
(4) X is O, $R^2$ is C(O)-methyl and BASE is protected cytosine.
(5) X is O, $R^2$ is C(O)-methyl and BASE is thymine.
(6) X is O, $R^2$ is $C(O)C(R^8)(H)(NH_2)$; $R^8$ is isopropyl and BASE is adenine.
(7) X is O, $R^2$ is $C(O)C(R^8)(H)(NH_2)$; $R^8$ is isopropyl and BASE is protected adenine.
(8) X is O, $R^2$ is $C(O)C(R^8)(H)(NH_2)$; $R^8$ is isopropyl and BASE is cytosine.
(9) X is O, $R^2$ is $C(O)C(R^8)(H)(NH_2)$; $R^8$ is isopropyl and BASE is protected cytosine.
(10) X is O, $R^2$ is $C(O)C(R^8)(H)(NH_2)$; $R^8$ is isopropyl and BASE is thymine.

In a fifteenth subembodiment X is O, $R^1$ is hydrogen, $R^2$ is C(O)-alkyl (including lower alkyl) or aryl, and BASE is adenine, protected adenine, cytosine, protected cytosine, or thymine.

In a sixteenth subembodiment X is O, $R^1$ is hydrogen, $R^2$ is C(O)-lower alkyl and BASE is adenine, protected adenine, cytosine, protected cytosine or thymine.

In a seventeenth subembodiment X is O, $R^1$ is hydrogen, $R^2$ is C(O)-methyl and BASE is adenine, protected adenine, cytosine, protected cytosine or thymine.

In a eighteenth subembodiment X is O, $R^1$ is hydrogen, $R^2$ is $C(O)C(R^8)(H)(NR^{10}R^{11})$, and BASE is adenine, protected adenine, cytosine, protected cytosine or thymine.

In a nineteenth subembodiment X is O, $R^1$ is hydrogen, $R^2$ is $C(O)C(R^8)(H)(NR^{10}R^{11})$, $R^8$ is isopropyl, at least one of $R^{10}$ and $R^{11}$ is hydrogen, and BASE is adenine, protected adenine, cytosine, protected cytosine or thymine.

In a twentieth subembodiment X is O, $R^1$ is hydrogen, $R^2$ is $C(O)C(R^8)(H)(NR^{10}R^{11})$, $R^8$ is an amino acid side chain, and BASE is adenine, protected adenine, cytosine, protected cytosine, or thymine.

In a twenty-first subembodiment X is O, $R^1$ is hydrogen, $R^2$ is $C(O)C(R^8)(H)(N^{10}R^{11})$; $R^8$ is a nonpolar amino acid side chain; at least one of $R^5$ and $R^6$ is hydrogen and B is adenine, protected adenine, cytosine, protected cytosine or thymine.

Nonlimiting examples of subembodiments can be defined by formula (I) in which:

(1) X is O, $R^1$ is hydrogen, $R^2$ is C(O)-methyl and BASE is adenine.
(2) X is O, $R^1$ is hydrogen, $R^2$ is C(O)-methyl and BASE is protected adenine.
(3) X is O, $R^1$ is hydrogen, $R^2$ is C(O)-methyl and BASE is cytosine.
(4) X is O, $R^1$ is hydrogen, $R^2$ is C(O)-methyl and BASE is protected cytosine.
(5) X is O, $R^1$ is hydrogen, $R^2$ is C(O)-methyl and BASE is thymine.
(6) X is O, $R^1$ is hydrogen, $R^2$ is $C(O)C(R^8)(H)(NH_2)$; $R^8$ is isopropyl and BASE is adenine.
(7) X is O, $R^1$ is hydrogen, $R^2$ is $C(O)C(R^8)(H)(NH_2)$; $R^8$ is isopropyl and BASE is protected adenine.
(8) X is O, $R^1$ is hydrogen, $R^2$ is $C(O)C(R^8)(H)(NH_2)$; $R^8$ is isopropyl and BASE is cytosine.
(9) X is O, $R^1$ is hydrogen, $R^2$ is $C(O)C(R^8)(H)(NH_2)$; $R^8$ is isopropyl and BASE is protected cytosine.
(10) X is O, $R^1$ is hydrogen, $R^2$ is $C(O)C(R^8)(H)(NH_2)$; $R^8$ is isopropyl and BASE is thymine.

In a twenty-second subembodiment X is O, $R^1$ and $R^2$ are independently C(O)-alkyl (including lower alkyl) or aryl, and BASE is adenine, protected adenine, cytosine, protected cytosine, or thymine.

In a twenty-third subembodiment X is O, $R^1$ and $R^2$ are independently C(O)-lower alkyl and BASE is adenine, protected adenine, cytosine, protected cytosine or thymine.

In a twenty-fourth subembodiment X is O, $R^1$ and $R^2$ are independently C(O)-methyl and BASE is adenine, protected adenine, cytosine, protected cytosine or thymine.

In a twenty-fifth subembodiment X is O, $R^1$ and $R^2$ are independently $C(O)C(R^8)(H)(NR^{10}R^{11})$, and BASE is adenine, protected adenine, cytosine, protected cytosine or thymine.

In a twenty-sixth subembodiment X is O, $R^1$ and $R^2$ are independently $C(O)C(R^8)(H)(N^{10}R^{11})$, $R^8$ is isopropyl, at least one of $R^{10}$ and $R^{11}$ is hydrogen, and BASE is adenine, protected adenine, cytosine, protected cytosine or thymine.

In a twenty-seventh subembodiment X is O, $R^1$ and $R^2$ are independently $C(O)C(R^8)(H)(NR^{10}R^{11})$, $R^8$ is an amino acid side chain, and BASE is adenine, protected adenine, cytosine, protected cytosine, or thymine.

In a twenty-eighth subembodiment X is O, $R^1$ and $R^2$ are independently $C(O)C(R^8)(H)(NR^{10}R^{11})$; $R^8$ is a nonpolar amino acid side chain; at least one of $R^5$ and $R^6$ is hydrogen and B is adenine, protected adenine, cytosine, protected cytosine or thymine.

Nonlimiting examples of subembodiments can be defined by formula (I) in which:

(1) X is O, $R^1$ and $R^2$ are independently C(O)-methyl and BASE is adenine.
(2) X is O, $R^1$ and $R^2$ are independently C(O)-methyl and BASE is protected adenine.
(3) X is O, $R^1$ and $R^2$ are independently C(O)-methyl and BASE is cytosine.
(4) X is O, $R^1$ and $R^2$ are independently C(O)-methyl and BASE is protected cytosine.
(5) X is O, $R^1$ and $R^2$ are independently C(O)-methyl and BASE is thymine.
(6) X is O, $R^1$ and $R^2$ are independently $C(O)C(R^8)(H)(NH_2)$; $R^8$ is isopropyl and BASE is adenine.
(7) X is O, $R^1$ and $R^2$ are independently $C(O)C(R^8)(H)(NH_2)$; $R^8$ is isopropyl and BASE is protected adenine.
(8) X is O, $R^1$ and $R^2$ are independently $C(O)C(R^8)(H)(NH_2)$; $R^8$ is isopropyl and BASE is cytosine.
(9) X is O, $R^1$ and $R^2$ are independently $C(O)C(R^8)(H)(NH_2)$; $R^8$ is isopropyl and BASE is protected cytosine.
(10) X is O, $R^1$ and $R^2$ are independently $C(O)C(R^8)(H)(NH_2)$; $R^8$ is isopropyl and BASE is thymine.

In another embodiment of the present invention, the β-L nucleoside 3'-prodrug is a β-L-2'-deoxypurine of the formula:

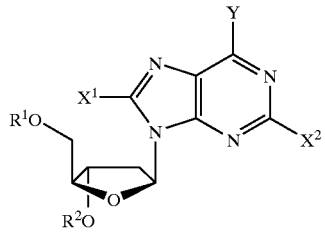

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

Y is $OR^3$, $NR^3R^4$ or $SR^3$; and $X^1$ and $X^2$ are independently selected from the group consisting of H, straight chained, branched or cyclic alkyl, CO-alkyl, CO-aryl, CO-alkoxyalkyl, halogen, $OR^5$, $NR^5R^6$ or $SR^5$; and $R^3$, $R^4$, $R^5$ and $R^6$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In a particular embodiment, the β-L nucleoside 3'-prodrug is a β-L-2'-deoxyadenosine of the formula:

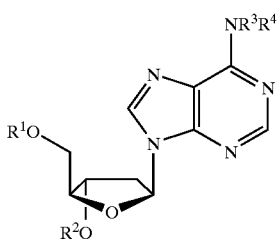

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^3$ and $R^4$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

In one embodiment, $R^3$ is hydrogen, and $R^4$ is dimethylaminomethylene.

In another embodiment, $R^3$ is hydrogen, and $R^4$ is acetyl.

In another embodiment, $R^3$ is hydrogen, and $R^4$ is L-valinyl.

In another particular embodiment, the β-L nucleoside 3'-prodrag is β-L-2'-deoxyguanosine of the formula:

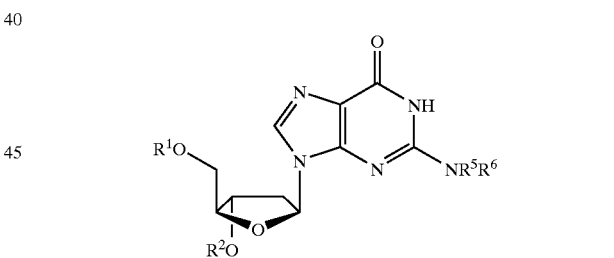

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^5$ and $R^6$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;
$R^9$ is hydrogen, alkyl (including lower alkyl) or aryl; and
$R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

In one embodiment, $R^5$ is hydrogen, and $R^6$ is dimethylaminomethylene.

In another embodiment, $R^5$ is hydrogen, and $R^6$ is acetyl.

In another embodiment, $R^5$ is hydrogen, and $R^6$ is L-valinyl.

In another particular embodiment, the β-L nucleoside 3'-prodrug is β-L-2'-deoxyinosine or pharmaceutically acceptable salt or prodrug thereof of the formula:

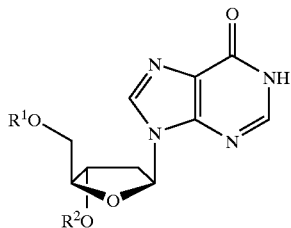

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and
$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;
$R^9$ is hydrogen, alkyl (including lower alkyl) or aryl; and
$R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

In another embodiment of the present invention, the β-L nucleoside 3'-prodrug is β-L-2'-deoxypyrimidine of the formula:

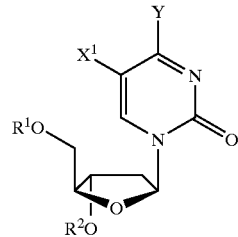

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;
$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;
Y is $OR^3$, $NR^3R^4$ or $SR^3$;
$X^1$ is selected from the group consisting of H, straight chained, branched or cyclic alkyl, CO-alkyl, CO-aryl, CO-alkoxyalkyl, halogen, $OR^5$, $NR^5R^6$ or $SR^5$; and
$R^3$, $R^4$, $R^5$ and $R^6$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;
$R^9$ is hydrogen, alkyl (including lower alkyl) or aryl; and
$R^{10}$ and $R^{11}$ are independently hydrogen, acyl (including an acyl derivative attached to $R^8$) or alkyl (including but not limited to methyl, ethyl, propyl, and cyclopropyl).

In one particular embodiment, the β-L nucleoside 3'-prodrug is β-L-2'-deoxycytidine of the formula:

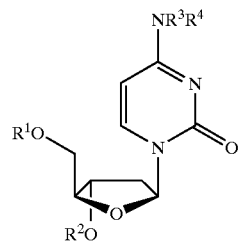

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative;

$R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^3$ and $R^4$ are independently H, straight chained, branched or cyclic alkyl (especially cyclopropyl), dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

In one embodiment, $R^3$ is hydrogen, and $R^4$ is dimethylaminomethylene.

In another embodiment, $R^3$ is hydrogen, and $R^4$ is acetyl.

In another embodiment, $R^3$ is hydrogen, and $R^4$ is L-valinyl.

In another embodiment, the β-L-nucleoside 3'-prodrug is β-L-2'-deoxyuridine of the formula:

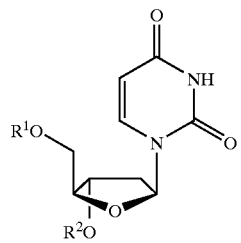

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

In another embodiment, the β-L-nucleoside 3'-prodrug is β-L-thymidine of the formula:

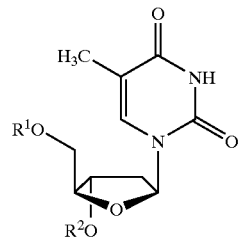

or its pharmaceutically acceptable salt thereof, wherein $R^1$ is hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and $R^2$ is selected from the group consisting of straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative.

In a preferred embodiment, $R^1$ is H.

In one embodiment, the amino acid residue is of the formula $C(O)C(R^8)(R^9)(NR^{10}R^{11})$, wherein $R^8$ is the side chain of an amino acid and wherein, as in proline, $R^8$ can optionally be attached to $R^{10}$ to form a ring structure; or alternatively, $R^8$ is an alkyl, aryl, heteroaryl or heterocyclic moiety;

$R^9$ is hydrogen, alkyl (including lower alkyl) or aryl; and $R^{10}$ and $R^{11}$ are independently hydrogen, acyl (including an acyl derivative attached to $R^8$) or alkyl (including but not limited to methyl, ethyl, propyl, and cyclopropyl).

In another preferred embodiment, $R^2$ is an amino acid residue, and in particular L-valinyl.

II. Definitions and Use of Terms

The term alkyl, as used herein, unless otherwise specified, refers to a saturated straight, branched, or cyclic, primary, secondary, or tertiary hydrocarbon of $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al.,

*Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. Non-limiting examples of protecting groups are taught in Greene, et al., *Protective Groups in Organic Synthesis*, John Wiley and Sons, Second Edition, 1991.

The term aryl, as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term amino acid includes naturally occurring and synthetic $\alpha,\beta$ $\gamma$ or $\delta$ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The term heteroaryl or heteroaromatic, as used herein, refers to an aromatic moiety that includes at least one sulfur, oxygen, nitrogen or phosphorus in the aromatic ring. The term heterocyclic refers to a nonaromatic cyclic group wherein there is at least one heteroatom, such as oxygen, sulfur, nitrogen or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkylpyrimidines, N5-benzylpyrimidines, N5-halopyrimidines, N5-vinylpyrimidine, N5-acetylenic pyrimidine, N5-acyl pyrimidine, N5-hydroxyalkyl purine, and N6-thioalkyl purine, and isoxazolyl. The heteroaromatic and heterocyclic moieties can be optionally substituted as described above for aryl, including substituted with one or more substituent selected from halogen, haloalkyl, alkyl, alkoxy, hydroxy, carboxyl derivatives, amido, amino, alkylamino, dialkylamino. The hetero-aromatic can be partially or totally hydrogenated as desired. As a nonlimiting example, dihydropyridine can be used in place of pyridine. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl.

As used herein, the term "substantially free of enantiomer" or "substantially in the absence of enantiomer" refers to a nucleoside composition that includes at least 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85% or 90% by weight, preferably 95% to 98% by weight, and even more preferably 99% to 100% by weight, of the nucleoside, the remainder comprising other chemical species or enantiomers.

The term "independently" is used herein to indicate that the variable that is independently applied varies independently from application to application. Thus, in a compound such as R"XYR", wherein R" is "independently carbon or nitrogen," both R" can be carbon, both R" can be nitrogen, or one R" can be carbon and the other R" nitrogen.

The term host, as used herein, refers to a unicellular or multicellular organism in which the virus can replicate, including cell lines and animals, and preferably a human. Alternatively, the host can be carrying a part of the hepatitis B viral genome, whose replication or function can be altered by the compounds of the present invention. The term host specifically refers to infected cells, cells transfected with all or part of the HBV genome and animals, in particular, primates (including chimpanzees) and humans. In most animal applications of the present invention, the host is a human patient. Veterinary applications, in certain indications, however, are clearly anticipated by the present invention (such as chimpanzees).

The terms "pharmaceutically acceptable salts" and "pharmaceutically acceptable complexes" are used throughout the specification to describe any pharmaceutically acceptable form of a nucleoside compound, which, upon administration to a patient, provides the nucleoside compound and exhibit minimal, if any, undesired toxicological effects. Pharmaceutically acceptable salts include those derived from pharmaceutically acceptable inorganic or organic bases and acids. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as those derived from alkali metals, those derived from alkaline earth metals, sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against HBV, or are metabolized to a compound that exhibits such activity.

III. Nucleotide Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, sulfate, nitrate, bicarbonate and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides to achieve a desired effect.

The active β-L-3'-prodrug nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythyrnidine diphosphate dimyristoylglycerol, a lipid prodrug of 3,-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No.

5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

The 3'-prodrug can be administered as any derivative that upon administration to the recipient, is capable of providing directly or indirectly, the 3'-prodrug of the parent compound or that exhibits activity itself. Nonlimiting examples are the pharmaceutically acceptable salts (alternatively referred to as "physiologically acceptable salts"), and the $N^4$ pyrimidine or $N^2$ and/or $N^6$-purine alkylated (in particular with dimethylaminomethylene) or acylated (in particular with acetyl or aminoacetyl) derivatives of the active compound. In one nonlimiting embodiment, the acyl group is a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, phosphate, including but not limited to mono, di or triphosphate ester, trityl or monomethoxytrityl, substituted benzyl, trialkylsilyl (e.g., dimethyl-5-butylsilyl) or diphenylmethylsilyl. Aryl groups in the esters optionally comprise a phenyl group.

Modifications of the 3'-prodrug or parent compound, and especially at the $N^4$ pyrimidinyl; or $N^2$ and/or $N^6$ purine positions, can affect the bioavailability and rate of metabolism of the active species, thus providing control over the delivery of the active species. Further, the modifications can affect that antiviral activity of the compound, in some cases increasing the activity over the parent compound. This can easily be assessed by preparing the derivative and testing its antiviral activity according to the methods described herein, or other method known to those skilled in the art.

IV. Stereochemistry

Since the 1' and 4' carbons of the sugar (referred to herein generically as the sugar moiety) of the nucleosides are chiral, their nonhydrogen substituents (CH$_2$OR and the pyrimidine or purine base, respectively) can be either cis (on the same side) or trans (on opposite sides) with respect to the sugar ring system. The four optical isomers therefore are represented by the following configurations (when orienting the sugar moiety in a horizontal plane such that the "primary" oxygen (that between the C1' and C4'-atoms is in back): "β" or "cis" (with both groups "up", which corresponds to the configuration of naturally occurring nucleosides, i.e., the D configuration), "β" or cis (with both groups "down", which is a nonnaturally occurring configuration, i.e., the L configuration), "α" or "trans" (with the C2 substituent "up" and the C5 substituent "down"), and "α" or trans (with the C2 substituent "down" and the C5 substituent "up").

The nucleosides of the present invention are of the β-L-configuration. In a preferred embodiment, the 2'-deoxy-β-L-nucleoside is administered substantially in the form of a single isomer, i.e., at least approximately 95% in the designated stereoconfiguration.

V. Combination and Alternation Therapy

In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

For example, in any of the embodiments described herein, if the 3'-prodrug of the β-L-2'-deoxynucleoside of the present invention is administered in combination or alternation with a second nucleoside or nonnucleoside reverse transcriptase inhibitor that is phosphorylated to an active form, in one embodiment, a second compound is one that can be phosphorylated by an enzyme that is different from that which phosphorylates the selected β-L-2'-nucleoside of the present invention in vivo. Examples of kinase enzymes are thymidine kinase, cytosine kinase, guanosine kinase, adenosine kinase, deoxycytidine kinase, 5'-nucleotidase and deoxy-guanosine kinase.

Thus, in one embodiment the invention provides a combination of two or more nucleoside prodrugs of the present invention, preferably nucleosides that are phosphorylated by distinct enzymes, or that act through distinct biological pathways. In another embodiment the invention provides at least one prodrug in combination or alternation with a nucleoside that exhibits activity against hepatitis B, including but not limited to a parent drug of any of the prodrugs defined herein, i.e. 2'-deoxy-β-L-nucleosides, including 2'-deoxy-β-L-cytidine; 2'-deoxy-β-L-thymine; 2'-deoxy-β-L-adenosine; 2'-deoxy-β-L-guanine; 2'-deoxy-β-L-5-fluorocytidine; 2',3'-dideoxy-3'-thiacytidine; 2',3'-dideoxy-3-thia-5-fluorocytidine. Alternatively, the compounds of the present invention can also be administered in combination or alternation with any other known anti-hepatits B virus agent, such as entecivir, cis-2-hydroxymethyl-5-(5-fluorocytosin-1-yl)-1,3-oxathiolane, preferably substantially in the form of the (−)-optical isomer ("FTC", see WO 92/14743); the (−)-enantiomer of cis-2-hydroxymethyl-5-(cytosin-1-yl)-1, 3-oxathiolane (3TC); β-D-1,3-dioxolane purine nucleosides as described in U.S. Pat. Nos. 5,444,063 and 5,684,010; βD-dioxolane nucleosides such as β-D-dioxolanyl-guanine (DXG), β-D-dioxolanyl-2,6-diaminopurine (DAPD), and β-D-dioxolanyl-6-chloropurine (ACP), L-FDDC (5-fluoro-3'-thia-2',3'-dideoxycytidine), L-enantiomers of 3'-fluoro-modified β-2'-deoxyribonucleoside 5'-triphosphates, carbovir, interferon, penciclovir and famciclovir, L-FMAU, famciclovir, penciclovir, BMS-200475, bis pom PMEA (adefovir, dipivoxil); lobucavir, ganciclovir, or ribavarin; or any other compound that exhibits an EC$_{50}$ of less than 15 micromolar in 2.2.15 cells; or their prodrugs or pharmaceutically acceptable salts.

Combination and alternation therapy can also be undertaken to combat drug resistance. It has been recognized that drug-resistant variants of viruses can emerge after prolonged treatment with an antiviral agent. Drug resistance most typically occurs by mutation of a gene that encodes for an enzyme used in viral replication. The efficacy of a drug against hepatitis B infection can be prolonged, augmented, or restored by administering the compound in combination or alternation with a second, and perhaps third, antiviral compound that induces a different mutation from that caused by the principle drug. Alternatively, the pharnacokinetics, biodistribution or other parameter of the drug can be altered by such combination or alternation therapy. In general, combination therapy is typically preferred over alternation therapy because it induces multiple simultaneous stresses on the virus.

In another embodiment, the prodrug is administered in combination or alternation with an immune modulator or other pharmaceutically active modifer of viral replication, including a biological material such as a protein, peptide, oligonucleotide, or gamma globulin, including but not limited to interfereon, interleukin, or an antisense oligonucleotides to genes which express or regulate hepatitis B replication.

Any method of alternation can be used that provides treatment to the patient. Nonlimiting examples of alternation patterns include 1–6 weeks of administration of an effective amount of one agent followed by 1–6 weeks of administration of an effective amount of a second anti-HBV agent. The alternation schedule can include periods of no treatment. Combination therapy generally includes the simultaneous administration of an effective ratio of dosages of two or more anti-HBV agents.

In light of the fact that HBV is often found in patients who are also anti-HIV antibody or HIV-antigen positive or who have been exposed to HIV, the active anti-HBV compounds disclosed herein or their derivatives or prodrugs can be administered in the appropriate circumstance in combination or alternation with anti-HIV medications.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor. A list compiling resistance data collected in vitro and in vivo for a number of antiviral compounds is found in Schinazi, et al, Mutations in retroviral genes associated with drug resistance, *International Antiviral News*, Volume 1(4), International Medical Press 1996.

The active anti-HBV agents can also be administered in combination with antibiotics, other antiviral compounds, antifungal agents or other pharmaceutical agents administered for the treatment of secondary infections.

VI. Pharmaceutical Compositions

Humans suffering from any of the disorders described herein, including hepatitis B, can be treated by administering to the patient an effective amount of a 3'-prodrug of a β-L-2'-deoxy-nucleoside of the present invention, or a pharmaceutically acceptable salt thereof, in the presence of a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount of compound to inhibit viral replication in vivo, without causing serious toxic effects in the patient treated. By "inhibitory amount" is meant an amount of active ingredient sufficient to exert an inhibitory effect as measured by, for example, an assay such as the ones described herein.

A preferred dose of the compound for all of the above-mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable prodrug can be calculated based on the weight of the parent nucleoside to be delivered. If the prodrug exhibits activity in itself, the effective dosage can be estimated as above using the weight of the prodrug, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or nonnucleoside antiviral agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylacetic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VII. Processes for the Preparation of Active Compounds

A. Method for the Preparation of β-L-3'-derivatives of β-L-nucleosides

β-L-3'-derivatives of a 2'-deoxy-nucleoside can be made by any means known in the art, particularly by known methods to protect secondary alcohols with acyl moieties, i.e. via an anhydride or with the aid of a coupling agent. As a non-limiting example, the 3'-derivatives can be prepared according to the following reaction sequence:

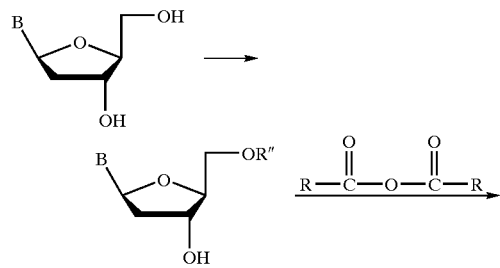

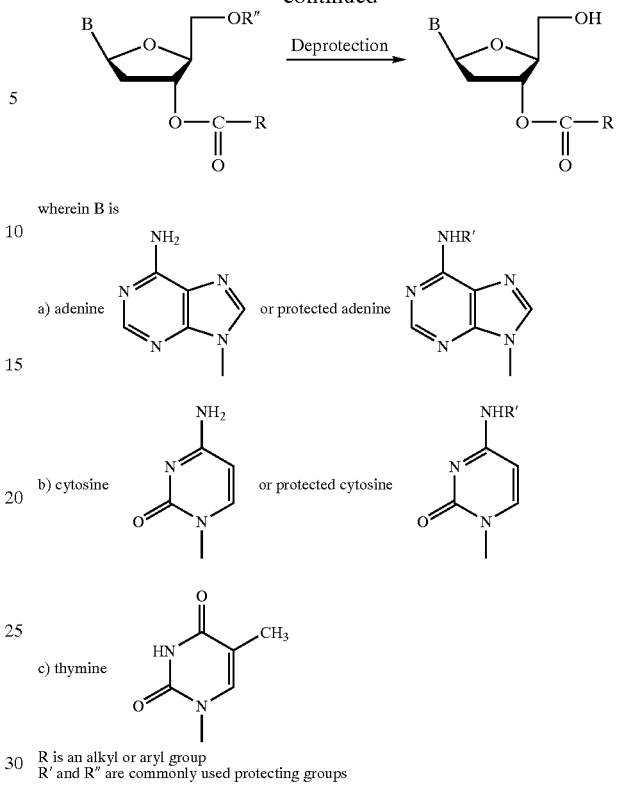

Alternatively, the 3'-derivative is derived from an aminoacyl moiety. The key starting material for this process is also an appropriately substituted β-L nucleoside. The β-L nucleoside can be purchased or can be prepared by any known means including standard coupling reactions with an L-sugar moiety.

These aminoacyl derivatives can be made by first selectively protecting the 5'-hydroxyl with a suitable oxygen protecting group, such as an acyl or silyl protecting group, and optionally protecting any free amine in the heterocyclic or heteroaromatic base. Subsequently, the free 3'-hydroxyl can be coupled to an N-protected α or β amino acid.

Subsequently, the β-L-nucleoside is coupled to the aminoacyl using standard coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Scheme 1 is a non-limiting example of the preparation of a β-L-3'-aminoacyl-nucleoside derived from L-deoxyribonucleoside.

Scheme 1

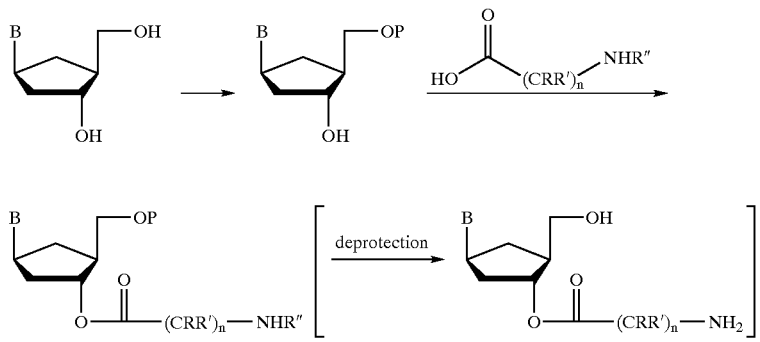

B. Method for the Preparation of β-L-5'-derivatives of β-L-nucleosides

β-L-5'-derivatives of a β-L-nucleoside can be made by any means known in the art, particularly by known methods to protect primary alcohols with acyl moieties, i.e. via an anhydride or with the aid of a coupling agent. As a non-limiting example, the β-L-5'-derivatives can be prepared according to the following reaction sequence:

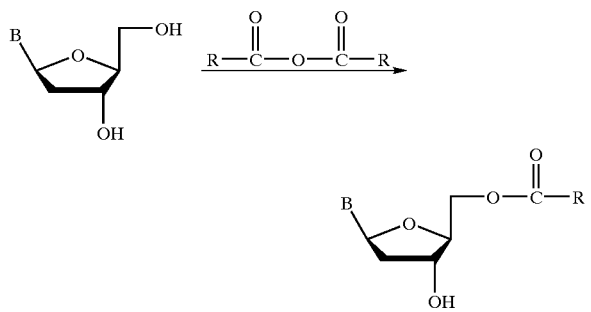

wherein B is

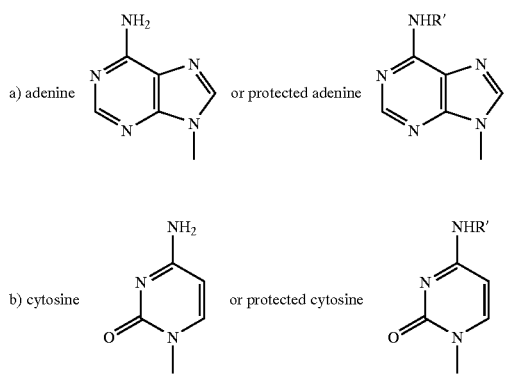

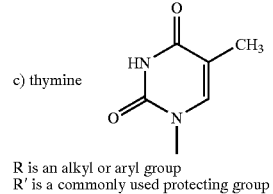

-continued c) thymine

R is an alkyl or aryl group
R' is a commonly used protecting group

In a preferred embodiment, the 5'-derivative is derived from an aminoacyl moiety. The key starting material for this process is an appropriately substituted β-L-nucleoside. The β-L-nucleoside can be purchased or can be prepared by any known means including standard coupling reactions with an L-sugar moiety, such as deoxyribose. The aminoacyl derivatives can be made by selectively coupling an amino acid to a β-L-nucleoside, preferably without any additional protection of the nucleoside. The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Scheme 2 is a non-limiting example of the preparation of a β-L-5'-aminoacyl-nucleoside derived from L-deoxyribonucleoside.

Scheme 2

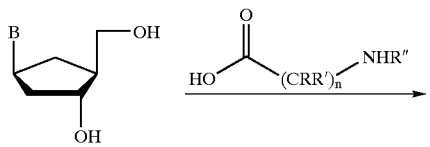

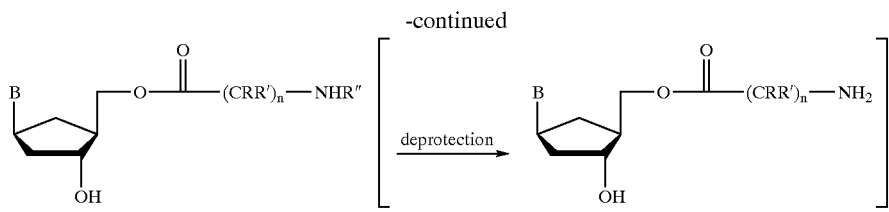

C. Method for the Preparation of β-L-3',5'-bis-O-derivatives of β-L-nucleosides

β-L-3',5'-bis-O-derivatives of a β-L-nucleoside can be made by any means known in the art, particularly by known methods to protect primary and secondary alcohols with acyl moieties, i.e. via an anhydride or with the aid of a coupling agent. As a non-limiting example, the 3',5'-bis-O-derivatives can be prepared according to the following reaction sequence:

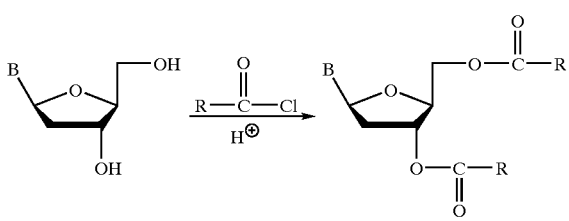

wherein B is

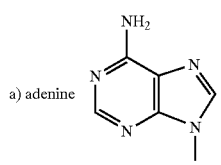
a) adenine

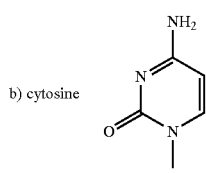
b) cytosine

-continued

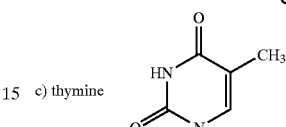
c) thymine

R is an alkyl or aryl group

In a preferred embodiment, the 3',5'-bis-O-derivative is derived from an aminoacyl moiety. The key starting material for this process is also an appropriately substituted β-L-nucleoside. The 3',5'-bis-O-derivatives of the β-L-nucleosides can be purchased or can be prepared by any known means including standard coupling reactions with an L-sugar moiety, such as deoxyribose. Subsequently, the free 3'- and 5'-hydroxyl can be coupled to N-protected α or β amino acid. The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Scheme 3 is a non-limiting example of the preparation of a β-L-3',5'-di-aminoacyl-nucleoside derived from L-deoxyribonucleoside.

Scheme 3

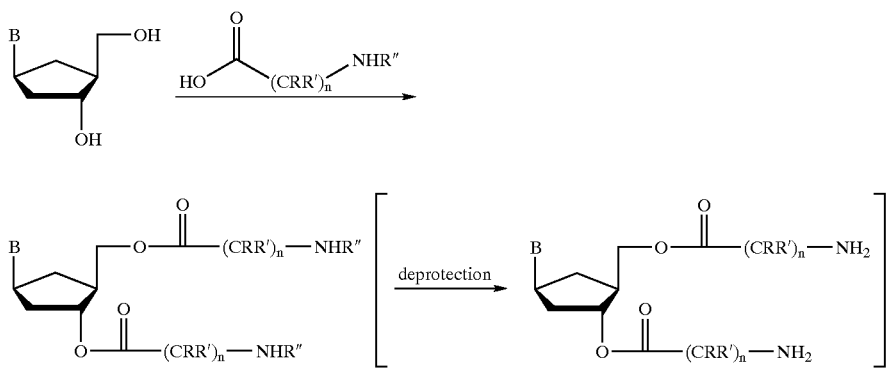

D. Optional Method for the Extension of the Aminoacyl Moiety

The title compounds can be made by reacting the 3' and 5'-hydroxyl with a suitable derivative, such as an acyl, and in particular an aminoacyl group. If the nucleoside is derivatized with an aminoacyl moiety, it may be desirable to further couple the free amine to a N-protected α or β amino acid. The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylfonnamide (DMF), dimethylsulfoxide (DMSO), dimethylacetamide, or any combination thereof.

E. Optional Method for Derivatization of the Heteroaromatic or Heterocyclic Base The title compounds can be made by optionally protecting any free amino in the heterocyclic or heteroaromatic base, for example $N^4$-cytosine, $N^6$-adenine or $N^2$-guanine. For example, the amine can be protected by an acyl moiety or a dialkylaminomethylene moiety by the following general protocol.

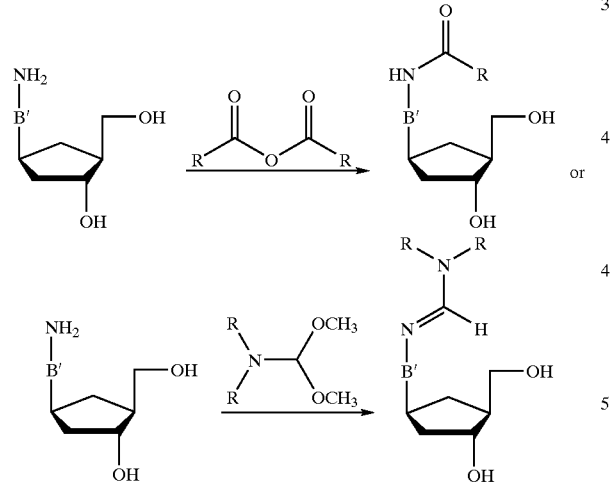

The protection can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Subsequently, the free 3'-hydroxyl can be coupled to a N-protected α or β amino acid. The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

In an alternate embodiment, the $N^4$- or $N^6$-acyl derivative is derived from an aminoacyl moiety, and can be prepared according to the following reaction sequence, by optionally protecting the free hydroxyls, followed by a condensation reaction with the appropriately protected amino ester, and the removal of the hydroxyl protecting groups, if necessary.

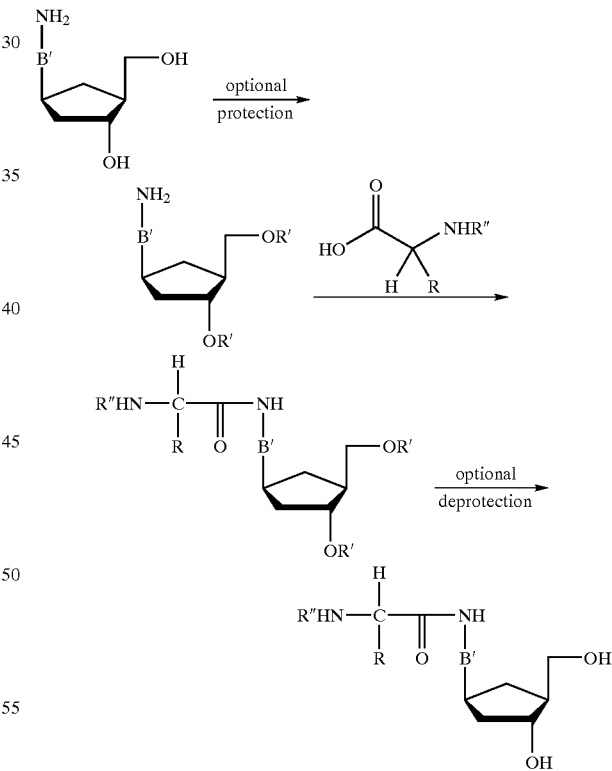

EXAMPLES

Example 1

$^4$N-mMTr-2'-deoxy-β-L-cytidine (1, FIG. 1)

β-L-dC (1 g; 4.40 mmol) was taken up in dry pyridine (44 ml). After transient protection with trimethylsilyl group (TMSCl, 3.34 ml, 26.4 mmol) followed by addition of mMTrCl (3.38 mg, 11 mmol) and 4-dimethylaminopyridine (DMAP, 540 mg, 4.40 mmol) the reaction mixture was stirred for 3 days at room temperature {A. Nyilas; C. Glemarec; J. Chattopadhyaya; *Tetrahedron Lett.* 1990, 46, 2149–2164}. After sodium bicarbonate extraction the organic layer was washed with water, evaporated and taken up in dioxane (40 mL). Aqueous ammonia (8.5 ml) was added dropwise and the reaction mixture was stirred overnight. After evaporation of all volatile materials, the solid residue was purified on silica gel column {eluent: stepwise gradient of MeOH (0–10%) in $CH_2Cl_2$}, giving the desired compound 1 (1.02 g, 46.5%) as a foam. $^1H$ NMR (DMSO-$d_6$) δ ppm 8.39 (br s, 1H, NH, $D_2O$ exchangeable), 7.70 (d, 1H, H-6, J=7.3 Hz), 7.4–6.8 (m, 14H, $(C_6H_5)_2C(C_6H_4)$ $OCH_3$), 6.23 (d, 1H, H-5, J=7.3 Hz), 6.02 (t, 1H, H-1', J=6.5 Hz), 5.16 (d, 1H, OH-3', J=3.8 Hz, $D_2O$ exchangeable), 4.9 (br s, 1H, OH-5', $D_2O$ exchangeable), 4.1 (m, 1H, H-3'), 3.7 (m, 4H, H-4', $OCH_3$), 3.5 (m, 2H, H-5', H-5"), 2.1–1.8 (2m, 2H, H-2', H-2"); FAB<0, (GT) m/e 498 (M–H)$^-$, 382 (B)$^-$; 226 (M-mMTr)$^-$; FAB>0 (GT) 500 (M+H)$^+$, 273 (mMTr)$^+$; UV (EtOH 95) $\lambda_{max}$=279 nm; $\lambda_{min}$=250 nm.

Example 2

5'-L-N-(tert-butoxycarbonyl) valine ester of $^4$N-mMTr-2'-deoxy-β-L-cytidine (2, FIG. 1)

To a solution of compound 1 (1 g, 2.00 mmol) in dry DMF (34 ml) were added successively 4-dimethylaminopyridine (DMAP, 37 mg, 0.3 mmol), N-(tert-butoxy-carbonyl)-L-valine (Boc-Val-OH, 587 mg, 2.7 mmol), and N,N'-dicyclohexylcarbodiimide (DCC, 660 mg, 3.2 mmol) {L. M. Beauchamp; G. F. Orr; P. De Miranda; T. Burnette; T. A. Krenitsky; *Antiviral Chem. Chemother.* 1992, 3, 157–164.}. The solution was stirred at room temperature. After 40 h, the reaction mixture was recharged with additional DMAP (37 mg, 0.3 mmol), Boc-Val-OH (587 mg, 2.7 mmol) and DCC (660 mg, 3.2 mmol) and stirred at room temperature for 40 h. The mixture was filtered, the DMF was removed from the filtrate under reduced pressure, and the residue was chromatographed on a silica gel column {eluent: stepwise gradient of MeOH (0–10%) in $CH_2Cl_2$} to afford the desired compound 2 (515 mg, 37%) as a foam. $^1H$ NMR (DMSO-$d_6$) δ ppm 8.44 (br s, 1H, NH, $D_2O$ exchangeable), 7.7–6.8 (m, 15H, H-6 and $(C_6H_5)_2C(C_6H_4)OCH_3$), 6.26 (d, 1H, H-5, J=7.3 Hz), 6.06 (t, 1H, H-1', J=6.6 Hz), 5.7 (bs, 1H, OH-3', $D_2O$ exchangeable), 4.2–4.0 (m, 3H, H-3', H-4' and CH), 3.8–3.9 (m, 2H, H-5', H-5"), 3.7 (s, 3H, $OCH_3$), 2.0–1.9 (m, 3H, H-2', H-2", CH), 1.36 (s, 9H, $(CH_3)_3C$), 0.86 (m, 6H, $(CH_3)_2CH$); FAB<0, (GT) m/e 1395 (2M–H)$^-$, 697 (M–H)$^-$, 425 (M-mMTr)$^{31}$, 382 (B)$^-$; 216 (BocVal-H)$^-$; FAB>0 (GT) 384 (B+2H)$^+$, 273 (mMTr)$^+$; 57 $(CH_3)_3C)^+$; UV (EtOH 95) $\lambda_{max}$=279 nm; $\lambda_{min}$=249 nm.

Example 3

5'-L-valine ester of 2'-deoxy-β-L-cytidine hydrochloride (3, FIG. 1)

Compound 2 (500 mg, 0.715 mmol) was dissolved in a 20% solution of trifluoroacetic acid in $CH_2Cl_2$ (25 ml) and triisopropylsilane (1.47 ml, 71.5 mmol) was added. The reaction mixture was stirred at room temperature for 1 h and the valine ester was precipitated in $Et_2O$ as the trifluoroacetate salt. After several coevaporations with water, the precipitate was taken up in water (2 ml), treated with a saturated solution of HCl in dioxane (20 ml) and evaporated under reduced pressure. This treatment was repeated 3 times and the desired compound 3 was finally precipitated in ether (207 mg, 73%) as the hydrochloride salt. $^1H$ NMR (DMSO-$d_6$) δ ppm 9.7 (br s, 1H, 1/2$NH_2$, $D_2O$ exchangeable), 8.6 (br s, 4H, 1/2$NH_2$, $NH_3$, $D_2O$ exchangeable), 7.98 (d, 1H, H-6 J=7.8 Hz), 6.17 (d, 1H, H-5, J=7.8 Hz), 6.11 pt, 1H, H-1'), 5.5 (bs, <1H, OH-3', $D_2O$ exchangeable), 4.4 (m, 2H, H-5', H-5"), 4.3 (m, 1H, H-3'), 4.2–4.0 (m, 2H, H-4', CH), 3.8–3.9, 3.7 (s, 3H, $OCH_3$), 2.3–2.1 (m, 3H, H-2', H-2", CH), 0.94 (dd, 6H, $(CH_3)_2CH$, J=3.7 and 6.6 Hz); FAB<0, (GT) m/e 361 (M+Cl)$^-$, 325 (M–H)$^-$, 116 (Val-H)$^-$, 110 (B)$^-$; 216 (BocVal-H)$^-$; FAB>0 (GT) 653 (2M+H)$^+$, 327 (M+H)$^+$; 112 (B+2H)$^+$; )$^+$; $\{\alpha\}_D^{20}$–28.57 (c=0.49 in DMSO); UV (EtOH 95) $\lambda_{max}$=272 nm (ε 8700); $\lambda_{min}$=255 nm (ε 7600); HPLC rt=8.37 min (gradient from 0 to 50% $CH_3N$ in 20 mM triethyl ammonium acetate buffer programmed over a 30 min period with a flow rate of 1 ml/min).

Example 4

$N^4$-Acetyl-2'-deoxy-β-L-cytidine (4, FIG. 2)

To a suspension of the nucleoside, β-L-dC (415 mg, 1.83 mmol) in N,N-dimethylformamide (9.2 ml) was added acetic anhydride (207 μl, 2.20 mmol) and the mixture was stirred at room temperature for 24 h [V. Bhat; B. G. Ugarkar; V. A. Sayeed, K. Grimm; N. Kosora; P. A. Domenico; E. Stocker, *Nucleosides & Nucleotides,* 1989, 8 (2), 179–183]. After removal of the DMF under reduced pressure, the resulting residue was purified by silica gel column chromatography [eluant: 15% MeOH in $CH_2Cl_2$] to afford the desired compound (310 mg, 63%) which was crystallized from ethanol; rap 128–170° C.; $^1H$ NMR (DMSO-$d_6$) δ ppm 10.86 (s, 1H, NH, $D_2O$ exchangeable), 8.31 (d, 1H, H-6, J=7.5 Hz), 7.18 (d, 1H, H-5, J=7.5 Hz), 6.09 (t, 1H, H-1', J=6.3 Hz), 5.25 (d, 1H, OH-3', $D_2O$ exchangeable, J=4.2 Hz), 5.03 (t, 1H, OH-5', $D_2O$ exchangeable, J=5.0 Hz), 4.1–4.2 (m, 1H, H-3'), 3.8 (m, 1H, H-4'), 3.4–3.6 (m, 2H, H-5', H-5"), 2.2–2.3 (m, 1H, H-2'), 2.08 (s, 3H, $CH_3$), 2.0–1.9 (m, 1H, H-2"); FAB<0, (GT) m/e 806 (3M–H)$^-$, 537 (2M–H)$^-$, 360 (M+G–H)$^-$, 268 (M–H)$^-$, 152 (B)$^-$; FAB>0 (GT) 808 (3M+H)$^+$, 539 (2M+H)$^+$, 362 (M+G+H)$^+$, 270 (M+H)$^+$, 154 (B+2H)$^+$, 117 (S)$^+$; UV ($H_2O$) $\lambda_{max}$=297 nm (ε 8300); $\lambda_{min}$=270 nm (ε 3500);. $\lambda_{max}$=245 nm (ε 14400); $\lambda_{min}$=226 nm (ε 5800); $[\alpha]_D^{20}$–81.31 (c=1.07 in DMSO).

Example 5

$N^4$-[(Dimethylamino)methylene]-2'-deoxy-β-L-cytidine (5, FIG. 3)

The title compound was prepared according to a published procedure developed for the preparation of the corresponding D-enantiomer [S. G. Kerr, and T. I. Kalman, *J. Pharm. Sci.* 1994, 83, 582–586]. A solution of L-dC (500 mg, 2.20 mmol) in DMF (4.8 ml) was treated with dimethylformamide dimethylacetal (2.8 ml, 21.08 mmol), and stirred at room temperature overnight. The solution was evaporated under reduced pressure, and coevaporated with ethanol. Crystallization from ethanol/ether yielded the title compound (501.2 mg, 81%) as light yellow crystals. mp 174–176° C. (lit.: 188–190° C. for the D-enantiomer); $^1H$ NMR (DMSO-$d_6$) δ ppm 8.60 (s, 1H, N=CH), 8.00 (d, 1H, H-6), 6.15 (t, J=6.6 Hz, 1H, H-1'), 5.96 (d, J=7.2 Hz, 1H, H-5), 5.22 (d, J=4.2 Hz, 1H, OH-3'), 5.01 (t, J=5.2 Hz, 1H, OH-5'), 4.20 (m, 1H, H-4'), 3.80 (m, 1H, H-3'), 3.56 (m, 2H, H-5' and H-5"), 3.15 and 3.02 (2s, 3H and 3H, N($CH_3$)$_2$), 2.22–1.90 (2 m, 1H and 1H, H-2' and H-2"); FAB>0 (GT) 847 (3M+H)$^+$, 565 (2M+H)$^+$, 283 (M+H); FAB<0, (GT) m/z 599 (2M+Cl)$^-$, 317 (M+Cl)$^-$, 165 (B)$^-$.

Example 6

3',5'-Di-O-acetyl-2'-deoxy-β-L-cytidine (6, FIG. 4)

The title compound has been synthesized in one step starting from the L-dC and following a procedure developed by Breiner et al [R. G. Breiner; W. Rose; J. A. Dunn; J. E. Mae Diarmid and J. Bardos; *J. Med. Chem.* 1990, 33, 2596–2603] for the preparation of the D-enantiomer. A solution of L-dC (765 mg, 3.37 mmol) and acetyl chloride (960 μl, 13.48 mmol) in glacial acetic acid (4.8 ml) was stirred at room temperature for 10 min, then dry chloroform (3.5 ml) was added and the stirring was continued for 24 h. The solution was evaporated under reduced pressure and coevaporated with ethanol. Crystallization from ethanol yielded 78% of the desired compound, mp 192.193° C. (lit: 187–189° C. for the D-enantiomer [Breiner et al. *J. Med. Chem.* 1990, 33, 2596–2603]); $^1$H NMR (DMSO-d$_6$) δ ppm 9.8 and 8.7 (2 br s, <3H, NH$_3^+$, D$_2$O exchangeable), 8.0 (d, 1H, H-6 J=7.8 Hz), 6.18 (d, 1H, H-5, J=7.8 Hz), 6.08 (t, 1H, H-1', J=6.7 Hz), 5.2 (m, 1H, H-3'), 4.3–4.1 (m, 3H, H-4', H-5', H-5"), 2,4–2,5 (m, 2H, H-2', H-2"), 2.06 and 2.03 (2 s, 6H, 2 CH$_3$); FAB<0, (GT) m/e 968 (3M+Cl)$^-$, 657 (2M+Cl)$^-$, 438 (M+G+Cl)$^-$, 346 (M+Cl)$^-$, 310 (M−H)$^-$, 110 (B)$^-$; 59 (CH$_3$COO)$^-$; FAB>0 (GT) 623 (2M+H)$^+$, 312 (M+H)$^+$, 201 (S)$^+$, 112 (B+2H)$^+$, 43 (CH$_3$CO)+; [α]$_D^{20}$ 36.27 (c=1.02 in DMSO); UV (MeOH) λ$_{max}$=277 nm (ε 9900); λ$_{min}$=246 nm (ε 5000).

Example 7

3',5'-L-N-(t-Butoxycarbonyl)valine diester of 2'-deoxy-β-L-cytidine (9, FIG. 5)

A solution of N$^4$-[(dimethylamino)methylene]-2'-deoxy-β-L-cytidine (7, 500 mg, 1.77 mmol) in DMF (35 ml) was treated with Boc-Val-OH (1.31 g, 6.03 mmol), DMAP (86.5 mg, 0.71 mmol), 1-(3-dimethylaminopropyl)-3-ethylcarbodiimide hydrochloride (EDC) (1.36 g, 7.09 mmol), and stirred at room temperature for 40 hours. Additional quantities of Boc-Val-OH (655 mg, 3.01 mmol), DMAP (43.2 mg, 0.35 mmol), EDC (680 mg, 3.55 mmol) were added, and the solution was stirred for an additional 20 hours. After evaporation under reduced pressure, the residue was taken up in CH$_2$Cl$_2$, and extracted several times with water. The organic layer was washed with brine (100 ml), dried (Na$_2$SO$_4$), and evaporated under reduced pressure to give 8 as a crude material, which was used for the next step without further purification. The residue was taken up in dioxane (18 ml), treated with aq. 26% NH$_4$OH, and stirred at room temperature for 1 hour. The solution was evaporated under reduced pressure, and the residue was purified by chromatography on silica gel using a stepwise gradient of MeOH (0–5%) in CH$_2$Cl$_2$, to give the title compound (698.7 mg, 58% from 9). $^1$H NMR (DMSO-d$_6$) δ ppm 7.58 (d, 1H, H-6), 7.29–7.18 (m, 4H, NH-Boc and NH$_2$), 6.20 (t, J=6.6 Hz, 1H, H-1'), 5.75 (d, J=7.3 Hz, 1H, H-5), 5.20 (br. s, 1H, H-3'), 4.29 (m, 2H, H-5' and H-5"), 4.14 (br. s, 1H, H-4'), 3.86 (m, 2H, CH—NH-Boc), 2.31–2.21 (m, 2H, H-2' and H-2"), 2.13–1.98 (m, 2H, CH(iPr)), 1.38 and 1.36 (2s, 18H, tBu), 0.88 and 0.85 (2 d, J=6.8 Hz, 12H, CH(CH$_3$)$_2$); $^{13}$C NMR (DMSO-d$_6$) δ ppm 172.67 and 172.46, 166.41, 156.64 and 155.70, 141.39, 95.43, 85.78, 82.03, 79.14, 75.57, 64.90, 60.37 and 60.11, 37.40, 30.33, 29.00, 19.83–19.12; FAB>0 (GT) 626 (M+H)+, 112 (B+2H)$^+$, 255 (M-Boc)$^+$; FAB<0, (GT) m/z 1249 (2M−H)$^-$, 624 (M−H)$^-$.

Example 8

3,5'-L-Valine ester of 2'-deoxy-β-L-cytidine hydrochloride (10, FIG. 5)

A solution of 9 (675 mg, 1.08 mmol) in dioxane (30 ml) was treated with a solution of 26% HCl in dioxane (30 ml), and stirred at room temperature for 1 hr 55. The resulting white suspension was evaporated under reduced pressure. The white solid residue was taken up in the minimal amount of MeOH and precipitated in ether to give the title compound 10 as a white solid. mp 187° C. (decomp.); $^1$H NMR (DMSO-d$_6$) δ ppm 9.79 (br s, 1H, 1/2NH$_2$), 8.72 (br s, 7H, 1/2NH$_2$ and NH$_3^+$), 8.04 (d, 1H, H-6), 6.21 (d, J=7.8 Hz, 1H, H-5), 6.16 (t, J=6.9 Hz, 1H, H-1'), 5.39 (m, 1H, H-3'), 4.50–4.40 (m, 3H, H-4', H-5' and H-5"), 3.90 (2 br. d, 2H, CH—NH$_3^+$), 2.63–2.50 (2m, 2H, H-2' and H-2"), 2.21 (m, 2H, CH(iPr)), 1.02–0.94 (m, 12H, CH(CH$_3$)$_2$); $^{13}$C NMR (DMSO-d$_6$) δ ppm 169.50 and 168.94, 161.02, 148.50, 145.26, 95.18, 87.19, 82.15, 76.14, 65.77 and 65.59, 58.12 and 58.07, 37.00, 30.16, 19.26–18.51; FAB>0 (GT) 426 (M+H)$^+$, 112 (B+2H)$^+$; FAB<0, (GT) m/z 885 (2M+Cl)$^-$, 460 (M+Cl); UV (H$_2$O) λ$_{max}$=270 nm (ε 7600).

Example 9

N$^4$-Boc-Valinyl ester of 2'-deoxy-β-L-cytidine (13, FIG. 6)

A mixture of L-dC (1.80 g, 7.92 mmol) and triethylamine (8.8 ml, 63.14 mmol) in anhydrous THF (80 ml) was treated with chlorotrimethylsilane (6 ml, 47.28 mmol) and stirred at room temperature overnight. The reaction was quenched by addition of an aqueous saturated solution of NH$_4$Cl (26 ml) and water (10 mL). The aqueous layer was extracted three times with EtOAc. The organic layers were combined, washed with brine, dried (Na$_2$SO$_4$) and evaporated under reduced pressure to give a crude light yellow foam-oil containing 11, which was used for the next step without further purification. This residue was taken up in CH$_2$Cl$_2$ (104 ml), treated with N-(tert-butoxycarbonyl)-L-valine (Boc-Val-OH, 1.72 g, 7.90 mmol), benzotriazol-1-yloxy-tris (dimethylamino) phosphonium hexafluorophosphate (BOP, 4.20 g, 9.50 mmol), triethylamine (2.2 ml, 15.78 mmol), and stirred at room temperature for 2 days. The solution was diluted with EtOAc and extracted twice with sat. NaHCO$_3$. The organic layer was dried (Na$_2$SO$_4$) and evaporated under reduced pressure to give 12 as a crude material, which was used for the next step without further purification. This residue was taken up in dioxane (80 ml), treated with aq. 26% NH$_4$OH solution, and stirred at room temperature for 6 h 45. The solution was evaporated under reduced pressure, coevaporated with absolute EtOH, and the residue was purified by chromatography on silica gel, using a stepwise gradient of MeOH (5–10%) in CH$_2$Cl$_2$, to give the title compound 13 as a foam (1.64 g, 48.5% overall yield). $^1$H NMR (DMSO-d$_6$) δ ppm 10.88 (s, 1H, NH-4), 8.40 (d, 1H, H-6), 7.26 (d, J=7.4 Hz, 1H, H-5), 7.06 (d, J=8.2 Hz, 1H, CH—NH-Boc), 6.15 (t, J=6.3 Hz, 1H, H-1'), 5.32 (d, J=4.2 Hz, 1H, OH-3'), 5.09 (t, J=5.2 Hz, 1H, OH-5'), 4.27 (m, 1H, H-3'), 4.06 (pt, J=7.5 Hz, 1H, CH—NH-Boc), 3.91 (m, 1H, H-4'), 3.63 (m, 2H, H-5' and H-5"), 235 (m, 1H, H-2"), 2.06 (m, 2H, H-2' and CH(CH$_3$)$_2$), 1.43 (s, 9H, tBu), 0.92 (pt, J=6.6 Hz, 6H, CH(CH$_3$)$_2$); $^{13}$C NMR (DMSO-d$_6$) δ ppm 174.41, 162.94, 156.47, 155.24, 146.10, 96.06, 88.79, 87.10, 79.09, 70.75, 61.78, 61.55, 41.74, 30.63, 29.02, 19.91 and 19.10; FAB>0 (GT) 853 (2M+H)$^+$, 427 (M+H)$^+$ 311 (B+2H)$^+$, 255 (M-Boc)$^+$; FAB<0, (GT) m/z 851 (2M−H)$^-$, 425 (M−H)$^-$, 309 (B)$^-$.

Example 10

3',5'-N$^4$-Trivalyl-2'-deoxycytidine (14, FIG. 7)

The starting material, 3',5'-N$^4$-tri(Boc-valyl)-2'-deoxycytidine was dissolved in CH$_2$Cl$_2$, but there was some insoluble material so the sample was filtered through Perlita.

This resulted in an increase in the volume of the $CH_2Cl_2$ used. The HCl/dioxane reagent was then added with stirring. Within a few seconds some bubbling could be observed in the solution and then the mixture became cloudy. The mixture was stirred at room temperature for about 1 hr. During this time the precipitate became more crystalline. The mixture was quickly filtered, the filtercake was washed with $CH_2Cl_2$, and then it was dried on the pump to give, 0.16 g (69%) of cream-white crystals. The reagents and conditions are more explicitly described below in Table 1.

TABLE 1

| Reagent | Mol. Unit | Wt./Vol calc | Mol/pts | Wt/Vol used | Mol/pts | Equiv |
|---|---|---|---|---|---|---|
| 3',5',N4-triBoc-Val-2'-dC (CyVal2a-2a) | 825.0 FW | 0.30 g | 0.00036 | 0.3 g | 0.00036 | 1.00 |
| $CH_2Cl_2$ | 5.0 parts | 1.5 mL | 5 | 3.0 mL | 10 | 10.0 |
| HCl, 3.9 M in dioxane− | 256.0 mL/mol | 0.47 g | 0.00182 | 0.5 g | 0.00195 | 5.37 |
| 3',5',N4-triVal-2'-dC, crude | 634.0 FW | 0.23 g | calc-obt | 0.16 g | 69.4% | |

Example 11

HPLC Assay Method for DiBocValyl-2'-dC and DiBocValyl-2'-dU

A 1.0 mg/mL sample was made by dissolving the desired compound in absolute ethanol. The solution was then diluted with a solution that contained 50% MeOH and 50% $KH_2PO_4$ (0.015M, pH=3.30–3.50) until a concentration of 0.16 mg/mL was obtained. (Note: all solvents used were degasified before use.) 20 μL of the solution was then immediately injected into an HPLC column from WATERS (NOVAPAK C18—4 pm—3,9×150 mm). The flow rate was set at 1 mL/min with a column temperature of 35° C. To detect the compounds, the wavelength detection was set at 275 nm for Di-Boc 2'dC, 260 nm for Di-Boc2'dU and 204 for impurities after 15 minutes. The column was run with $KH_2PO_4$ (0.015M, pH=3.30–3.50, adjusted with $H_3PO_4$ 10% v/v) in Pump A and HPLC grade acetonitrile in Pump B. The gradient pattern is indicated in Table 2.

TABLE 2

| # | Time | Module | Event | Volume |
|---|---|---|---|---|
| 1 | 0.01 | Pumps | T. Flow | 1 |
| 2 | 0.01 | Pumps | B. Conc. | 45 |
| 3 | 12.00 | Pumps | B. Conc. | 45 |
| 4 | 20.00 | Pumps | B. Conc. | 70 |
| 5 | 28.00 | Pumps | B. Conc. | 70 |
| 6 | 28.00 | Pumps | B. Conc. | 45 |
| 7 | 32.00 | Pumps | B. Conc. | 45 |
| 8 | 32.01 | SCL-10Avp | STOP | 0 |

VIII. Anti-HBV Activity of the Active Compounds

Human DNA polymnerases and mitochondrial function were not affected by L-dC in vitro. L-dC was non-cytotoxic to human peripheral blood mononuclear cells (PBMCs), bone marrow progenitor cells and numerous cell lines of human and other non-human mammalian origin.

The antiviral activity and safety of L-dC was investigated in two studies using the woodchuck model of chronic hepatitis B infection. In the initial study, woodchucks chronically infected with WHV (>10[11] genome equivalents/ML serum) were treated with a liquid formulation of L-dC by the oral route once a day for 28 days. Control animals received lamivudine or the liquid formulation without drug. In the L-dC treated groups, viral load decreased in a dose-dependent manner. At the highest dose tested (10 mg/kg/day), viral load decreased by as much as 6 logs from baseline by quantitative polymerase chain reaction (PCR) assay, Post-treatment virus rebound was detected by Week 2. All animals gained weight and there was no drug-related toxicity observed during the four-week treatment phase or eight-week post-treatment follow-up period.

The in vitro 50% effective concentration ($EC_{50}$) for reduction in extracellular viral deoxyribonucleic acid (DNA) by L-dC was 0.24 μM against HBV and 0.87 μM against DHBV. In addition, L-dC reduced intracellular HBV DNA replicative intermediates (RI) with an $EC_{50}$ of 0.51 μM. The 90% effective concentration ($EC_{90}$) of L-dC against HBV replication was 1.07 μM. Structure activity relationships (SAR) show that replacement of the hydroxyl group in the 3' position (3'-OH) broadened the antiviral activity from hepadnaviruses to other viruses including human immunodeficiency virus (HIV) and certain herpes viruses. Substitution in the base decreased antiviral potency and selectivity.

The second study using the woodchuck model of chronic hepatitis B virus infection tested the antiviral effect and safety of L-dC in combination with a second investigational nucleoside [β-L-2'-deoxythymidine (L-dT)]. Included in this study was a treatment group in which L-dC was used as a single agent (1 mg/kg/day). There was no drug-related toxicity observed for L-dC alone or in combination with L-dT during the 12-week treatment phase or 12-week post-treatment follow-up period. There were no changes in body weight relative to control animals or serum chemistry and hematologic parameters. End-of-treatment liver biopsies showed no histomorphological evidence of fatty changes (microvesicular steatosis). The combination of L-dC (1 mg/kg/day) plus L-dT (1 mg/kg/day) was synergistic and reduced viral load by up to 8 logs from baseline.

Antiviral nucleosides and nucleoside analogs exert their antiviral effect as intracellular triphosphate derivatives at the level of the viral polymerase during virus replication. Like natural nucleosides (D-deoxycytidine and D-thymidine) and antiviral nucleoside analogs (e.g., lamivudine and zidovudine), L-dC was activated intracellularly by phosphorylation. In human hepatocytes, deoxycytidine kinase (dCK) was responsible for the dose-dependent initial conversion of L-dC to a 5'-monophosphate (MP) derivative. L-dC-MP was then converted to a 5'-diphosphate (DP) form, which was subsequently converted to the predominant intracellular 5'-triphosphate (TP) metabolite. The L-dC-TP level reached 72.4 μM in HepG2 cells exposed to 10 μM L-dC (90.1 μM in primary human hepatocytes) at 24 hours and had an intracellular half-life of 15.5 hours. In endogenous polymerase assays, L-dC-TP inhibited the virion-associated DNA polymerase of WHV with a 50% inhibitory concentration ($IC_{50}$) of 1.82 μM. The detailed mechanism of inhibition of HBV DNA polymerase by L-dC is under investigation. Exposure of HepG2 cells or human hepacytes in primary culture to L-dC also produced a second TP derivative, β-L-2'-deoxyuridine 5'-triphosphate (L-dU-TP). The L-dU-TP level reached 18.2 μM in HepG2 cells exposed to 10 μM L-dC (43.5 μM in primary human hepatocytes) at 24 hours. In endogenous polymerase assays, L-dU-TP inhibited virion-associated DNA polymerases of WHV with an $IC_{50}$ of 5.26 μM.

In primary human hepatocyte cultures and in a human hepatoma cell line (HepG2), the major metabolite of L-dC was L-dC-TP. Exposure of these cells to L-dC also led to the formation of L-dU-TP. In vitro pharmacological assays showed that L-dC-TP inhibited hepadnaviral DNA synthesis with an $IC_{50}$ of 1.82 mM, against virion-associated DNA polymerase. L-dU-TP inhibited hepadnaviral DNA synthesis with an $IC_{50}$ of 5.26 μM. L-dC-TP and L-dU-TP did not inhibit human DNA polymerases α, β and γ up to concentrations of 100 μM, the highest concentration tested.

The ability of the active compounds to inhibit the growth of virus in 2.2.15 cell cultures (HepG2 cells transformed with hepatitis virion) can be evaluated as described in detail below.

A summary and description of the assay for antiviral effects in this culture system and the analysis of HBV DNA has been described (Korba and Milman, 1991, *Antiviral Res.*, 15:217). The antiviral evaluations are performed on two separate passages of cells. All wells, in all plates, are seeded at the same density and at the same time.

Due to the inherent variations in the levels of both intracellular and extracellular HBV DNA, only depressions greater than 3.5-fold (for HBV virion DNA) or 3.0-fold (for HBV DNA replication intermediates) from the average levels for these HBV DNA forms in untreated cells are considered to be statistically significant (P<0.05). The levels of integrated HBV DNA in each cellular DNA preparation (which remain constant on a per cell basis in these experiments) are used to calculate the levels of intracellular HBV DNA forms, thereby ensuring that equal amounts of cellular DNA are compared between separate samples.

Typical values for extracellular HBV virion DNA in untreated cells range from 50 to 150 pg/ml culture medium (average of approximately 76 pg/ml). Intracellular HBV DNA replication intermediates in untreated cells range from 50 to 100 μg/pg cell DNA (average approximately 74 pg/μg cell DNA). In general, depressions in the levels of intracellular HBV DNA due to treatment with antiviral compounds are less pronounced, and occur more slowly, than depressions in the levels of HBV virion DNA (Korba and Milman, 1991, *Antiviral Res.*, 15:217).

The manner in which the hybridization analyses are performed results in an equivalence of approximately 1.0 pg of intracellular HBV DNA to 2–3 genomic copies per cell and 1.0 pg/ml of extracellular HBV DNA to $3 \times 10^5$ viral particles/mL.

EXAMPLES

Example 12

Solubility Study

The solubility of natural deoxyribocytosine (D-dC), the 3'-valinyl ester of L-dC and the 3',5'-divalinyl ester of L-dC in water was compared. The solubility of L-dC was assessed first by analyzing the HPLC data (i.e. area under the curve) by successive injections of various well-known concentrations of β-L-dC, as shown in Table 3. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. The concentration of the solution versus the area under the curve produced a linear relationship with y=4150049477x−4334.46845 (FIG. 8a).

TABLE 3

| Concentration (mol/l) | $10^{-3}$ | $5 \times 10^{-4}$ | $10^{-4}$ | $10^{-5}$ |
|---|---|---|---|---|
| Area | 4175916 | 2031950 | 440122 | 55264 |

From this, a saturated solution was prepared with natural deoxyribocytosine (D-dC); 3 samples were taken and injected into the HPLC. The concentration of this saturated solution was determined to be 1.07, 1.08 and 0.96 mol/L; therefore, the saturated solution had an average saturated concentration of 1.03 mol/L or 272 g/L. The results are tabulated in Table 4.

TABLE 4

| Results | Area | Concentration (mol/L) |
|---|---|---|
| 1st Sample | 4420674000 | 1.07 |
| 2nd Sample | 4475191000 | 1.08 |
| 3rd Sample | 3983845000 | 0.96 |

Similarly, the solubility of 3'-valinyl ester hydrochloride of β-L-dC in water was evaluated. The calibration curve was determined by successive injections of various concentrations of the 3'-Valinyl ester hydrochloride of β-L-dC into the HPLC and measuring the area under the curve, as shown in Table 5. Again, the HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. The concentration of the solution versus the area under the curve produced a linear relationship with y=3176423963x−33051.63.

TABLE 5

| Concentration (mol/L) | $10^{-3}$ | $5 \times 10^{-4}$ | $10^{-4}$ | $5 \times 10^{-5}$ | $10^{-5}$ |
|---|---|---|---|---|---|
| Area | 3,166,842 | 1,514,479 | 254,296 | 119,668 | 19,269 |

From this, a saturated solution was attempted for 3'-valinyl ester hydrochloride of β-L-dC; however, one was not obtained. Therefore, the maximum quantity of 3'-valinyl ester hydrochloride of β-L-dC readily available in the laboratory was dissolved in water. 3 samples were collected, and were determined from the area under the curve from the HPLC, to have an average concentration of 1.013, 0.996 and 1.059 mol/L. The results are tabulated in Table 6.

TABLE 6

| Results | Area | Concentration (mol/L) |
|---|---|---|
| 1st Sample | 3218013000 | 1.013 |
| 2nd Sample | 3162471000 | 0.996 |
| 3rd Sample | 3362725000 | 1.059 |

All three results fell within the predicted range calculated from the calibration curve, indicating complete solubility of the compound at those high concentrations, indicating that a saturated solution of this sample is greater than the average of the three samples, i.e. greater than 1.023 mol/L or 408 g/L.

The solubility of 3',5'-divalinyl ester hydrochloride of β-L-dC in water was evaluated. The calibration curve was determined by successive injections of various concentrations of the 3',5'-divalinyl ester hydrochloride of β-L-dC into the HPLC and measuring the area under the curve, as shown in Table 7. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. The concentration of the solution versus the area under the curve produced a linear relationship with y=3176423963x−33051.63 (FIG. 8b).

TABLE 7

| Concentration (mol/l) | $10^{-3}$ | $5 \times 10^{-4}$ | $10^{-4}$ | $5 \times 10^{-5}$ | $10^{-5}$ |
|---|---|---|---|---|---|
| Area | 2863372 | 1466574 | 211046 | 115678 | 14435 |

From this, a saturated solution was attempted for 3',5'-divalinyl ester hydrochloride of β-L-dC; however, one was not obtained. Therefore, the maximum quantity of 3',5'-divalinyl ester hydrochloride of β-L-dC readily available in the laboratory was dissolved in water. 3 samples were collected, and were determined from the area under the curve from the HPLC, to have an average concentration of 2.8, 2.4 and 2.4 mol/L. The results are tabulated in Table 8.

TABLE 8

| Results | Area | Concentration (mol/L) |
|---|---|---|
| 1st Sample | 8336188000 | 2.8 |
| 2nd Sample | 7054012000 | 2.4 |
| 3rd Sample | 6970838000 | 2.4 |

All three results fell within the predicted range calculated from the calibration curve, indicating complete solubility of the compound at those high concentrations, indicating that a saturated solution of this sample is greater than the average of the three samples, i.e. more than 2.5 mol/L or 1337 g/L.

Similar solubility studies were done on 5'-valinyl ester hydrochloride of β-L-dC (more than 5.1 mol/L or 1664 g/L) and 3'5'-diacetyl ester hydrochloride of β-L-dC (3.3 mol/L or 1148 g/L). The cumulative results are tabulated in Table 9.

TABLE 9

| Compound | Solubility (mol/L) | Solubility (g/L) |
|---|---|---|
| D-dC | 1.03 | 272 |
| 5'-val-L-dC | >5.1 | >1664 |
| 3'-val-L-dC | >1.023 | >408 |
| 3'5'-diacetyl-L-dC | 3.3 | 1148 |
| 3'5'-dival-L-dC | >2.5 | >1337 |

Example 13

Log P Study—Phosphate Buffer

Approximately 1.5 mg of D-dC was dissolved in 2.2 mL of 0.02 M phosphate buffer solution (A, 100 mL, pH 7.2), made from a mixture of monobasic potassium phosphate solution (28.5 mL) and dibasic potassium phosphate solution (71.5 mL), saturated with octanol-1 (B). To 1 mL of this solution, 1 mL of octanol-1 (B) saturated with 0.02 M phosphate buffer solution (A) was added. The resultant mixture was shaken and centrifuged; three samples from each phase was collected and analyzed by HPLC, as shown in Table 10. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. It was found that the log P of D-dC is −1.41; therefore, D-dC prefers water to octanol.

TABLE 10

| | Study 1 | | | | | | Study 2 | | | | | |
|---|---|---|---|---|---|---|---|---|---|---|---|---|
| | $A^1$ | $A^2$ | $A^3$ | $B^1$ | $B^2$ | $B^3$ | $A^1$ | $A^2$ | $A^3$ | $B^1$ | $B^2$ | $B^3$ |
| Area | 1948481 | 2130720 | 2197377 | 79838 | 82172 | 80159 | 2380141 | 2326654 | 2339059 | 93123 | 90275 | 89651 |
| Average | | 2092193 | | | 80723 | | | 2348618 | | | 91016 | |
| P (B/A) | | | 0.039 | | | | | | 0.039 | | | |
| log P | | | −1.41 | | | | | | −1.41 | | | |

Similarly, approximately 1.5 mg of L-dC-3'-valine ester hydrochloride was dissolved in 2.5 mL of 0.02 M phosphate buffer solution (A, 100 mL, pH 7.2), made from a mixture of monobasic potassium phosphate solution (28.5 mL) and dibasic potassium phosphate solution (71.5 mL). The solution was then saturated with octanol-1 (B). To 1 mL of this solution, 1 mL of octanol-1 (B) saturated with 0.02 M phosphate buffer solution (A) was added. The resultant mixture was shaken and centrifuged; three samples from each phase was collected and analyzed by HPLC, as shown in Table 11. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute.

TABLE 11

| | Study 1 | | | | | | Study 2 | | | | | |
|---|---|---|---|---|---|---|---|---|---|---|---|---|
| | $A^1$ | $A^2$ | $A^3$ | $B^1$ | $B^2$ | $B^3$ | $A^1$ | $A^2$ | $A^3$ | $B^1$ | $B^2$ | $B^3$ |
| Area | 3352735 | / | 3417723 | 100544 | 96843 | 103466 | 3458180 | 3448062 | 3412971 | 100179 | / | 101731 |
| Average | 3385227 | | | 100284 | | | 3439738 | | | 100955 | | |
| P (B/A) | 0.0296 | | | | | | 0.0293 | | | | | |
| log P | −1.53 | | | | | | −1.53 | | | | | |

It was found that the log P of L-dC-3'-valine ester hydrochloride is −1.53; therefore, L-dC-3'-valine ester prefers water to octanol to a greater degree than D-dC.

Log P values were calculated for L-dC-5'-valine ester hydrochloride and L-dC-3',5'-divaline ester hydrochloride. The results are tabulated in Table 12. However, it should be noted that the log P value for L-dC-3',5'-divaline ester hydrochloride is probably lower than the one measured (−0.86). Significant conversion of the divaline ester into the 3'- or 5'-monovalinyl ester or even L-dC was observed during the experiment. 50% of conversion of L-dC-3',5'-divaline ester hydrochloride was detected in the aqueous phase and 14% in the organic phase. This conversion is due to the instability of the esters in the phosphate buffer at a pH of 7 (see examples 15 and 16).

TABLE 12

| Compound | log P (octanol/water) |
|---|---|
| D-dC | −1.41 |
| L-dC-3'-valine ester hydrochloride | −1.53 |

TABLE 12-continued

| Compound | log P (octanol/water) |
|---|---|
| L-dC-5'-valine ester hydrochloride | −1.42 |
| L-dC-3',5'-divaline ester hydrochloride | −0.86 |
| L-dC-3',5'-diacetyl ester hydrochloride | −0.74 |

Example 14

Log P' Study—MilliQ Water

In order to avoid the conversion of the divaline ester into the mono esters and L-dC, an alternate log P study was performed using MilliQ water (A') instead of the phosphate buffer (pH of 6.5 instead of 7.2). It is important to note that only the hydrochloride form of the divalinyl ester can be considered in water. Approximately 1.5 mg of L-dC-3',5'-divalinyl ester hydrochloride was dissolved in 2.2 mL of MilliQ water (A', pH 6.5) saturated with octanol-1 (B). To 1 mL of this solution, 1 mL of octanol-1 (B) saturated with MilliQ water (A') was added. The resultant mixture was shaken and centrifiged; three samples from each phase was collected and analyzed by HPLC, as shown in Table 13. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. It was found that the log P' of the 3',5'-divaline under these conditions was −2.72, indicating the strong effect of the counter ions in the phosphate buffer. No conversion of the divaline to the monoesters or L-dC was observed in either the aqueous or organic phases.

TABLE 13

| | Study 1 | | | | | | Study 2 | | | | | |
|---|---|---|---|---|---|---|---|---|---|---|---|---|
| | $A^{1'}$ | $A^{2'}$ | $A^{3'}$ | $B^1$ | $B^2$ | $B^3$ | $A^{1'}$ | $A^{2'}$ | $A^{3'}$ | $B^1$ | $B^2$ | $B^3$ |
| Area | 3278293 | 3292150 | 3282281 | 5484 | 5776 | 6496 | 3282927 | 3327122 | 3297985 | 5829 | 5615 | 6139 |
| Average | 3284241 | | | 5919 | | | 3302678 | | | 5861 | | |
| P' (B/A') | $1.80 \times 10^{-3}$ | | | | | | $1.77 \times 10^{-3}$ | | | | | |
| Log P' | −2.7 | | | | | | −2.75 | | | | | |

Similarly, approximately 1.5 mg of L-dC-5'-valinyl ester hydrochloride was dissolved in 2.2 mL of MilliQ water (A', pH 6.5) saturated with octanol-1 (B). To 1 mL of this solution, 1 mL of octanol-1 (B) saturated with MilliQ water (A') was added. The resultant mixture was shaken and centrifuged; three samples from each phase was collected and analyzed by HPLC, as shown in Table 14. The HPLC was run on a Nova-Pack C18 column (3.9×150 mm) on a gradient of 0 to 25% of $CH_3CN$ in 20 mM triethylammonium acetate buffer (TEAAc) programmed over a fifteen minute period with a flow rate of 1 mL per minute. It was found that the log P of the 5'-valine under these conditions was −2.75, again a value lower than found in the log P study using the phosphate buffer.

TABLE 14

| | Study 1 | | | | | | Study 2 | | | | | |
|---|---|---|---|---|---|---|---|---|---|---|---|---|
| | $A^{1'}$ | $A^{2'}$ | $A^{3'}$ | $B^1$ | $B^2$ | $B^3$ | $A^{1'}$ | $A^{2'}$ | $A^{3'}$ | $B^1$ | $B^2$ | $B^3$ |
| Area | 3722494 | 3771963 | 3788317 | 6545 | 5082 | / | 3619900 | 3975353 | 4062284 | 8484 | 9454 | 5877 |
| Average | | 3760924 | | | 5813 | | | 3885845 | | | 7938 | |
| P' (B/A') | | $1.54 \times 10^{-3}$ | | | | | | $2.04 \times 10^{-3}$ | | | | |
| log P' | | −2.81 | | | | | | −2.69 | | | | |

Under these conditions, the log P' values for L-dC-5'-valinyl ester hydrochloride and L-dC-3',5'-divalinyl ester hydrochloride are very similar (Table 15).

TABLE 15

| Compound | log P (octanol/water) | log P' (octanol/water) |
|---|---|---|
| L-dC-5'-valine ester hydrochloride | −1.42 | −2.75 |
| L-dC-3',5'-divaline ester hydrochloride | −0.86 | −2.72 |

Example 15

Stability Study at pH 7.4

The rate of decomposition of each metabolite of L-dC-3'-valine ester hydrochloride was calculated. The half-life of L-dC-3'-valine ester hydrochloride at pH of 7.40 was determined to be 7 hours in a 0.2M Tris-HCl solution at 37° C. In these conditions, L-dC-3'-valine ester hydrochloride is simply transformed to L-dC. No cytosine was detected, thus, there was no detectable glycoside bond breakage.

Similarly, the rate of decomposition of each metabolite of L-dC-3',5'-divaline ester hydrochloride was calculated. The half-life of L-dC-3',5'-divaline ester hydrochloride at pH of 7.42 was determined to be 2.4 hours in a 0.2M Tris-HCl solution at 37° C. In these conditions, L-dC-3',5'-divaline ester hydrochloride is partially hydrolyzed into the 3'- and 5'-valinyl-L-dC, which are later transformed into L-dC. No cytosine was detected, thus, there was no detectable glycoside bond breakage (Scheme 4, FIGS. 9a and 9b).

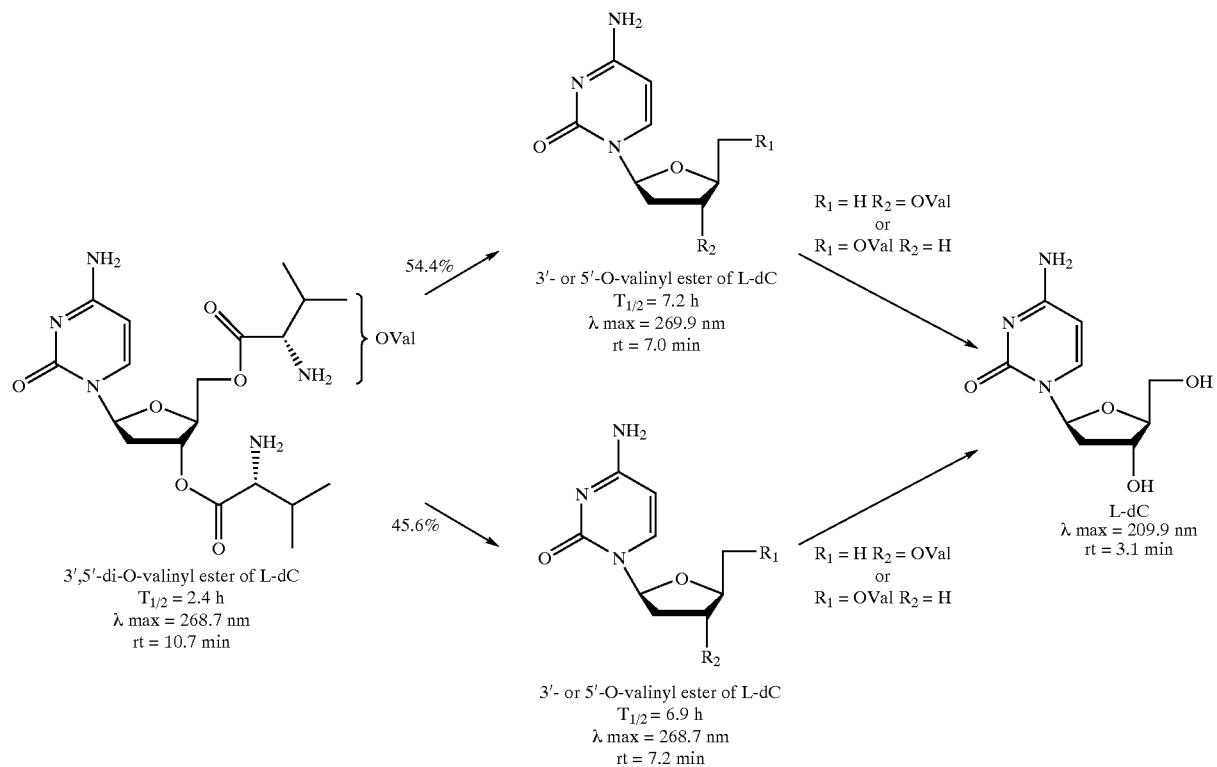

Scheme 4

Example 16

Stability Study at pH 7.20

The half-life of L-dC-3',5'-divaline ester hydrochloride at pH of 7.20 was determined to be 2.2 hours in a 20 mM phosphate buffer. In these conditions, L-dC-3',5'-divaline ester hydrochloride is partially hydrolyzed into the 3'- and 5'-valinyl-L-dC, which are later transformed into L-dC. No cytosine was detected, thus, there was no detectable glycoside bond breakage (Scheme 5, FIGS. 10a and 10b).

Similarly, stability studies were done on L-dC-5'-valine ester hydrochloride. This compound is fully stable at a pH of 1.2, with no other metabolites or decomposition products detected for up to 23 hours. No glycosidic bond breakage was detected up to 2 days in solution.

The 3',5'-diacetyl ester of L-dC was found to have a half life at a pH of 1.2 of 11.2 hours. Under these conditions the compound was partially hydrolyzed into the 3'- or 5'-derivatives, which were later transformed into L-dC. No glycoside bond breakage was detected up to 2 days in solution.

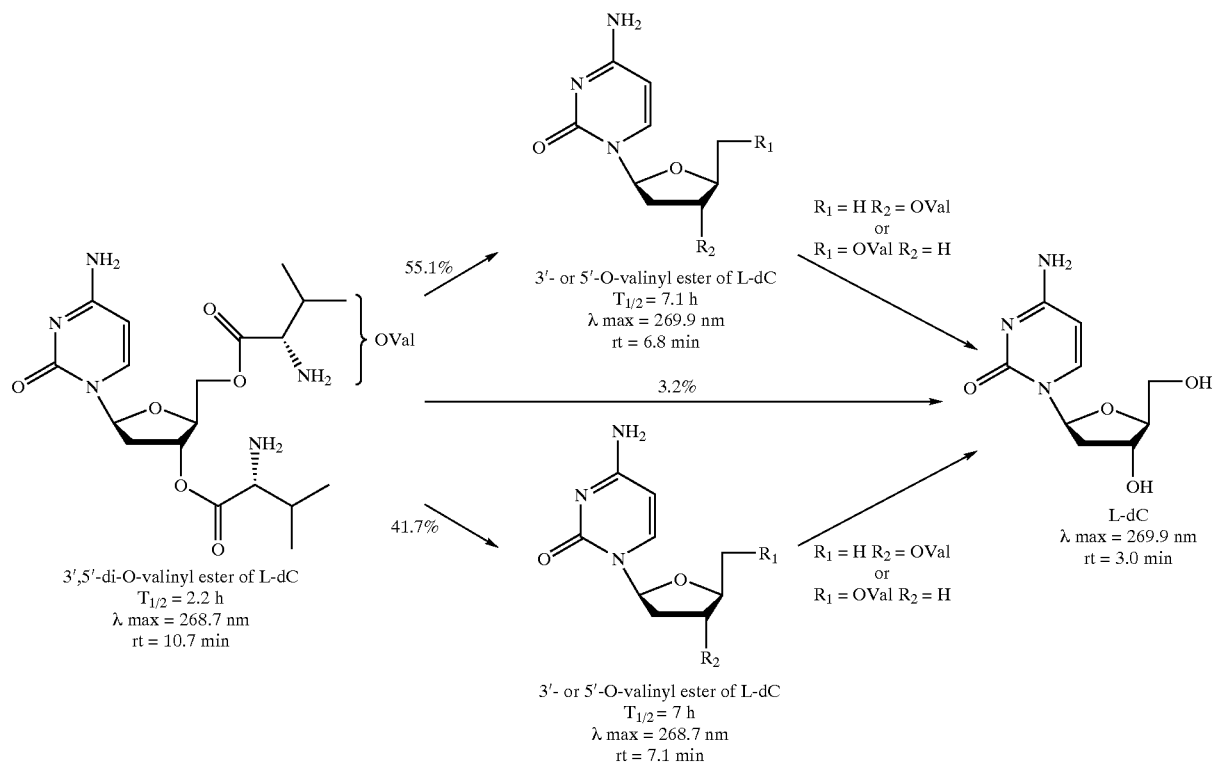

Scheme 5

Example 17

Stability Study at pH 4.5

The half-life of L-dC-3'-valine ester hydrochloride at pH of 4.5 was determined to be 8.6 days in a 20 mM acetate buffer. Again, L-dC-3'-valine ester hydrochloride is simply transformed to L-dC. No cytosine was detected, thus, there was no detectable glycoside bond breakage.

Similarly, the half-life of L-dC-3',5'-divaline ester hydrochloride at pH of 4.51 was determined to be 44 hours in a 20 mM acetate buffer. In these conditions, L-dC-3',5'-divaline ester hydrochloride is partially hydrolyzed into the 3'- and 5'-valinyl-L-dC, which are later transformed into L-dC. No cytosine was detected, thus, there was no detectable glycoside bond breakage (FIGS. 11a and 11b).

Example 18

Stability Study at pH 1.2

The half-life of L-dC-3'-valine ester hydrochloride at pH of 1.2 was determined to be greater than 48 hours in a 135 mM KCl-HCl buffer solution. No cytosine was detected, thus, there was no detectable glycoside bond breakage.

The 3',5'-divalinyl ester of L-dC was found to be fully stable at a pH of 1.23 since no other compounds were detected up to 48 hours in these conditions. No glycoside bond breakage was detected up to 2 days in solution (FIG. 12).

Alternatively, when the $N^4$ position of L-dC is masked with dimethylamino-methylene or acetyl, the half-life of the compound at a pH of 1.2 is only 26 minutes or 50 minutes, respectively.

Example 19

Single Dose Bioavailability of L-dC in the Cynomologus Monkey

The pharmacokinetics of L-dC following IV and oral administration of L-dC to cynomologus monkeys was determined. In this study, 10 mg/kg tritium ([3H]) radiolabeled L-dC was administered to three cynomologus monkeys as a single IV dose. Following a six week washout period, the same three monkeys received an identical oral dose of L-dC. Blood samples for pharmacokinetic analysis were collected pre-dose and at 0.25, 0.5, 1, 2, 3, 6, 8 and 24 hours after dosing. Urine samples for pharmacokinetic analyses were collected via pan catch pre-dose and over the following intervals post-dose: 0–2, 2–4, 4–8, and 8–12 hours, and then over 12-hour intervals thereafter through 336 hours post-dose. The drug was detected and the concentration determined using a reverse-phase high-performance liquid chromatography technique. The blood and urine drug level data were analyzed by a non-modeling mathematical method and AUC's derived by the linear trapezoidal rule.

Intravenous administration of L-dC. The mean $C_{max}$ of L-dC after IV administration was 95.7 μM and occurred at the earliest sampling time (15 minutes post-dose) for all animals. L-dC plasma concentrations decreased over time following the IV bolus with a mean t½ of 1.59 hours. The total clearance (CL) and renal clearance (CLR) of L-dC following IV administration averaged 0.53 L/h/kg and 0.46 L/h/kg, respectively. The mean apparent volume of distribution ($V_d$) of 1.22 L/kg indicated that L-dC had a significant extravascular tissue distribution.

Urinary excretion was rapid, with 71% of the administered dose recovered within 2 hours. L-dC accounted for the majority (94%) of the dose recovered in the urine. The renal clearance (0.46 L/h/kg) accounted for 87% of total L-dC clearance and suggested that renal excretion was the major route of elimination.

L-dU was detected in the plasma and urine, indicating that metabolic elimination of L-dC also occurred following IV administration. Low levels of L-dU were detected in plasma at the limit of detection (lower limit of detection (LLOD)= 0.1 μM). Renal excretion of L-dU was 4.0% of the total dose recovered in urine. With the exception of L-dU, no other metabolites were detected in the plasma or urine.

Oral administration of L-dC. The Cmax was 3.38 μM and occurred at a Tmax of 2.33 hours. The plasma concentration of L-dC declined in a biphasic manner with a mean terminal t½ of 2.95 hours and was below detection limits by 24 hours in all monkeys. L-dC was absorbed from the gastrointestinal tract with a mean oral bioavailability (F) of 16.4%.

L-dU was detected in the plasma and urine, which suggested that metabolic elimination of L-dC occurred following oral administration. Low levels of L-dU were detected in plasma at the LLOD. With the exception of L-dU, no other metabolites were detected in the plasma or urine.

Approximately 8.5% of the administered oral dose was recovered in the urine within 12 hours. After 72 hours 15.5%±8% was recovered. L-dC accounted for the majority (~69%) of drug excreted in the urine. Renal excretion of L-dU was 29% of the total recovered dose. Feces were not collected.

Table 16 presents a summary of pharmacokinetic results for IV and oral administration of L-dC in cynomologus monkeys.

Example 20

Single-Dose Bioavailability of L-dC in the Rhesus Monkey

The pharmacokinetics of L-dC following oral administration in the rhesus monkey was determined. In this study, 10 mg/kg [3H] radiolabeled L-dC was administered to three rhesus monkeys as a single oral dose. Blood samples for pharmacokinetic analysis were collected pre-dose and at 0.25, 0.5, 1, 2, 3, 6, 8 and 24 hours after dosing. Urine samples for pharmacokinetic analyses were collected via pan catch pre-dose and over the following intervals post-dose: 0–2, 2–4, 4–8 and 8–12 hours, and then at 12-hour intervals thereafter through 336 hours post-dose. The drug was detected and concentration determined using a reverse-phase HPLC technique. The blood and urine drug level data were analyzed by a non-modeling mathematical method and AUCs derived by the linear trapezoidal rule.

The average $AUC_{0.25 \to 8}$ and $C_{max}$ values were 12.2 mgM.h and 3.23 mgM, respectively. The Cmax occurred at a Tmax of 0.83 hours. The mean $t_{1/2}$ was 3.34 hours and the L-dC plasma concentration was below detection levels by 24 hours in all monkeys.

The mean renal clearance of L-dC was 0.273 L/h/kg. No metabolites were observed in the plasma of monkeys receiving L-dC.

Approximately 8.5% of the administered oral dose (oral bioavailability of L-dC ~16%) was recovered in the urine within 8 hours. After 48 hours 15% was recovered. L-dC accounted for the majority (~77%) of drug excreted in the urine. Renal excretion of L-dU was 23% of the total recovered dose. With the exception of L-dU, no other metabolites were detected.

The AUC and Cmax for L-dC after oral administration to rhesus monkeys were similar to that observed in cynomologus monkeys.

Example 21

Single-Dose Bioavailability of L-dC in the Rat

The pharmacokinetics and bioavailability of L-dC in rats was determined. In this study, 10 mg/kg [3H] radiolabeled L-dC was administered to three female Sprague-Dawley rats as a single IV dose. A second group of three animals received an identical oral dose of L-dC. Blood samples for pharmacokinetic analyses were collected at 0.17, 0.33, 0.5, 1, 2, 3, 4, 6, 8 and 24 hours after dosing. Urine was also collected at 8 and 24 hours after dosing. The drug was detected and the concentration determined in plasma and urine using a reverse-phase HPLC technique. The data were analyzed by a non-modeling mathematical method and the AUCs derived by the linear trapezoidal rule.

TABLE 16

Pharmacokinetic Analysis after Intravenous and Oral Administration of L-dC (10 mg/kg) in the Cynomologus Monkey

| Route (h) | $AUC_{last}$ (mM-h) | $t_{1/2}$ (h) | $C_{max}$ (mM) | $T_{max}$ (h) | CL (L/h/kg) | $CL_R$ (L/h/kg) | $V_d$ (L/kg) | F (%) |
|---|---|---|---|---|---|---|---|---|
| IV (3) | 81.1 (±5.7) | 1.59 (±0.09) | 95.7 (±13) | 0 | 0.53 (±0.04) | 0.46 | 1.22 (±0.11) | — |
| Oral (3) | 13.7 (±4.3) | 2.95 (±1.3) | 3.38 (±1.3) | 2.33 (±1.5) | — | — | — | 16.4 (±5.0) |

Mean value (±SD).

Intravenous administration of L-dC. The average $AUC_{0.25\to 8}$ value was 30.1 mM.h. The Cmax of L-dC was 91.1 mgM and occurred at the earliest sampling time (10 minutes post-dose) for all animals. L-dC plasma concentrations declined in a biphasic manner following the IV bolus with a mean t½ of 1.21 hours. The CL of L-dC averaged 1.44 L/h/kg. The mean Vd of 2.53 L/kg indicated that L-dC had a significant extravascular tissue distribution. No metabolites were observed in the plasma of rats receiving L-dC.

L-dC accounted for the majority of radioactivity recovered in the urine. L-dU was detected in the urine, which suggested that metabolic elimination of L-dC occurred following IV administration.

Oral administration of L-dC. The average $AUC_{0.25\to 8}$ value was 4.77 mM.h. The mean Cmax was 1.50 mgM and occurred at a Tmax of 1.0 hour. The plasma concentration of L-dC declined with a t½ of 2.52 hours. L-dC had limited uptake from the gastrointestinal tract with a mean oral bioavailability (F) of 15.4%. No metabolites were observed in the plasma of rats following oral administration of L-dC.

L-dC accounted for the majority of radioactivity recovered in the urine. L-dU was detected in the plasma and urine, which suggested that metabolic elimination of L-dC occurs following oral administration.

TABLE 17

Pharmacokinetic Analysis after Intravenous and Oral Administration of L-dC (10 mg/kg) in the Rat

| Route (h) | $AUC_{0\text{-}25\text{-}28}$ (mM-h) | $t_{1/2}$ (h) | $C_{max}$ (mM) | $T_{max}$ (h) | CL (L/h/kg) | $V_d$ (L/kg) | F (%) |
|---|---|---|---|---|---|---|---|
| IV (3) | 30.1 (±4.7) | 1.21 (±0.06) | 91.1 (±6.6) | 0 | 1.44 (±0.29) | 2.53 (±0.60) | — |
| Oral (3) | 4.77 (±2.1) | 2.52 (±1.3) | 1.50 (±0.68) | 1.0 | — | — | 15.4 (±4.6) |

Mean value (±SD).

Example 22

Single-Dose Bioavailability of L-dC in the Woodchuck

The pharmacokinetics and bioavailability of L-dC in woodchucks was determined. In this study, 10 mg/kg [3H] radiolabeled L-dC was administered to three woodchucks as a single IV dose. Blood samples for pharmacokinetic analyses were collected at 2, 5, 15, and 30 minutes and 1.0, 1.5, 2.0, 3.0, 4.0, and 24 hours post-dose. After a seven-day washout period, the same animals received 10 mg/kg L-dC as a single oral dose. Blood samples for pharmacokinetic analyses were collected at 15 and 30 minutes and 1.0, 1.5, 2.0, 3.0, 4.0, 8.0, and 24 hours post-dose. Urine was collected over the 24-hour post-dose period. Plasma drug levels, CL, $t_{1/2}$ and F were determined. Drug levels were determined using an HPLC method with in-line radioactivity detection and scintillation counting.

Intravenous administration of L-dC. The mean $C_{max}$ of L-dC was 112 μM and occurred at the earliest sampling time (2 minutes post-dose) for all animals. L-dC plasma concentrations declined in a biphasic manner following the IV bolus with a mean t½ of 2.85 hours. The CL of L-dC averaged 0.39 L/h/kg. The mean $V_d$ was 1.17 L/kg. L-dC accounted for the majority of radioactivity recovered in the urine. L-dU was detected in the plasma and urine, indicating that metabolic elimination of L-dC occurred following IV administration. The levels of L-dU detected intermittently in plasma were at or below the limit of assay quantitation with a mean $C_{max}$ of 0.75 μM.

Oral administration of L-dC. The $C_{max}$ was 1.37 μM and occurred at a Tmax of 3 hours. L-dC plasma concentrations decreased with a mean t½ of 5.22 hours. L-dC was absorbed from the gastrointestinal tract with an oral bioavailability ranging from 5.60 to 16.9% with an average of 9.57%. L-dC accounted for the majority of radioactivity recovered in the urine. L-dU was detected in the plasma and urine, indicating that metabolic elimination of L-dC occurred following oral administration. L-dU in the plasma was near the limit of quantitation with a mean Cmax of 0.19 μM.

Table 18 presents a summary of pharmacokinetic results for both IV and oral L-dC.

TABLE 18

Pharmacokinetic Analysis of L-dC (10 mg/kg) after Intravenous and Oral Administration in the Woodchuck

| Route (n) | $AUC_{t\to 24}{}^a$ (μM · h)) | $t_{1/2}$ (h) | $C_{max}$ (μM) | $T_{max}$ (h) | CL (L/h/kg) | $V_d$ (L/kg) | F (%) |
|---|---|---|---|---|---|---|---|
| IV (3) | 174 (±120)[b] | 2.85 (±130) | 112 (±33) | 0 | 0.39 (±0.3) | 1.17 (±0.36) | — |
| PG (3) | 11.3 (±4.7) | 5.22 (±2.7) | 1.37 (±0.22) | 3.0 (±1) | — | — | 9.57 (±6.4) |

[a]t = 0.033 hours for IV administration and 0.25 hours for PG administration
[b]Mean value (±SD)

Example 23

Bioavailability of the Prodrugs of L-dC

The bioavailability of L-dC, the 5'-monoester of L-dC, the divaline ester of L-dC, and the diacetyl ester of L-dC was evaluated in cynamologous monkeys, with and without L-dT. When the divaline ester of L-dC was orally administered to monkeys, approximately 73% of the dose was absorbed. Of the absorbed divaline ester of L-dC, more than 99% was rapidly converted to L-dC to give a high concentration of L-dC in the plasma and no detectable divaline ester of L-dC. A low plasma concentration of the monovaline ester of L-dC was detected early after oral administration of divaline ester of L-dC. A low plasma concentration of β-L-2'-deoxyuridine (L-dU) was detected intermittently. No other metabolites were detected. The results are provided in Table 19. As indicated, the combination of the 3',5'-divalyl ester of L-dC with L-dT provided the largest bioavailability of L-dC.

TABLE 19

|  | L-dC parent (mw = 227.22) | L-dC[3] 5'-valine (mw = 399.27) | L-dC 3'-valine (mw = 399.27) | L-dC di-valine (mw = 534.87) | L-dC di-acetyl (mw = 347.75) |
|---|---|---|---|---|---|
| % BA[1] | 16.4 ± 5.0 | 39.0 ± 11.4 | 85.1 ± 24.5 | 72.7 ± 22.0 | 23.0 ± 6.5 |
| % BA w/ L-dT[2] | 11.9 ± 1.7 | ND | ND | 74.6 ± 9.9 | 24.9 ± 4.0 |

[1]estimated relative to AUC of L-dC (oral dose)
[2]coadministered with 10 mg/kg L-dT
[3]Specific Activity 5'-mono-valine study based on total radioactive dose
ND, not determined
Purity = 87% L-dC-mono-valine, 12% L-dC Example 24

Single Dose Bioavailability of Dival-L-dC in Cynomologus Monkey

Three make non-naive cynomologus monkeys (macaca fascicularis) received 10 mg/kg of dival-L-dC intravenously with a tracer amount of tritium ([3H]⁻) labeled drub (250 µCi) dissolved in sterile 9.0% saline. Following a 6 week washout period, the same three animals received an identical oral dose of dival-L-dC. Blood samples were collected in heparinized tubes at pre-dose (~18 hours) and 0.25, 0.50, 1, 2, 3, 4, 6, 8, and 24 hours after dosing. Urine was also collected from 0–2, 2–4, 4–8, 8–12 and then at 12-hour intervals until 336 hours post-dose. The drug was quantitated in plasma and urine with a liquid chromatography-mass spectrometry (LC-MS) technique. After administration of dival-L-dC, the plasma concentration time course of L-dC was analyzed by a non-modeling mathematical method and the area under the time-concentration curves (AUC) derived by the linear trapezoidal rule. The bioavailability (F) of L-dC following IV and PO administration of dival-L-dC was calculated from the L-dC AUCs, where F=AUCpo/AUCiv× doseiv/dosepo.

Intravenously administered dival-L-dC was converted rapidly to L-dC following intravenous administration. Dival-L-dC was detected in the plasma at 15 minutes (1.39 µM) and at 30 minutes (0.36 µM, 1 of 3 animals) [lower limit of quantitation (LLOQ)=0.23 µM or 100 ng/mL]. Dival-L-dC was not detected in the plasma after 30 minutes post-dosing. The partially de-esterified form of dival-L-dC, β-L-2'-deoxycytidine-5'-valine ester, was detected in plasma at 15 minutes (3.23 µM) and decreased in concentration to 0.08 µM by 2 hours (LLOQ=0.031 µM or 10 ng/mL). L-dC represented the majority of drug present in the plasma following intravenous administration. The average $AUC_{0.25\rightarrow 8}$ value for L-dC was 19.8 µM·h. The mean peak plasma concentration ($C_{max}$) of L-dC was 24.6 µM (LLOQ= 0.088 µM or 20 ng/mL) and occurred at the earliest sampling time (15 minutes post-dose) in all animals. The plasma concentration of L-dC declined in a biphasic manner with a mean $t_{1/2}$ of 1.73 hours. The total body clearance (CL) and apparent volume of distribution ($V_d$) of L-dC averaged 1.01 L/h/kg and 2.46 L/kg, respectively, indicating that L-dC had significant extravascular tissue distribution. The binding of dival-L-dC and L-dC to human plasma proteins ex vivo was 13.3%±2.6% and 19.7%±5.9%, respectively. The impact of human plasma protein binding on dival-L-dC and L-dC free-drug levels was minimal, suggesting that drug interactions involving binding site displacement are not anticipated.

Urinary excretion was rapid with 58±3% of the administered dose of dival-L-dC excreted within 2 hours following intravenous administration. L-dC accounted for the majority (~93%) of drug excreted in the urine. L-dU was also detected in the plasma and urine. This suggested that metabolic elimination of L-dC also occurs following administration of dival-L-dC. Low levels of L-dU were detected in plasma at intermittent time points in two of three animals at concentrations ranging from 0.22 µM to 0.88 µM (LLOQ= 0.22 µM or 50 ng/mL). There were no detectable levels of L-dU at any time point in the third monkey. Renal excretion of L-dU and the partially de-esterified form of dival-L-dC, β-L-2'-deoxycytidine-5'-valine ester was minor, accounting for approximately 2.5% and 3.7% of the total recovered dose, respectively. Dival-L-dC was detected in the urine of one of three animals at 2 hours following IV administration, which accounted for approximately 0.15% of the recovered dose.

Because of the intermittent low concentrations of both the monovaline esters and L-dU in the plasma and urine, it was not feasible to perform pharmacokinetic analysis of these metabolites. The appearance of the monovaline ester of dival-L-dC was not unexpected as it represents and intermediate in the conversion of dival-L-dC to L-dC. In addition, in vitro cellular metabolism studies in monkey, rat and human primary hepatocytes and in extracts of HepG2 cells demonstrated that L-dC was not directly deaminated to L-dU but that L-dC monophosphate (-MP) is converted to L-dU-MP, which is either activated to L-dU disphosphate (-DP), and triphosphate (-TP), or metabolized to L-dU, which is then detected in the extracellular compartment (plasma). L-dU was non-cytotoxic ($CC_{50}$>200 µM) and L-dU-TP had an $IC_{50}$ in vitro against hepatitis B virus deoxyribonucleic acid (DNA) polymerase of 5.26 µM (see Microbiology and Virology, Section 10).

Orally administered dival-L-dC also was converted rapidly to L-dC following oral administration and was not detectable in plasma samples at any time point (LLOQ of dival-L-dC in solution=0.23 µM or 100 ng/mL). The partially de-esterified metabolite of dival-L-dC, β-L-2'-deoxycytidine-5'-valine ester, was detected in plasma at 30 minutes and 1 hour at concentrations ranging from 0.034 β to 0.107 β (LLOQ of monoester in solution=0.031 µM or 10 ng/mL). Dival-L-dC was not detected in the plasma.

L-dC represented the majority (>99% at $C_{max}$) of the plasma drug levels following oral administration of dival-L-dC. The average $AUC_{0.25\rightarrow 8}$ value for L-dC was 14.0 µM h. The $C_{max}$ of L-dC was 8.26 µM (LLOQ of L-dC in solution=0.088 µM or 20 ng/mL) and occurred at 0.67 hours following administration of dival-L-dC. The plasma concentration of L-dC declined in a biphasic manner with a mean $t_{1/2}$ of 2.28 hours. The mean oral bioavailability of L-dC following administration of dival-L-dC was 72.7%±22%.

L-dU was also detected in the plasma indicating the metabolic elimination of L-dC occurs following oral administration of dival-L-dC. Low levels of L-dU were detectable in the plasma from 30 minutes to 4 hours in two of three animals of concentrations ranging from 0.24 μM to 0.66 μM (LLOQ of L-dU in solution=0.22 μM or 50 ng/mL) and in one animal only at 8 hours at a concentration of 0.39 μM.

After oral administration, dival-L-dC was rapidly absorbed from the gastrointestinal tract and converted to L-dC by first-pass intestinal and/or hepatic metabolism. Neither dival-L-dC nor L-dC metabolism was associated with liver microsomal enzymes. Following administration of high dose levels of dival-L-dC, the monovaline ester of L-dC was transiently detected prior to conversion to L-dC. No dival-L-dC was detected after oral administration. Intermittent low plasma levels of L-dU were detected at, or below, the lower limit of assay quantitation. L-dU was formed by deamination of L-dC following cellular uptake of L-dC.

Approximately 31±8% of the administered oral dose was recovered in the urine within 4 hours. After 72 hours 39±8% was recovered. L-dC accounted for the majority (~95%) of drug excreted in the urine. Renal excretion of L-dU and the partially de-esterified form of dival-L-dC, β-L-2'-deoxycytidine-5'-valine ester was minor, accounting for approximately 2.5% and 0.2% of the total recovered dose, respectively. No dival-L-dC was detected in the urine.

Table 20 represents a summary of pharmacokinetic results for L-dC following both IV and oral dosing of dival-L-dC.

Example 25

Oral Bioavailability of L-dC via Dival-L-dC in Cynomologus Monkey

Three male non-naive cynomologus monkeys (macaca fascicularis) received 10 mg/kg of dival-L-dC orally with a tracer amount of [3H]-labeled drug (250 μCi) dissolved in sterile 0.9% saline. Blood samples were collected in heparinized tubes at pre-dose (~18 hours) and 0.25, 0.50, 1, 2, 3, 4, 6, 8 and 24 hours after dosing. Urine was collected from 0–2, 2–4, 4–8, 8–12 and then at 12-hour intervals until 336 hours post-dose. The drug was quantitated in plasma and in urine using HPLC analysis. After administration of dival-L-dC the plasma concentration time course of L-dC was analyzed by a non-modeling tot mathematical method and the area under the time-concentration curves (AUC) derived by the linear trapezoidal rule. Dival-L-dC was rapidly absorbed and converted to L-dC following oral administration. Radiochromatographic high pressure liquid chromatography (HPLC) analysis of plasma samples confirmed that the majority of the recovered radioactivity was L-dC. Dival-L-dC was detected in only one animal at 15 minutes postdose at a concentration of 0.35 μM. The partially de-esterified form of dival-L-dC, β-L-2'-deoxycytidine-5'-valine ester, was not detected in the plasma or urine. Approximately 26% of the administered oral dose was recovered in the urine within 8 hours. After 72 hours 31% was recovered. L-dC accounted for the majority (~89%) of drug excreted in the urine. Renal excretion of L-dU was minor, accounting for approximately 10% of the recovered

TABLE 20

Pharmacokinetic Analysis after Intravenous and Oral Administration of Dival-L-dC (10 mg/kg) in Cynomologus Monkeys
Pharmacokinetic Parameter[2]

| Route (n) | $AUC_{0.25 \rightarrow 8}$ (μM h) | $t_{1/2}$ (h) | $C_{max}$ (μM) | $T_{max}$ (h) | CL (L/h/kg) | $V_d$ (L/kg) | F (%) |
|---|---|---|---|---|---|---|---|
| IV (3) | 19.8 (±5.2) | 1.73 (±0.33) | 24.6 (±2.6) | 0 | 1.01 (±0.32) | 2.46 (±0.47) | |
| Oral (3) | 14.0 (±2.4) | 2.28 (±1.4) | 8.26 (±0.71) | 0.67 (±0.3) | | | 72.7 (±22) |

[3] Mean value [± standard deviation (SD)].

Table 21 presents a schematic of metabolite formation form dival-L-dC, the monovaline derivative of L-dC, L-dC and L-dU following IV and oral administration of dival-L-dC. The $C_{max}$ of each metabolite is also noted.

TABLE 21

Metabolite Formation for IV and PO Administration of Dival-L-dC

| Intravenous (10 mg/kg Dival-L-dC) | | | | |
|---|---|---|---|---|
| | dival-L-dC→ | mono-val-L-dC→ | L-dC→→ | L-dU |
| $C_{max}$ | 1.39 μM | 3.23 μM | 24.6 μM | 0.88 μM |

| Oral (10 mg/kg dival-L-dC) | | | | |
|---|---|---|---|---|
| | val-L-dC→ | mono-val-L-dC→ | L-dC→→ | L-dU |
| $C_{max}$ | Not detected | 0.11 μM | 8.26 μM | 0.66 μM | dose. No dival-L-dC or its partially de-esterified form, and no other metabolites were detected in the urine.

The overall pharmacokinetic profile was comparable to that determined in the pharmacokinetic study as demonstrated by similar $C_{max}$ to AUC ratios. Low levels of L-dU were detected in the plasma in two of three animals with an average $C_{max}$ of 0.33 μM. No L-dU was detected in the plasma of the third animal. The level of L-dU was at or below the limit of quantitation, precluding pharmacokinetic analysis.

Example 26

In Vitro Metabolism of Dival-L-dC

Studies were conducted to determine the stability and protein binding of dival-L-dC and its de-esterified metabolites in human plasma. Dival-L-dC was incubated in human plasma at 37° C. and samples analyzed at various time points up to 24 hours (FIG. 13). No dival-L-dC was detectable at 24 horns with complete conversion to L-dC. Two additional metabolites (β-L-2'-deoxycytidine-5'-valine ester and β-L-2'-deoxycytidine-valine ester) were also noted. The transient nature of these metabolites indicated that they are intermediates in the conversion of dival-L-dC to L-dC. The in vitro half-life of dival-L-dC in human plasma at 37° C. was determined to be approximately 39 min.

The impact of human plasma protein binding on free levels of dival-L-dC and L-dC was also investigated using an ultrafiltration method. Plasma protein binding of dival-L-dC was 13.3%±2.6%. The binding of L-dC to plasma proteins was 19.7%±5.9%. This study shows that the impact of human plasma protein binding on dival-L-dC and L-dC is minimal and suggests that drug interactions involving binding site displacement are not anticipated.

Example 27

Metabolic Activation and Intracellular Profile of L-dC

The cellular metabolism of L-dC was examined using HepG2 cells and human primary hepatocytes. High pressure liquid chromatography (HPLC) analysis demonstrated that L-dC was extensively phosphorylated in hepatocytes. The predominant metabolite in HepG2 cells exposed to 10 μM L-dC for 24 hours was L-dC-TP which reached 72.4±1.8 μM (see Table 23). In primary human hepatocytes, the L-dC-TP concentration at 24 hours was 90.1±37 μM, similar to the level of phosphorylation in HepG2 cells. Exposure of hepatocytes to L-dC led to activation of a second 5'-triphosphate derivative, L-dU-TP. In HepG2 cells exposed to 10 μM L-dC, the L-dU-TP level reached 18.2 μM (43.5 pM in primary human hepatocytes) at 24 hours. In primary rat and monkey hepatocytes the extent of phosphorylation of L-dC was slightly lower.

Example 28

Cellular Kinases Associated with Metabolic Activation

D-Deoxycytidine (dCyd) is a natural substrate of cytosolic dCyd kinase (dCK) and mitochondrial thymidine kinase (TK2) for conversion to dCyd-5'-monophosphate (dCMP). Cytosolic thymidine kinase (TK1) and TK2 utilize D-thymidine (Thd) as a natural substrate for conversion to Thd-5'-monophosphate (TMP). The cellular kinase involved in the initial phosphorylation of L-dC was identified in competition studies using L-dC and the natural endogenous Thd and dCyd. Intracellular phosphorylation of L-dC was decreased in a dose-dependent fashion by dCyd but not by Thd. Thus, dCyd acted as an inhibitor of L-dC phosphorylation. The change in intracellular phosphorylation of L-dC was similar when HepG2 cells were exposed to both Thd and dCyd or dCyd alone. The inhibition of L-dC phosphorylation by only the natural deoxypyrimidine, dCyd, suggested that dCK was involved in L-dC phosphorylation.

The role of these pyrimidine nucleoside kinase activities in the phosphorylation of L-dC was further investigated in kinase deficient cell lines. There was a significant decrease in the mount of phosphorylated metabolites of L-dC in dCK deficient cells. However, no significant difference was observed in L-dC phosphorylation in TK1 deficient cells. These data were consistent with the competition studies described above and indicated that dCK plays a critical role in the phosphorylation of L-dC to L-dC-MP.

Using cytosolic extracts of HepG2 cells as an enzyme source, steady state kinetics for L-dC, Thd, and dCyd phosphorylation were similar as indicated by the apparent

TABLE 23

Activation of L-dC (10 μM) in Hepatocytes

| Cells[a] | n | L-dC-MP | L-dU-MP | L-dC-DP | L-dC-DP-choline | L-dU-DP | L-dC-TP | L-dU-TP |
|---|---|---|---|---|---|---|---|---|
| HepG2 | 3 | 23.3 ± 0.86 | 6.73 ± 0.41 | 10.2 ± 1.9 | 25.6 ± 0.08 | 2.69 ± 0.45 | 72.4 ± 1.8 | 18.2 ± 1.0 |
| Human Primary Hepatocytes | 3 | 27.6 ± 15 | 5.74 ± 2.4 | 7.19 ± 2.3 | 15.8 ± 1.8 | 3.93 ± 1.6 | 90.1 ± 37 | 43.5 ± 27 |
| Monkey Primary Hepatocytes | 1 | 11.2 | 2.54 | 7.66 | 10.4 | 3.11 | 39.3 | 21.9 |
| Rats Primary Hepatocytes | 3 | 5.09 ± 2.1 | 3.53 ± 0.97 | 1.52 ± 0.38 | 8.82 ± 3.1 | 7.90 ± 1.4 | 14.2 ± 3.1 | 46.9 ± 5.2 |

[a]Cells were incubated for 24 hours with [$^3$H]-L-dC, specific activity: HepG2 assay = 0.5 Ci/mmol; human, monkey and rat hepatocyte assay = 1.0 Ci/mmol.

In addition to the phosphorylated derivatives of L-dC and L-dU, formation of a [β-L-2'-deoxyliponucleotide metabolite was noted. In HepG2 cells and primary hepatocyte cultures exposed to 10 μM L-dC for 24 hours, [3-L-2'-deoxycytidine-5'-diphosphocholine (L-dC-DP-choline) was detected at a concentration of 25.6 μM (range 25.6–25.7 μM) and 12.3 μM (range 8.82–15.8 μM), respectively.

The metabolic profile obtained after a 24-hour exposure of HepG2 cells to 10 μM [3H]-L-dC is shown in FIG. 14. The apparent intracellular half-life of the L-dC-TP was 15.5±0.34 hours, which correlated with prolonged antiviral activity following drug withdrawal in the virus rebound experiments. The phosphorylation pattern detected in primary human hepatocytes was qualitatively and quantitatively similar to that obtained using HepG2 cells (FIG. 15).

Michaelis-Menten constant ($K_m$) and maximum initial velocity ($V_{max}$) values (L-dC: $K_m$ of 5.75 mM and $V_{max}$, of 1.12 mmol/min/mg protein; Thd: $K_m$ of 4.06 mM and $V_{max}$ of 1.26 nmol/min/mg protein; dcyd: $K_m$ of 4.85 mM and $V_{max}$ of 2.15 nmol/min/mg protein). In addition, the efficiency of L-dC, Thd, and dCyd phosphorylation were similar as defined by their corresponding $V_{max}/K_m$ in values (0.19, 0.31, and 0.44, respectively).

In addition, the extent of intracellular phosphorylation of L-dC was compared to that of the natural endogenous substrates, Thd and dCyd in woodchuck liver extracts. This was done to support antiviral testing in the woodchuck model of chronic hepatitis B virus infection. Phosphorylation of L-dC was similar to that of the endogenous substrates. Furthermore, the level of phosphorylation of L-dC was comparable to that of L-dC and that of the endogenous substrates in human liver extracts.

Example 29

Antiviral Activity Against Hepadnavirus of L-dC

The antiviral activity of L-dC against human hepatitis B virus was measured by the reduction in extracellular HBV DNA and replicative intermediates compared to untreated control cells in the HBV-expressing hepatoma cell line 2.2.15 (see Table 24). Confirmatory testing of the antiviral activity of L-dC using a panel of ribonucleic acid (RNA) and DNA viruses was performed by the NIH Antiviral Research and Antimicrobial Chemistry Program.

L-dC did not inhibit replication of any virus other than hepadnaviruses (HBV, DHBV). L-dC had potent antiviral activity against HBV replication in vitro, reducing extracellular HBV DNA production with an $EC_{50}$ of 0.24 µM ($EC_{90}$ 1.06 µM). L-dC also reduced intracellular HBV DNA replicative intermediates (RI) with an $EC_{50}$ of 0.5 µM. Furthermore, L-dC produced a dose-dependent inhibition of duck hepatitis B virus (DHBV) DNA synthesis in primary duck hepatocyte (PDH) cultures with an $EC_{50}$ of 0.87 µM.

TABLE 24

In vitro Antiviral Activity, Selectivity and Cytotoxicity of L-dC

| Virus (Cell line) | $EC_{50}$[b] (µM) | $CC_{50}$[c] (µM) |
|---|---|---|
| HBV (2.2.15) | 0.24 ± 0.08 | >2000 |
| DHBV (PDH) | 0.87 | nd[d] |
| HIV-1 (PBMC) | >200 | >200 |
| HSV-1 (HFF)[e] | >100 | >100 |
| HSV-2(HFF)[e] | >100 | >100 |
| VZV (HFF)[e] | 18.6 | >100 |
| EBV (Daudi)[e] | >50 | >50 |
| HCMV (HFF)[e] | >100 | >100 |
| Influenza A/H1N1 (MDCK) | >100 | >100 |
| Influenza A/H3N2 (MDCK) | >100 | >100 |
| Influenza B (MDCK) | >100 | >100 |
| Measles (CV-1) | >100 | >100 |
| Parainfluenza type 3 (MA-104) | >100 | >100 |
| Rhinovirus type 5 (KB) | >100 | >100 |
| RSV type A (MA-104) | >100 | >100 |

[a]PDH, primary duck hepatocytes; PBMC, peripheral blood mononuclear cells; HFF, human foreskin fibroblast; Daudi, Burkitt's B-cell lymphoma; MDCK, canine kidney epithelial cells; CV-I, African green monkey kidney fibroblast cells; KB, human nasopharyngeal carcinoma; MA-i 04, Rhesus monkey kidney epithelial cells.
[b]$EC_{50}$ = 50% effective concentration.
[c]$CC_{50}$ = 50% cytotoxic concentration.
[d]nd = not determined.
[e]Result presented in µg/mL rather than µM.

No cytotoxicity was detected at the maximum concentrations of L-dC tested in any of the cell lines or primary cell types used to support replication of the various DNA and RNA viruses. No toxicity was seen in human PBMCs, HFF, or other cell types of mammalian origin.

Example 30

Antiviral Activity of L-dC in Woodchucks—28 Days

Woodchucks chronically infected with WHV are widely accepted as a model of HBV infection and have proven to be useful in the evaluation of anti-HBV agents. It has been proven to be a positive predictor of antiviral activity of therapies for chronic HBV infection and has served as a sensitive system for evaluation of the safety of nucleosides and their analogs.

L-dC was given orally to woodchucks once daily at 0.01 to 10 mg/kg/day for 28 days. The serum levels of WHV DNA during 28 days of drug treatment and 56 days of post-treatment follow-up were determined by DNA dot-blot hybridization (detection limit of approximately 107 genome equivalents (geq)/mL serum) and by quantitative PCR (detection limit of 300 geq/mL serum)(1). WHV DNA replication was significantly inhibited within the first few days of treatment and was maintained throughout the treatment phase. Once a day oral delivery of L-dC produced a strong antiviral effect, which was dose-dependent as determined using the DNA dot-blot hybridization assay (FIG. 16).

FIG. 17 presents the antiviral activity of L-dC for individual animals treated with 10 mg/kg/day for 28 days in the woodchuck model of chronic hepatitis B infection. Notably, in the L-dC 10 mg/kg/day treatment group, by day 14 to 28, viral load had dropped by 2–6 logs from baseline as measured by quantitative PCR assay. Following drag withdrawal, viral rebound reached near pre-treatment levels between Weeks 1 and 2.

In the lamivudine treated group (10 mg/kg/day, orally), the HBV viral load decreased by approximately 0.5 log to 1.0 log (geq/mL; data not shown) which is consistent with previous studies using similar concentrations of lamivudine, which is a cytidine nucleoside analog (30).

Example 31

Viral Rebound in L-dC Treated Cells

Viral rebound in L-dC treated 2.2.15 cells occurred after drug withdrawal. HBV replication returned to 50% of pre-treatment levels by day 18 post-treatment. The kinetics of viral rebound after L-dC treatment suggested that a significant antiviral effect continued after drug withdrawal, which was consistent with the intracellular half-life of L-dC-TP (15.5 hours in HepG2 cells).

Example 32

Antiviral Activity Against Drug-Resistant HBV of L-dC

In controlled clinical studies of lamivudine (100 mg once daily), administered to HBV-infected patients, the prevalence of YMDD-mutant HBV was 14 to 32% after one year of treatment and as much as 58% after two to three years of treatment (18–20). Mutant virus was associated with evidence of diminished treatment response relative to lamivudine-treated patients without YMDD mutations.

Genotypic analysis of viral isolates obtained from patients who showed evidence of renewed HBV replication while receiving lamivudine suggests that a reduction in HBV sensitivity to lamivudine is associated with mutations resulting in a methionine to valine or isoleucine substitution in the YMDD motif of the catalytic domain of HBV polymerase (position 552) and a leucine to methionine substitution at position 528.

HBV recombinants containing the YMDD mutation are lamivudine-resistant and slightly less replication-competent than wild-type HBV in vitro (21). The triphosphate derivative of L-dC will be tested against wild type and mutant HBV DNA polymerase to compare IC50 values. In addition, antiviral testing of L-dC against lamivudine-resistant HBV isolates and recombinant viruses with mutations at positions 552 and 528 will be performed.

In addition, selection of L-dC drug-resistant HBV mutants in vivo during chronic treatment of WHV-infected woodchucks is also being considered. The relevance of selection of drug-resistant mutants in the woodchuck in vivo model is uncertain because the spectrum of lamivudine-resistant mutants in the woodchuck does not match that identified in HBV-infected patients (20–22). A subset of this long-term study (12 to 24 months) could provide information relevant to treatment-related elimination of HBV covalently closed circular (ccc) DNA from infected hepatocytes. At the present time, it is not possible to use the DHBV in vitro model to select drug-resistant mutations because the primary duck hepatocytes used in this model cannot be sustained in cell culture for the extended periods required to select drug-resistant virus.

Example 33

Combination Antiviral Activity and Cytotoxicity of L-dT+L-dC

The anti-HBV activity and cytotoxicity of a combination of L-dT and L-dC at near equimolar ratios were tested in 2.2.15 cells and found to by synergistic at ratios of 1:1, 1:3, and 3:1 (see Table 25).

TABLE 25

Combination Antiviral Activity of L-dT + L-dC in HBV Infected 2.2.15 Cells

| Treatment | $CC_{50}{}^a$ ($\mu$M) | $EC_{90}{}^b$ ($\mu$M) | S.I.$^c$ ($CC_{50}/EC_{90}$) | CalcuSyn Analysis$^d$ (at $EC_{90}$) |
|---|---|---|---|---|
| 3TC | >1000 | 0.180 ± 0.007 | >5,000 | |
| L-dT | 3022 | 1.2 ± 0.1 | 2,518 | — |
| L-dC | 3000 ± 96 | 1.1 ± 0.1 | 2,727 | — |
| L-dT + L-dC (1:1) | >1500 | 0.297 ± 0.016 | >5,051 | Synergistic |
| L-dT + L-dC (1:3) | 1331 ± 67 | 0.333 ± 0.023 | 3,997 | Synergistic |
| L-dT + L-dC (3:1) | 2957 ± 88 | 0.409 ± 0.079 | 7,230 | Synergistic |
| L-dT + 3TC (1:1) | >1000 | 0.089 ± 0.004 | >11,000 | Synergistic |
| L-dT + 3TC (3:1) | 1000 | 0.068 ± 0.004 | 14,706 | Synergistic |
| L-dT + 3TC (10:1) | >1000 | 0.191 ± 0.017 | >5,000 | Synergistic |
| L-dC + 3TC (1:1) | >1000 | 0.200 ± 0.013 | >5,000 | Synergistic (Additive at high concentrations) |
| L-dC + 3TC (3:1) | >1000 | 0.216 ± 0.013 | >5,000 | Synergistic |
| L-dC + 3TC (10:1) | >1000 | 0.084 ± 0.006 | >11,000 | Synergistic |

$^a$$CC_{50}$ = drug concentration at which a 50% inhibition of neutral red dye uptake (as compared to untreated cultures) was observed.
$^b$$EC_{90}$ = drug concentration at which a 10-fold reduction of HBV virion DNA levels (as compared to untreated cultures) was observed.
$^c$$EC_{90}$ values are used for calculation of the Selectivity Index (S.I.) since reductions of HBV DNA levels that are less than three-fold are generally not statistically significant in this assay system.
$^d$Analysis of the effectiveness of the drug combination treatments by the CalcuSyn combination evaluation program (Biosoft, Inc.).

Example 34

Human Bone Marrow Progenitor Cells Toxicity Assay for L-dC

The myelosuppressive effects of certain nucleoside analogs have highlighted the need to test for potential effects on the growth of human bone marrow progenitor cells in clonogenic assays. In particular, anemia and neutropenia are the most common drug-related clinical toxicities associated with the anti-HIV drug zidovudine (ZDV). This toxicity has been modeled in an in vitro assay that employs bone marrow cells obtained from healthy volunteers (Sommadossi J-P, Carlisle R. "Toxicity of 3'-azido-3'-deoxythymidine and 9-(1,3-dihydroxy-2-propoxymethyl)guanine for normal human hematopoietic progenitor cells in vitro" Antimicrob Agents Chemother 1987, 31(3), 452–454). ZDV has been shown to directly inhibit human granylocyte-marcrophage colony-forming (CFU-GM) and erythroid burst-forming (BFU-E) activity at clinically relevant concentrations of 1–2 $\mu$M. Using human bone marrow clonogenic assays with ZDV as a positive control and lamivudine as a negative control, L-dC had an $IC_{50}$ in CFU-GM and BFU-E of >10 $\mu$M (see Table 26).

TABLE 26

Bone Marrow Toxicity of L-dC in Granulocyte Macrophage Progenitor and Erythrocyte Precursor Cells

| Compound | CFU.GM$^a$ $IC_{50}$ ($\mu$M) | BFU-E$^a$ $IC_{50}$ ($\mu$M) |
|---|---|---|
| L-dC | >10 | >10 |
| Lamivudine | >10 | >10 |
| ZDV | 1.8 | 0.7 |

$^a$Values represent the results of three independent experiments performed in triplicate.

Example 35

Mitochondrial Toxicity Assay for L-dC

Antiviral nucleoside analogs approved for HIV therapy such as ZDV, stavudine (d4T), didanosine (ddI), and zalcitabine (ddC) have also been associated with clinically limiting delayed toxicities such as peripheral neuropathy, myopathy, and pancreatitis (8–11). These clinical adverse events have been attributed to inhibition of mitochondrial function due to reduction in mitochondrial DNA (mtDNA) content and nucleoside analog incorporation into mtDNA. In addition, a particular nucleoside analog, fialuridine (FIAU), caused hepatic failure, pancreatitis, neuropathy, myopathy and lactic acidosis due to direct mitochondrial toxicity. Drug-associated increases in lactic acid production can be considered a marker of impaired mitochondrial function or oxidative phosphorylation.

To assess the potential of L-dC to produce mitochondrial toxicity, several in vitro studies were conducted using the human heparoma cell line HepG2. These studies included analysis of lactic acid production, mtDNA content and determination of changes in morphology (e.g., loss of cristae, matrix dissolution and swelling, and lipid droplet formation) of mitochondrial ultrastructure. The effects of L-dC on mitochondria are presented in Table 27.

No differences were observed in lactic acid levels produced in cells chronically treated with L-dC and in untreated cells. Lactic acid production in the ZDV and FIAU treated cells increased by 100% compared to vehicle control. Exposure of HepG2 cells for 14 days to L-dC at concentrations up to 10 $\mu$M had no effect on mitochondrial DNA content compared to an 87% reduction in the ddC-treated cells. Following 14 days of exposure to 10 $\mu$M L-dC, the ultrastructure of HepG2 cells, and in particular mitochondria, were examined by transmission electron microscopy. No discernible changes in cell architecture or mitochondrial morphology were detected. The size and organization of mitochondrial cristae were normal. ZDV-treated cells showed typical swollen mitochondria with loss of cristae.

Mitochondrial morphology also was abnormal in the ddC- and FIAU-treated cells.

TABLE 27

Effect of L-dC on Hepatocyte Proliferation, Mitochondrial Function, and Morphology in HepG2 Cells

| Compound | $CC_{50}{}^a$ ($\mu$M) | Conc. ($\mu$M) | % of Control L-Lactate | % of Control mtDNA | Lipid Droplet Formation | Mitochondrial Morphology |
|---|---|---|---|---|---|---|
| Control | — | — | 100 | 100 | negative | normal |
| L-dC | >2000 | 10 | 101 ± 2 | 107 ± 8 | negative | normal |
| FIAU | 4 | 10 | 203 | 86 | positive | abnormal |
| ZDV | 14 | 50 | 239 ± 34 | 119 | negative | abnormal |
| ddC | 20 | 1 | 95 ± 4.4 | 13 | negative | abnormal |

$^a$$CC_{50}$ after 14 days of treatment.

Example 36

Human DNA Polymerases α, β, and γ Toxicity Assay for L-dC

Nucleosides and nucleoside analogs are usually metabolized within cells to their TP derivatives. Cellular DNA polymerases are routinely responsible for normal nuclear and mitochondrial DNA synthesis and repair. Because the TP metabolites are potential substrates for DNA polyrnerases, studies were undertaken to determine if L-dC-TP inhibited human DNA polymerases.

The nucleoside analog 3'-amino-3'-deoxythymidine (AMT) TP inhibited human DNA polymerase α by 30% at a concentration of 10 $\mu$M. Human DNA polymerases β and γ were inhibited by ddC-TP by 50% (5 $\mu$M) and 35% (2.5 $\mu$M), respectively. L-dC-TP and L-dU-TP were not inhibitory to human DNA polymerases α, β, and γ up to concentrations of 100 $\mu$M (Table 28). These results suggest that the TP of L-dC and L-dU have a low affinity for these nuclear and mitochondrial human DNA polymerases, which is consistent with the favorable safety profile of L-dC observed in vitro and in vivo.

TABLE 28

Effect of L-dC-TP on Hepatitis Virus DNA Polymerase and Human DNA Polymerases α, β and γ

| Substrate$^a$ | Viral DNA pol$^b$ | Human DNA pol α$^c$ | Human DNA pol β$^c$ | Human DNA pol γ$^c$ |
|---|---|---|---|---|
| L-dC-TP | 1.82 ± 0.23 | >100 | >100 | >100 |
| L-dU-TP | 5.26 ± 2.4 | >100 | >100 | >100 |
| Lamivudine-TP$^d$ | 0.50 ± 0.1 | >5 | 1.2 | 0.01 |
| L-FMAU-TP$^d$ | 0.15 ± 0.05 | >50 | >50 | >50 |
| L-ddA-TP | 2.0 ± 0.3 | >100 | >100 | >100 |

$^a$Each set of data represents the arithmetic mean value and, where presented, the standard deviation of three independent experiments.
$^b$WHV DNA polymerase.
$^c$3'-Amino-3'-deoxythymidine TP inhibited pol α 30% at 10 $\mu$M; ddC-TP inhibited pol β 50% at 5 mM and pol γ 35% at 3.5 $\mu$M.
$^d$Human DNA polymerase data for lamivudine-TP and L-FMAU-TP from Chang, et al. (13), and Yao, et al. (14), respectively.

Example 37

Toxicity Assay in Rats for Dival-L-dC

The toxicity associated with a single oral dose of dival-L-dC in rats was determined. A total of 40 animals (Sprague-Dawley rats, six to eight weeks of age) were studied; ten animals each (five males and five females) were randomized to receive a single oral dose of dival-L-dC at one of three doses selected from the dose-range finding portion of the study (500, 1000, or 2000 mg/kg) or control article. Animals were observed for 15 days. Cage side observations for moribundity and mortality were documented twice daily. Clinical observations and body weight were documented once daily on Days 1, 8, 14, and 15. Also on Day 15, blood samples for hematology and serum chemistries were collected. After completion of Day 15 evaluations, all animals were euthanized and subjected to a comprehensive gross necropsy, which included macroscopic examination of the external body surface, all orifices, and the cranial, thoracic, and abdominal cavities and their contents. Body and selected organ weight and organ-to-body and organ-to-brain weight ratios also were documented.

No overt signs of toxicity were observed during the study, and no treatment-related effects on body weight, organ weight, or clinical pathology parameters were seen. No treatment-related abnormalities were noted in hematology or serum chemistry profiles. Furthermore, there were no treatment-related macroscopic lesions observed at necropsy. Based on the results of this study, the NOAEL for dival-L-dC following a single oral dose in the rat was 2000 mg/kg.

Example 38

Toxicity Assay in Monkeys for Dival-L-dC

The potential toxicity of five escalating doses of dival-L-dC in cynomologus monkeys was determined. Four animals (two males and two females) each received a total of five oral dival-L-dC doses, one at each dose level (20, 100, 500, 1000, and 2000 mg/kg), on Days 1, 4, 7, 10, and 14, respectively.

Cage side observations for moribundity and mortality were documented twice daily. Clinical observations were documented daily. Blood samples for hematology and serum chemistries were collected and body weight measured before treatment on Days 1, 4, 7, 10, and 14, and before necropsy on Day 17. After completion of Day 17 evaluations, all animals were euthanized and a complete necropsy performed, including macroscopic examination and comprehensive tissue collection.

No treatment-related clinical abnormalities were observed. Following the initial dose on Day 1, each animal demonstrated a loss in body weight of approximately 0.6 kg. From Day 4 through the remainder of the study all animals maintained body weight.

The following observations were noted in the individual hematology profiles. At Day 17, erythrocyte counts (RBC), hemoglobin (HGB), and hematocrit (HCT) were lower (by approximately 15% to 27%, cumulatively in all four animals when compared to values obtained on Day 1. Exclusive of Animal No. 1001 (Male), at each timepoint changes in these parameters were <10% from the previous recorded value. For Animal No. 1001, the Day 4 RBC, HGB and HCT value were decreased by approximately 18% from the Day 1 values; subsequently, changes for this animal were <±9% overall. The cause of this initial change in unknown and the toxicological significance uncertain. On Day 1, the white blood cell count (WBC) was notably elevated in Animal No. 1101 (female, 36.3×10³ cell/μl), but decreased by nearly 55% by Day 4. The absolute polymorphonuclear leukocytes (APLY) and the percent polymorphonuclear leukocytes (PLY) were also decreased (73% and 40%, respectively) by Day 4 from elevated levels on Day 1. Changes were variable for the remainder of the study. The toxicological relevance is uncertain.

The following observations were noted in the individual serum chemistry profiles. Day 17 blood urea nitrogen (BUN) values were decreased (by ~43%, cumulatively) in all four monkeys when compared to Day 1 values. These cumulative changes result from interim variations of −39% to +46%. These changes were consistent in all monkeys on study; however, the toxicological relevance is uncertain.

Based on the results of this study, the NOAEL for dival-L-dC following a single oral dose by gavage in the monkey was 2000 mg/kg.

Example 39

28 Day Toxicity Assay in Woodchucks for L-dC

The woodchuck model of chronic hepatitis B infection has been valuable for the preclinical toxicological evaluation of nucleoside analogs. This model identified the delayed severe hepatocellular toxicity induced by FIAU in humans not seen in preclinical evaluation in rodents or primates. The FIAU-induced toxicity observed in woodchucks, including significant weight loss, wasting, and hepatocellular damage seen on liver biopsy, was identified beginning six to eight weeks from commencement of treatment and was similar to that observed in the FIAU-treated HBV-infected patients.

The antiviral activity and safety of L-dC as well as post-treatment viral rebound in woodchuck hepatitis virus (WHV) infected woodchucks was determined. Male and female woodchucks were infected as neonates by subcutaneous inoculation of diluted serum of WHV carriers and were all chronic carriers of WHV. Animals (16 to 18 months of age) were randomized to comparable groups on the basis of body weight, g-glutamyl transferase (GGT) levels, sex, and serum WHV DNA concentration (>10¹¹ genome equivalents/mL serum) measured by quantitative dot blot analysis.

Three animals each received L-dC at doses of 0.01, 0.1, 1.0, or 10.0 mg/kg/day orally for 28 days. In addition, three animals received lamivudine at 10 mg/kg/day orally for 28 days. Four animals received vehicle control according to the same schedule. All animals were monitored for rebound of WHV for an additional 56 days post-treatment. Blood samples for WHV DNA levels were obtained on Days −7, 0, 1, 3, 7, 14, 21, and 28, and WHV DNA levels were also obtained post-treatment on Days 1, 3, 7, 14, 28, and 56. WHV DNA levels were detected by a polymerase chain reaction (PCR) technique. Body weights were obtained concurrently and drug dosage was adjusted accordingly. If clinical evidence of toxicity was observed, clinical bio-chemical and hematological tests were to be performed. Post-mortem examination, including histologic evaluation of tissues, was to be performed on one animal that died during the study.

No toxicity was observed during the four-week treatment period or eight-week post-treatment follow-up period. Furthermore, there was no weight loss in any L-dC treatment group compared to control animals (FIG. 18). All animals gained weight in a fashion similar to control animals during the 84-day protocol period. One animal (#98051) in the 0.1 mg/kg/d group died on the eighth day after treatment ended. Postmortem examination revealed a large hepatic carcinoma (8×5×2 cm) in the left lateral lobe of the liver and death was attributed to the hepatic malignancy. Hepatocellular neoplasms are seen in this model as early as nine months of age and have been a cause of death as early as 15 months of age. Death in this animal was attributed to hepatocellular carcinoma, which is an expected part of the natural history of WHV infection, and was not considered related to L-dC treatment since there was no indication that drug toxicity was a factor in the death of the animal.

Example 40

Twelve-Week Toxicity Assay in Woodchucks for L-dC

The antiviral activity and safety of L-dC in woodchucks was determined. In this study, four animals each received L-dC 1.0 mg/kg/day or vehicle control orally for 12 weeks. Four additional animals received L-dC along with another nucleoside analog, L-dT. The animals were randomized into comparable groups, stratified by sex, weight, and pretreatment serum WHV DNA and GGT levels.

WHV DNA and body weight were measured on Days 0, 1, 3, 7, 14, 21, 28, 42, 56, and 84 as well as on post-treatment Days 7, 14, 21, 28, 42, 56, 70, and 84. WHV DNA levels were determined by quantitative PCR. Appropriate samples for hematology, serum chemistries, WHV serology, and liver biopsy were collected pretreatment and on Day 84. Plasma drag levels were determined from samples collected 2.5 hours post-dose on Days 0, 14 and 84.

L-dC (1 mg/kg/day, orally) was well tolerated and showed no drug-related toxicity through 12 weeks of treatment or during 12 weeks of follow-up. WHV viremia in chronically infected woodchucks treated for 12 weeks with L-dC (1 mg/kg/d, orally) decreased by 0.5 to 1 log 10 by the end of 12 weeks of treatment, similar to the response in the 28 day study at this dose. This study included additional groups treated with L-dT 1 mg/kg/day, and L-dC (1 mg/kg/day) plus L-dT (1 mg/kg/day) administered in combination. This combination of L-dC and L-dT reduced viral load to the limit of detection, similar to that seen during treatment with L-dC or L-dT at 10 mg/kg/day in the 28 day study. There was no difference in weight between the animals in the groups treated with L-dC and the control group (see FIG. 19). One animal in the control group died at Week 8; necropsy revealed the cause of death to be aortic degeneration and rupture. Although unusual, spontaneous rupture of the ascending aorta has been observed historically in both uninfected and WHV-infected woodchucks. The weight of all animals decreased slightly during the 24-week study period. Previous experience has determined that this slight decrease in weight was due to the approach of a hibernation cycle (B. Tennant, DVM; Marmotech, Inc.). Serum chemistries and hematology from all animals were in the normal range before and after 12 weeks of treatment. Liver tissue histomorphology as evaluated by microscopy was normal for all groups. There was no evidence of fatty change (microvesicular steatosis).

Example 41

Repeated-Dose Toxicokinetics of Dival-L-dC in the Cynomologus Monkeys

The potential toxicity and pharmacokinetics of dival-L-dC after oral administration for 25 days to cynomologus monkeys was determined. Eight animals (four males and four females) were randomized to receive dival-L-dC via gavage at one of three doses (500, 1000, or 2000 mg/kg) or vehicle control once daily for 25 days (total N=32). Cage side observations for moribundity and mortality were documented twice daily, and clinical observations documented once daily. Body weights were documented before treatment on Days 1, 8, 15 and 25 and before necropsy on Day 26. Food consumption was documented daily and reported for weekly intervals as a daily average. Physical and ophthalmologic examinations and urinalysis were performed before treatment and at necropsy. After completion of Day 26 evaluations, all animals were euthanized and subjected to a comprehensive gross necropsy, which included macroscopic examination of the external body surface, all orifices, and the cranial, thoracic, and abdominal cavities and their contents. Body and selected organ weight and organ-to-body and organ-to-brain weight ratios also were documented. Tissue obtained by comprehensive gross necropsy was evaluated histomorphologically by a board-certified veterinary pathologist.

A. Body Weights

All animals either maintained or gained body weight during the course of the study, except for Animal Nos. 2002 (500 mg/kg group), and 4001 and 4003 (2000 mg/kg group), which demonstrated a weight loss of 0.1 kg on Day 25 (compared to Day 1). The statistically significant differences between the males in the control group and the males in the dival-L-dC treated groups are not considered toxicologically relevant as the pre-study mean body weight for control group animals was greater than the mean body weights for the treatment groups by 0.13–0.25 kg.

B. Food Consumption

During the course of the study, all animals maintained adequate food consumption with expected variability. The mean biscuit consumption was less than control males for the 500 mg/kg group males on Days 8/9, 15/16, and 16/17; 1000 mg/kg group males on Days 24/25; and 2000 mg/kg group makes on Days 8/9, 15/16, 16/17, 20/21 and 23/24. The only difference noted in the females was a decrease in food consumption in the 2000 mg/kg group females on Day 7/8. These differences are not considered toxicologically relevant.

C. Clinical Pathology

Hematology. On Day 1 prior to the initiation of treatment, there were no differences between the control and treatment groups for any hematological parameter. On Day 26, a number of statistically significant differences were noted in the erythrocyte indices, including a decreased red blood cell count (RBC_ (all treated females), decreased hemoglobin (HGB) (all treated males), and decreased hematocrit (HCT) (all treatment groups, both sexes). The males also demonstrated a reduced RBC, but the differences were not statistically significant. Hemoglobin concentration was also lower in the treated females, but was not statistically significant. Relative to Day 1, the RBC, HGB and HCT were decreased on Day 26 in the control and dival-LdC treated males and females. However, the relative decreases observed for the control animals were less than those noted for the dival-L-dC treated animals. These results are indicative of a clinically relevant non-hemolytic anemia; however, any dose response phenomenon was minimal, and histopathologic evaluation suggests that the bone marrow remained responsive. Therefore, any progressive or permanent effects are considered unlikely.

In the white blood cell count, there were decreased absolute polymorphonuclear leukocytes (APLY) (500 MG/KG and 1000 mg/kg group females and 2000 mg/kg group males and females), decreased percent polymorphonuclear leukocytes (PLY) (1000 mg/kg and 2000 mg/kg group females), and increased percent lymphocytes (LYM) (2000 mg/kg group males and 1000 mg/kg and 2000 mg/kg group females).

Serum Chemistry. The mean alkaline phosphatase (ALK) levels for all treated males were significantly less the make control group mean ALK on Day 26. The mean globulin (GLOB) and calcium (CAL) levels were also elevated in the 2000 mg/kg group males on Day 26. These changes were not considered to be clinically relevant. The mean potassium (K) values were greater in the 1000 mg/kg and 2000 mg/kg group males than the control group and could be related to the observed non-hemolytic anemia present in those treatment groups. There were no changes in any serum chemistry parameter in the females on Day 26.

Urinalysis. The mean urinary pH was slightly decreased in the 2000 mg/kg group males and the 1000 mg/kg and 2000 mg/kg group females, but the differences were not statistically significant. Noteworthy and consistent with acidification of the urine was a lack of crystals in the urine from the high dose males and females.

D. Organ Weights

Statistically significant decreases in organ weights were noted for the lungs (absolute) of the 1000 mg/kg and 2000 mg/kg group males and the relative thymus (thymus:brain) of the 2000 mg/kg group males. However, these differences were not considered toxicologically relevant.

E. Pathology

Macroscopic. There were no macroscopic findings that were interpreted as related to the administration of the dival-L-dC. All macroscopic findings were typical of those commonly present as incidental findings in non-human primates.

Microscopic. Thymic atrophy was the only microscopic finding that was interpreted as a treatment-related finding. The incidence and severity of thymic atrophy was increased in the 1000 mg/kg and 2000 mg/kg group males and females, but was not affected in the 500 mg/kg group animals. However, the clinical significance of the thymic atrophy was interpreted as equivocal. The dose-response relationship was weak, not all 1000 mg/kg and 2000 mg/kg group males were affected and thymic atrophy typically occurs as primates age. Other microscopic findings present in this study were commonly minor inflammatory or degenerative changes of the usual type and incidence observed in primates of this age.

Toxicokinetics. Blood samples for hematology and serum chemistries were collected pretreatment Day 1 and before necropsy on Day 26. Blood samples were collected for pharmacokinetic analysis on Day 25 from each animal at each of the following times after dosing: 0.5, 1, 2, 4, 6, 8, 12, and 24 hours. Plasma was prepared from blood and analyzed for concentrations of dival-L-dC and three metabolites: L-dC, L-dU and the partially de-esterified form of dival-L-dC, β-L-2'-deoxycytidine-5'-valine ester. Only L-dC and β-L-2'-deoxycytidine-5'-valine ester wee quantifiable. The mean plasma concentration-time data for the 1000 and 2000 mg/kg group were subjected to noncompartmental pharmacokinetic analysis using WinNonlin 1.5 (Model 200). Analysis of the 500 mg/kg mg/kg group is in progress.

Plasma concentrations of β-L-2'-deoxycytidine-5'-valine ester on Day 25 reached maximal values ($C_{max}$) at 1 hour (median $T_{max}$) post oral administration of dival-L-dC, compared to a median $T_{max}$ of 2–4 hours for L-dC. However, β-L-2'-deoxycytidine-5'-valine ester $C_{max}$ values were approximately 2 orders of magnitude lower than for L-dC. After reaching $C_{max}$, concentrations of L-dC declined in an apparent bi-exponential manner for each group. Estimated $AUC_{last}$ between males and females showed an absence of sex related differences and $AUC_{last}$ appeared to increase in a directly proportional manner to increases in dosages.

The data suggest that following oral administration of dival-L-dC is a rapid conversion to the de-esterified form of dival-L-dC, β-L-2'-deoxycytidine-5'-valine ester, and then L-dC but overall exposure is 100 fold higher for L-dC than for β-L-2'-deoxycytidine-5'-valine ester. Overall exposure to metabolite β-L-2'-deoxycytidine-5'-valine ester appears to increase in an approximately linear manner with increases in dosages.

A summary of toxicokinetic results is presented in Table 29.

TABLE 29

Pharmacokinetic Analysis of Repeated-Dose Dival-L-dC 1000 mg/kg and 2000 mg/kg Administered Orally in the Monkey

| Dosage (mg/kg/day) | Sex | (n) | $C_{max}$ (mg/mL) | $T_{max}$ (h) | $T_{last}$ (h) | $AUC_{last}$ (mg-hr./mL) | AUC (mg-hr./mL) | $t_{½}$ (h) |
|---|---|---|---|---|---|---|---|---|
| L-dC | | | | | | | | |
| 1000 | M | (4) | 66.7 (±29.1) | 2 | 12 | 273 (±107) | 295 (±110) | 4.1 (±1.8) |
| 1000 | F | (4) | 106 (±39) | 2 | 12 | 429 (±19) | 468 (NA) | 3.7 (NA) |
| 2000 | M | (4) | 116 (±13) | 4 | 12 | 668 (±127) | 726 (±114) | 3.8 (±1.3) |
| 2000 | F | (4) | 103 (±12) | 2 | 24 | 567 (±208) | 598 (±220) | 5.1 (±1.7) |
| β-L-2'-deoxycytidine-5'-valine ester | | | | | | | | |
| 1000 | M | (4) | 0.624 (±0.273) | 1 | 5 | 1.46 (±0.45) | ID | ID |
| 1000 | F | (4) | 1.23 (±0.25) | 1 | 4 | 1.90 (±0.41) | ID | ID |
| 2000 | M | (4) | 1.64 (±0.42) | 1 | 10 | 3.66 (±0.88) | ID | ID |
| 2000 | F | (4) | 1.29 (±0.28) | 1 | 8 | 3.67 (±0.42) | ID | ID |

[1]Mean values (+ SD) at Day 25.
[2]n = 4 for all parameters for both L-dC and β-L-2'-deoxycytidine-5'-valine ester except for 2000 mg/kg group females, for which n = 3 and for L-dC AUC and $t_{½}$, 1000 mg/kg group females, where n = 2 due to inadequate characterization of the terminal phase.
[3]Median (rather than mean) values are presented for $T_{max}$, and $T_{last}$.
NA Not Applicable.
ID Insufficient Data to define terminal phase for all animals.

terminal phase mean half-lives were approximately 4–5 hours for males and females in both dosage groups. These half-life estimates should be viewed as minimal values, however, because most individual estimates were based on data from 6 to 12 hours post-dose, at which time the terminal phases may not have been completely characterized. Mean β-L-2'-deoxycytidine-5'-valine ester concentrations also declined after reaching $C_{max}$, but the terminal phases were not adequately defined to allow estimation of half-lives. Mean $C_{max}$ values for L-dC and β-L-2'-deoxycytidine-5'-valine ester were similar for males and females within each dosage group, except for 1000 mg/kg group makes, which were lower by half the concentration values of the 2000 mg/kg group males. Therefore, $C_{max}$ appeared to increase with dosage only for the 1000 mg/kg group males.

Comparison of L-dD $AUC_{last}$ between males and females showed trends similar to those noted for $C_{max}$ with the males sin the 1000 mg/kg group having values lower by approximately half the $AUC_{last}$ values of the 2000 mg/kg group males. Comparison of β-L-2'-deoxycytidine-5'-valine ester Example 42

Repeated-Dose Toxicokinetics of Dival-L-dC in the Rat

The potential toxicity and pharmacokinetics of dival-L-dC after oral administration for 28 days to rats was determined. Twenty animals each (10 males and 10 females) were randomized to receive dival-L-dC via gavage at one of three doses (500, 1000, or 2000 mg/kg) or vehicle control once daily for 28 days. Cage side observations for moribundity and mortality were documented twice daily. Clinical observations were documented once daily. Body weights were documented before dosing on Days 1, 8, 15, 22, and 28 and before necropsy on Day 29. Food consumption was documented weekly. Blood samples for hematology and serum chemistries also were collected before necropsy on Day 29. After completion of Day 29 evaluations, all animals were euthanized and subjected to a comprehensive gross necropsy, which included macroscopic examination of the external body surface, all orifices, and the cranial, thoracic, and abdominal cavities and their contents. Body and selected organ weight and organ-to-body and organ-to-brain weight ratios also were documented. Tissue obtained by comprehensive gross necropsy was evaluated histomorphologically by a board-certified veterinary pathologist.

A. Body Weights

The mean body weight values for the 2000 mg/kg group males on Days 22 and 28 were significantly lower than the mean value for the male control group. The mean body weight value for the 2000 mg/kg group females on Day 28 was also significantly lower than the mean value for the control group females.

B. Food Consumption

Food consumption was reduced in the 2000 mg/kg group males throughout the duration of the study. Also, the food consumption of the 1000 mg/kg group males during the third week of the study was significantly less than the control group males. The food consumption was significantly reduced in the 1000 mg/kg and 2000 mg/kg females during the second, third, and fourth weeks of the study.

C. Clinical Pathology

Hematology. On Day 29, a number of statistically significant differences were noted in the erythrocyte indices. The red blood cell count (RBC) was significantly reduced in both males and females at all three dose levels (500, 1000 and 2000 mg/kg). The hemoglobin concentration (HGB) was decreased in the 2000 mg/kg group males, the 1000 mg/kg group females and the 2000 mg/kg group females. A decrease in hematocrit (HCT) was noted in the 1000 mg/kg and 2000 mg/kg group males and females. The mean cell volume (MCV) was significantly increased in the 500, 1000 and 2000 mg/kg group males and in the 500 and 1000 mg/kg group females. The mean cell hemoglobin (MCH) was significantly increased in the 500, 1000 and 2000 mg/kg group males and females. The mean cell hemoglobin concentration (MCHC) was increased in the 1000 mg/kg females. The nucleated red blood cell count (NRC; absolute and relative) was decreased in the 1000 mg/kg and 2000 mg/kg males and increased in the 2000 mg/kg females. These changes indicate a treatment-related mild responsive anemia.

The white blood cell count (WBC) was decreased in the 2000 mg/kg males. There was a reduction in the monocytes (MNO; absolute and percentage) in the 2000 mg/kg group males. Platelets (PLT) were increased in the 2000 mg/kg males. However, these changes were quantitatively small and the toxicological relevance is uncertain.

Serum Chemistry. Mean globulin (GLOB) levels were decreased in the 2000 mg/kg group males and the 1000 mg/kg group females on Day 29. The albumin/globulin ratios were increased in the 1000 and 2000 mg/kg group males and the 1000 mg/kg group females. The alkaline phosphatase (ALK) levels were elevated in the 500 mg/kg group females. The cholesterol (CHOL) levels were increased in the 1000 mg/kg females. These minor changes did not form dose-response-related patterns or trends to suggest that these values were toxicologically relevant.

D. Organ Weights

Significant decreases in absolute organ weights were noted for the lungs (2000 mg/kg group males and females) and thymus (2000 mg/kg group males, 1000 mg/kg group females and 2000 mg/kg group females). Also significant was the decrease in the mean absolute organ weight for the prostate and seminal vesicles in the 2000 mg/kg group males. The mean absolute heart weights were decreased in the 1000 mg/kg and 2000 mg/kg group females. The salivary glands mean weight was decreased in 2000 mg/kg group females. The mean spleen weight was increased in the 2000 mg/kg group females.

The relative (to body) organ weight changes included an increased brain weight in the 2000 mg/kg group males and females. An increase in the mean testis weight of the 1000 mg/kg and 2000 mg/kg group males was also noted. The relative thymus weight was reduced in the 2000 mg/kg group males and the 1000 mg/kg and 2000 mg/kg group females. The mean relative spleen weight was increased in the 2000 mg/kg group females.

Also, the relative (to brain weight) organ weight changes included a decreased relative lung weight in the 2000 mg/kg group males. The relative thymus weights were decreased in the 1000 mg/kg and 2000 mg/kg group males and females. The relative prostate and seminal vesicle mean weights were also decreased in the 2000 mg/kg group males. The mean relative heart weight was reduced in the 2000 mg/kg group females as was the mean relative weight of the salivary glands. The relative spleen weight was increased in 2000 mg/kg group females.

The decreases in organ weights (thymus, lung, heart, salivary glands, prostate, seminal vesicles, and brain) were interpreted as secondary to the generalized body weight loss presented in the 1000 mg/kg and 2000 mg/kg group animals. Thymic atrophy, which was observed microscopically in the 1000 mg/kg and 2000 mg/kg group animals, was consistent with the decreased thymus weights observed. Other tissues with decreased weights did not have microscopic correlates. The increased spleen weights were interpreted as a consequence of erythropoietic activity observed microscopically.

E. Pathology

Microscopic. The incidences of thymic atrophy and lymphoid necrosis were increased in the 1000 mg/kg and 2000 mg/kg group animals, but were not affected in the 500 mg/kg group animals. However, the clinical significance of thymic atrophy and lymphoid necrosis was interpreted as equivocal because the dose-response relationship was weak. Also, these thymic changes are often present as non-specific changes in animals stressed by a variety of factors, and significant body weight reductions were observed in the 1000 mg/kg and 2000 mg/kg group animals in this study.

Erythropoiesis in spleen was increased in the 1000 mg/kg and 2000 mg/kg group males and females sufficiently to distinguish them from the controls, but the spleens from the 500 mg/kg group animals were similar to controls. Hematopoiesis in liver was increased in the 2000 mg/kg group males and females sufficiently to distinguish them from the controls, but the livers from 500 mg/kg and 1000 mg/kg group animals were similar to those in controls. Hyperplasia in sternal bone marrow was observed in the 2000 mg/kg group males and females. Erythropoiesis in spleen, increased hematopoiesis in liver and hyperplasia in bone marrow were all interpreted as expected and appropriate responses to the mild anemia observed as a part of the hematology results. These results confirm the responsive nature of the anemia during continued treatment.

There were several other microscopic changes present in this study. These were most commonly minor inflammatory or degenerative changes of the usual type and incidence observed in rodent gavage studies.

Toxicokinetics. An additional 54 animals (27 males and 27 females) had samples collected for pharmacokinetic analyses on Days 1 and 28. On both days, samples were collected at each of six timepoints (alternating two animals per timepoint): 0.5, 1, 2, 4, 8 and 24 hours post-dosing. Plasma was prepared from blood and analyzed for concentrations of dival-L-dC and three metabolites: L-dC, L-dU and the partially de-esterified form of dival-L-dC, β-L-2'-deoxycytidine-5'-valine ester. Only L-dC and β-L-2'-deoxycytidine-5'-valine ester were qualifiable. The mean plasma concentration-time data for the 1000 and 2000 mg/kg group were subjected to noncompartmental pharmacokinetic analysis using WinNonlin 1.5 (Model 200). Analysis of the 500 mg/kg group is in progress.

Mean plasma concentrations of the metabolite, L-dC, reached maximal values ($C_{max}$) at 2 hours post-dose ($T_{max}$) for the 1000 mg/kg dose group and at 1–4 hours post-dose for the 2000 mg/kg dose group. Mean $C_{max}$ values for males and females were comparable within each of the 1000 mg/kg and 2000 mg/kg dosage groups and were similar on Day 28 versus Day 1 in both groups. $C_{max}$ increased with dose in most cases but the extent of the increase was variable. After reaching $C_{max}$, concentrations of L-dC declined in an apparent bi-exponential manner for each group. Estimated terminal phase half-lives for the 1000 mg/kg dose group (9–17 hours) tended to be longer for the 2000 mg/kg dose group (6–8 hours), but the half-life estimates should be interpreted with caution. The estimation of he half-lives required using only three data points and the data tended to be variable. Also, one of three data points used was at 4 hours, at which time the terminal phase may not have been established. $T_{last}$ for L-dC concentrations occurred at 24 hours for all data sets. $AUC_{last}$ was comparable for males and females within each group, and did not appear to be substantially different on Day 28 versus Day 1. Although $C_{max}$ for L-dC did not appear to increase with increased dosage of dival-L-dC in a consistent manner, as noted above, $AUC_{last}$ of L-dC increased with dival-L-dC in a relationship that appeared to be approximately proportional to dose.

Plasma mean concentrations of β-L-2'-deoxycytidine-5'-valine ester reached maximal values ($C_{max}$) at 1 to 2 hours post-dose ($T_{max}$). Mean $C_{max}$ values for males and females were similar within each dosage group with a trend toward higher values for females. $C_{max}$ values were approximately 14% to 50% higher for females on each Day 1 and Day 28 except for females in the 2000 mg/kg group, where β-L-2'-deoxycytidine-5'-valine ester $C_{max}$ values were approximately 164% higher than males on Day 28. When comparing values within each gender, $C_{max}$ values on Day 28 wee similar to Day 1 except for females in the 2000 mg/kg group for which $C_{max}$ values were 130% higher on Day 28 Day 1. $C_{max}$ increased with dosage in each case, but by a factor that was generally less than linearly proportional to dose.

The apparent terminal elimination phase of β-L-2'-deoxycytidine-5'-valine ester was not well characterized and therefore half-lives were not reported. $T_{last}$ for β-L-2'-deoxycytidine-5'-valine ester concentrations occurred at 4–8 hours for the 1000 mg/kg dose group and at 8–24 hours for the 2000 mg/kg dose group. As was noted for $C_{max}$, the $AUC_{last}$ was 25% to 50% higher for females than males. $AUC_{last}$ was consistently slightly higher on Day 28 vs. Day 1 for both males and females (30% to 62%). $AUC_{last}$ increased with dosage in a relationship that appeared to be approximately linearly proportional to dose.

These data suggest that both L-dC and β-L-2'-deoxycytidine-5'-valine ester reached systematic circulation relatively rapidly. Overall exposure as measured by $C_{max}$ was 10 to 40 fold greater for L-dC than β-L-2'-deoxycytidine-5'-valine ester and 35 to 80 fold greater as measured by $AUC_{last}$. Exposure appeared to increase proportionally to dosage within the dosage range of 1000–2000 mg/kg/day. Overall exposure on Day 29 of L-dC was comparable to that observed on Day 1 while β-L-2'-deoxycytidine-5'-valine ester exposure was generally greater on Day 28, suggesting that accumulation of β-L-2'-deoxycytidine-5'-valine ester may occur during repeated dosing.

A summary of toxicokinetic results is presented in Table 30.

TABLE 30

Pharmacokinetic Analysis of Single- and Repeated-Dose Dival-L-dC 1000 mg/kg and 2000 mg/kg Administered Orally in the Rat

| Dosage (mg/kg day) | Day | Sex | $C_{max}$ (μg/mL) | $T_{max}$ (h) | $T_{last}$ (h) | $AUC_{last}$ (μg·hr/mL) | AUC (μg·hr/mL) | t½ (h) |
|---|---|---|---|---|---|---|---|---|
| \multicolumn{9}{c}{L-dC} | | | | | | | | |
| 1000 | 1 | M | 33.6 | 2 | 24 | 255 | 363 | 17.3 |
| 1000 | 1 | F | 48.5 | 2 | 24 | 239 | 279 | 9.4 |
| 1000 | 28 | M | 52.9 | 2 | 24 | 254 | 334 | 12.9 |
| 1000 | 28 | F | 46.6 | 2 | 24 | 239 | 277 | 8.8 |
| 2000 | 1 | M | 70.9 | 2 | 24 | 700 | 478 | 5.8 |
| 2000 | 28 | F | 59.4 | 2 | 24 | 461 | 487 | 5.6 |
| 2000 | 28 | M | 51.1 | 4 | 24 | 500 | 550 | NA |
| 2000 | 28 | F | 77.7 | 1 | 24 | 578 | 561 | 8.5 |
| \multicolumn{9}{c}{β-L-2'-deoxycytidine-5'-valine ester} | | | | | | | | |
| 1000 | 1 | M | 1.31 | 1 | 4 | 2.81 | ID | ID |
| 1000 | 1 | F | 1.70 | 2 | 4 | 4.07 | ID | ID |
| 1000 | 28 | M | 1.32 | 2 | 8 | 3.96 | ID | ID |
| 1000 | 28 | F | 1.97 | 2 | 4 | 5.36 | ID | ID |
| 2000 | 1 | M | 2.38 | 2 | 8 | 8.09 | ID | ID |
| 2000 | 1 | F | 2.71 | 2 | 8 | 10.2 | ID | ID |
| 2000 | 28 | M | 2.36 | 1 | 8 | 11.0 | ID | ID |
| 2000 | 28 | F | 6.24 | 2 | 24 | 16.5 | ID | ID |

NA = Not Applicable; a terminal phase was not adequately characterized.
ID = Insufficient Data to define terminal phase for all animals.

Example 43

S. typhimurium and E. coli Plate Incorporation Mutation Assay (Genotoxicity)

Dival-L-dC when administered orally to animals is rapidly converted to L-dC to give high plasma concentrations of L-dC and no detectable dival-L-dC. Therefore, the mutagenicity studies conducted in vitro were performed using L-dC. This study was conducted in accordance with FDA GLP regulations. L-dC was tested for its potential to cause mutation at the histidine operon of *Salmonella typhimurium* strains TA98, TA100, TA1535, and TA1537 and at the tryptophan opeton of *Escherichia coli* strain WP2uvrA. L-dC at concentrations of 50, 100, 500, 1000, and 5000 mg/plate plus positive and negative controls were tested. Test strains were exposed to L-dC or control in the absence of exogenous activation and in the presence of induced rat liver S-9 extract plus eofactors. After incubation for approximately 68 hours, L-dC and controls were evaluated for the number of revertants per plate and integrity of the background microcolony lawn.

Both negative and positive controls fulfilled the requirements of the test. The results of both definitive and confirmatory assays indicated that L-dC did not induce any significant increase in the number of revertant colonies for any of the test strains in the presence or absence of induced rat liver S-9 extract. Based on the study findings, it was concluded that there was no evidence of mutagenicity in the *S. typhimurium* or *E. coli* plate incorporation mutation assay with L-dC concentrations up to 5000 mg/plate.

Example 44

Chromosomal Aberration Assay

Dival-L-dC when administered orally to animals is rapidly converted to L-dC to give high plasma concentrations of L-dC and no detectable dival-L-dC. Therefore, the mutagenicity studies conducted in vitro were performed using L-dC. This study was conducted in accordance with FDA GLP regulations. L-dC was tested for its potential to induce chromosomal aberrations in cultured CHO cells. In the definitive assay, L-dC at concentrations of 100, 500, 1000, and 5000 mg/mL and positive and negative controls were tested with and without metabolic activation. After continuous treatment for 18 hours, toxicity was determined by the reduction in relative cell growth (RCG) and relative mitotic index (RMI). Based on the RCG and RMI results, chromosomal aberrations were scored from the three highest concentrations (500, 1000, and 5000 mg/mL). One hundred metaphases were scored from each of the duplicate cultures at each concentration (including positive and negative controls).

A confirmatory assay was performed without activation only with L-dC concentrations of 1.0, 10, 100, 500, 1000, and 5000 mg/mL. After continuous treatment for 18 hours, the reduction in RCG and RMI were determined. Based on RCG and RMI results, chromosomal aberrations were scored from the three highest concentrations (500, 1000, and 5000 mg/mL). One hundred metaphases were scored from each of the duplicate cultures at each concentration level (including positive and negative controls).

Results from the definitive and confirmatory assays indicated that L-dC did not induce a statistically significant increase (defined as a p-value £0.05 determined by the Chi-square test) in the percentage of cells with aberrations at any of the concentrations tested, both with and without metabolic activation, compared to solvent controls. Based on the study findings, it was concluded that there was no evidence of chromosomal aberrations in the CHO assay after exposure to L-dC at concentrations up to 5000 mg/mL, and L-dC is not considered to be a clastogenic agent.

Example 45

Mouse Micronucleus Assay

Dival-L-dC when administered orally to animals is rapidly converted to L-dC to give high plasma concentrations of L-dC and no detectable dival-L-dC. Therefore, the mutagenicity studies conducted in vitro were performed using L-dC. This study was conducted in accordance with FDA GLP regulations. Assuming an oral bioavailability of 10–20% in the rodent (see Pharmacology and Toxicology, Section 8.1.7.3) exposure to L-dC (2000 mg/kg dose) would reach or exceed 400 mg/kg. This level of exposure would exceed the expected human exposure by 20 to 50-fold.

L-dC was tested for its potential to induce micronucleated polychromatic erythrocytes (MPCE) in the bone marrow cells of male and female mice. L-dC at concentrations of 500, 1000, and 2000 mg/kg and positive and negative controls were tested. Study drag was administered by oral garage as a single dose. Two harvests approximately 24 and 48 hours after L-dC or negative control administration were performed, and a single harvest approximately 24 hours after positive control administration was performed. Five male and five female mice per dose group per harvest time were used. The percentage of polychromatic erythrocytes (PCE) and MPCE frequency were determined for each timepoint.

The results of the study indicate that there was no statistically significant increase (defined as a p-value £0.025 determined by a one-tailed Student's t-test) in the number of MPCE at any timepoint in any L-dC dose group compared to negative control. A reduction of more than 20% versus the vehicle control in the percentage of PCE, as an indication of toxicity, was observed at each test article dose level at the 24 hour harvest time in both sexes (−30.5% to −43.1% for the males and −26.1% to −32.2% for the females). The reduction also indicates an appropriate exposure of test article to the target tissue. However, this reduction of more than 20% was not observed at any test article dose level at the 48 hour harvest time in either sex.

This study indicates that, under the conditions of the test and according to the criteria set for evaluating the test results, L-dC was negative in the micronucleus assay to male or female animals at doses up to 2000 mg/kg.

Example 46

Integrated Summary of Toxicologic Findings

Conventional cell-based assays were used to assess the cytotoxicity of L-dC and any cellular metabolites. L-dC was non-cytotoxic (50% cytotoxic concentration, $CC_{50}$, >2000 $\mu$M) to the human hepatoma cell line 2.2.15, which is routinely used to determine the anti-I-IBV activity of potential antiviral agents. L-dC was not cytotoxic to human peripheral blood mononuclear cells (PBMCs; $CC_{50}$>100 $\mu$M) and to human bone marrow progenitor cells (50% inhibitory concentration, $IC_{50}$, >10 $\mu$M in granulocyte-macrophage colony forming unit (CFU-GM) and erythroid burst-forming unit (BFU-E) assays).

TABLE 31

In Vitro Cytotoxicity of L-dC

| Cell line[a] | $CC_{50}$[b] (mM) |
|---|---|
| 2.2.15[c] | >2000 |
| PBMC[d] | >200 |
| HFF[c,e] | >100 |
| Daudi[c,e] | >50 |
| MDCK[b] | >100 |
| CV-1[c] | >100 |
| MA-104[c] | >100 |

[a]PBMC, peripheral blood mononuclear cells; HFF, human foreskin fibroblast; Daudi, Burkitt's B-cell lymphoma; MDCK, canine kidney epithelial cells; CV-1, African green monkey kidney fibroblast cells; MA-104, rhesus monkey kidney epithelial cells.
[b]$CC_{50}$ = 50% cytotoxic concentration; '>' indicates that no $CC_{50}$ was reached at the highest drug concentration tested.
[c]NIH, Antiviral Research and Antimicrobial Chemistry Program.
[d]R. Schinazi, Emory University, Veterans Affairs Medical Center.
[e]Result presented in µg/mL rather than µM.

In addition, L-dC was not cytotoxic to numerous other cell lines of human and other mammalian origin. No discernible changes in the function, morphology, or DNA content of mitochondria were noted and there was no lactic acid accumulation in L-dC treated hepatocytes ($IC_{50}$>10 µM). The triphosphate form of L-dC was not inhibitory to the human DNA polymerases α, β and γ, up to concentrations of 100 µM.

In acute single dose (including 500, 1000, and 2000 mg/kg single oral dose) toxicology studies in rats and in monkeys (dose escalation over days 1, 4, 7, 10 and 14 up to 2000 mg/kg) there were no overt signs of toxicity nor were there any dival-L-dC related effects on body weight, food consumption, or clinical pathology parameters (hematology and serum chemistry). In addition, there were no macroscopic lesions observed at necropsy, nor were there any microscopic findings on histomorphological analysis attributable to dival-L-dC. Based on the results of these studies, the no observed adverse effect level (NOAEL) for dival-L-dC, following a single dose by oral gavage in the Sprague-Dawley rat and cynomologus monkey was 2000 mg/kg.

In the subchronic (25 day) toxicology study in monkeys, the NOAEL was less than 500 mg/kg for dival-L-dC. Thymic atrophy was the only microscopic finding that was possibly related to dival-L-dC, but the clinical significance was interpreted as equivocal. A mild non-hemolytic anemia (decreased red blood cell count, decreased hemoglobin, and hematocrit) and decrease in the absolute and percent polymorphonuclear leukocyte counts of no apparent consequence were noted at the 500 mg/kg dose level. Other than the hematological changes there were no other toxicities identified in any dose group.

In the subchronic (28 day) toxicology study in rats, the NOAEL was less than 500 mg/kg for dival-L-dC. Oral administration of the dival-L-dC for 28 days to the rat at a dose of 2000 mg/kg resulted in treatment related changes that included a mild macrocytic anemia, reduced thymus weight, increased spleen weight (females only), reduced body weight, and hematopoiesis in the spleen, liver and sternal bone marrow. Oral administration of dival-L-dC for 28 days to the rat at a dose of 1000 rog/kg resulted in treatment related changes that included a mild macrocytic anemia, thymic atrophy (females only) and hematopoiesis in the spleen. The histomorphological changes seen in the liver, spleen and bone marrow reflect a hematological response to the mild anemia. Oral administration of the dival-L-dC for 28 days to the rat at a dose of 500 mg/kg resulted in a mild macrocytic anemia. Other than the hematological changes and hematopoietic responses noted there were no other toxicities identified in any dose group.

In normal healthy woodchucks or woodchucks chronically infected with hepatitis B virus (efficacy model for treatment of HBV infection), no toxicity was observed during acute (10 mg/kg single dose IV and PO) and subchronic (28 days at 10 mg/kg/day orally and 12 weeks at 1 mg/kg/day orally) studies of animals receiving L-dC. There was no weight loss in the L-dC treatment groups compared to control animals, clinical pathology parameters (hematology and serum chemistry) were in the normal range and liver biopsies taken at end of treatment in the 12-week study showed no evidence of fatty change (microvesicular steatosis).

L-dC was not mutagenic in the *S. typhimurium* or *E. coli* plate incorporation mutagenicity assay at concentrations up to 5000 µg/plate. There was no evidence of chromosomal aberrations in the Chinese hamster ovary (CHO) assay after exposure to L-dC at concentrations up to 5000 µg/mL (or 22.0 mM). In the mouse micronucleus assay, L-dC was not clastogenic to male or female animals at doses up to 2000 mg/kg.

Mild anemia noted in the monkey was not associated with any clinical correlates even at the highest dose (2000 mg/kg) and in the rat at 500 mg/kg. In addition the reticulocyte counts were unchanged. Although there was no formal reversibility component in these studies it is apparent that a hematological rebound can occur as indicated by the extramedullary hematopoiesis seen in the spleen and liver at the higher doses in the rat.

TABLE 32

Interspecies Comparison of Doses by Weight and Body Surface Area

| Species | Body Weight (kg) | Dose (mg/kg) | Dose (mg/animal) | Conversion Factor | Human Equivalent Dose (HED) (mg/kg) | Fold-Difference |
|---|---|---|---|---|---|---|
| Rat | 0.2 | 500 | 100 | 6 | 16.6 | 23 |
| Monkey | 4.0 | 500 | 2000 | 3 | 666 | 938 |
| Woodchuck | 3.0 | 10 | 30 | 3 | 10 | 14 |
| Human | 70 | 0.71 | 50 (proposed) | 1 | 0.71 | — |

Similar hematological changes at comparable or lower doses were observed in preclinical toxicity studies of lamivudine (Epivir-HBVT™), and valacyclovir (Valtrex™). Both of these approved drugs are members of the same well-characterized class (nucleoside or nucleoside analog) as dival-L-dC. The choice of lamivudine for comparison is based on the fact that it is a cytosine derivative as is dival-L-dC and on its approval for the treatment of chronic hepatitis B infection. The choice of valacyclovir for comparison is based on the fact that it is a valine ester prodrug of the nucleoside acyclovir.

This invention has been described with reference to its preferred embodiments. Variations and modifications of the invention, will be obvious to those skilled in the art from the foregoing detailed description of the invention. It is intended that all of these variations and modifications be included within the scope of this invention.

What is claimed is:

1. A compound of the formula

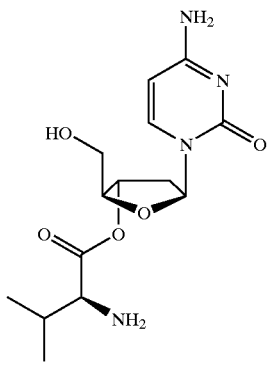

or a pharmaceutically acceptable salt thereof.

2. A pharmaceutical composition comprising a compound of the formula

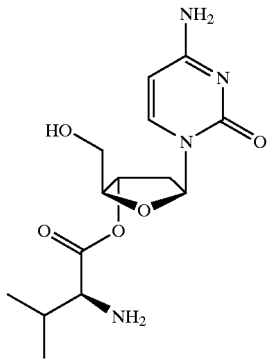

or a pharmaceutically acceptable salt thereof, in combination with β-L-deoxyribothymidine.

3. A compound of the formula:

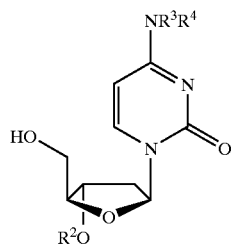

or a pharmaceutically acceptable salt thereof, wherein
$R^2$ is an amino acid residue; and
$R^3$ and $R^4$ are independently H, straight chained, branched or cyclic alkyl, dialkylaminoalkylene, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug.

4. The compound of claim 3, wherein $R^2$ is an amino acid residue of the formula $C(O)C(R^8)(R^9)(NR^{10}R^{11})$, wherein
$R^8$ is the side chain of an amino acid and wherein $R^8$ can optionally be attached to $R^{10}$ to form a ring structure; or alternatively, $R^8$ is an alkyl, aryl, heteroaryl or heterocycle;
$R^9$ is hydrogen, alkyl or aryl; and
$R^{10}$ and $R^{11}$ are independently hydrogen, acyl or alkyl.

5. The compound of claim 4, wherein $R^2$ is L-valinyl.

6. The compound of claim 3, wherein $R^3$ and $R^4$ are hydrogen.

7. The compound of claim 3, wherein $R^3$ is hydrogen and $R^4$ is dimethylaminomethylene.

8. The compound of claim 3, wherein $R^3$ is hydrogen and $R^4$ is CO-alkyl.

9. The compound of claim 3, wherein $R^3$ is hydrogen and $R^4$ is CO-methyl.

10. The compound of claim 3, wherein $R^3$ is hydrogen and $R^4$ is L-valinyl.

11. A compound of the formula:

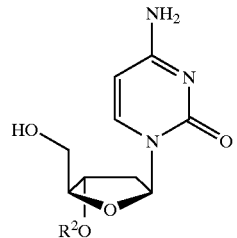

or a pharmaceutically acceptable salt thereof, wherein
$R^2$ is an amino acid residue.

12. The compound of claim 11, wherein $R^2$ is an amino acid residue of the formula $C(O)C(R^8)(R^9)(NR^{10}R^{11})$, wherein
$R^8$ the side chain of an amino acid and wherein $R^8$ can optionally be attached to $R^{10}$ to form a ring structure; or alternatively, $R^8$ an alkyl, aryl, heteroaryl or heterocycle;
$R^9$ is hydrogen, alkyl or aryl; and
$R^{10}$ and $R^{11}$ are independently hydrogen, acyl or alkyl.

13. The compound of claim 12, wherein $R^2$ is L-valinyl.

14. A pharmaceutical composition comprising an effective anti-HBV amount of a compound of the formula:

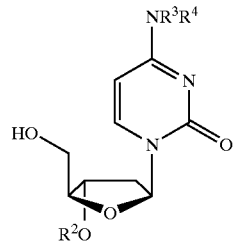

or a pharmaceutically acceptable salt thereof, wherein
$R^2$ is an amino acid residue; and
$R^3$ and $R^4$ are independently H, straight chained, branched or cyclic alkyl, dialkylaminoalkylene (in particular, dimethylaminomethylene), CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate prodrug; with a pharmaceutically acceptable carrier or diluent.

15. The pharmaceutical composition of claim 14, wherein $R^2$ is an amino acid residue of the formula $C(O)C(R^8)(R^9)(NR^{10}R^{11})$, wherein $R^8$ is the side chain of an amino acid and wherein $R^8$ can optionally be attached to $R^{10}$ to form a ring structure; or alternatively, $R^8$ is an alkyl, aryl, heteroaryl or heterocycle;

$R^9$ is hydrogen, alkyl or aryl; and $R^{10}$ and $R^{11}$ are independently hydrogen, acyl or alkyl.

16. The pharmaceutical composition of claim 15, wherein $R^2$ is L-valinyl.

17. The pharmaceutical composition of claim 14, wherein $R^3$ and $R^4$ are hydrogen.

18. The pharmaceutical composition of claim 14, wherein $R^3$ is hydrogen and $R^4$ is dimethylaminomethylene.

19. The pharmaceutical composition of claim 14, wherein $R^3$ is hydrogen and $R^4$ CO-alkyl.

20. The pharmaceutical composition of claim 14, wherein $R^3$ is hydrogen and $R^4$ is CO-methyl.

21. The pharmaceutical composition of claim 14, wherein $R^3$ is hydrogen and $R^4$ is L-valinyl.

22. A pharmaceutical composition comprising an effective anti-HBV amount of a compound of the formula:

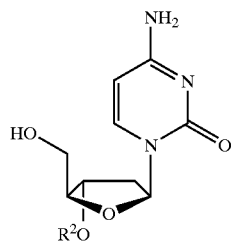

or a pharmaceutically acceptable salt thereof, wherein $R^2$ is an amino acid residue;
with a pharmaceutically acceptable carrier or diluent.

23. The pharmaceutical composition of claim 22, wherein $R^2$ is an amino acid residue of the formula $C(O)C(R^8)(R^9)(NR^{10}R^{11})$, wherein $R^8$ is the side chain of an amino acid and wherein $R^8$ can optionally be attached to $R^{10}$ to form a ring structure; or alternatively, $R^8$ is an alkyl, aryl, heteroaryl or heterocycle;

$R^9$ is hydrogen, alkyl or aryl; and $R^{10}$ $R^{11}$ are independently hydrogen, acyl or alkyl.

24. The pharmaceutical composition of claim 23, wherein $R^2$ is L-valinyl.

25. A pharmaceutical composition comprising a compound of the formula

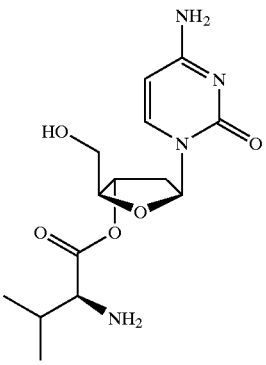

or a pharmaceutically acceptable salt thereof, with a pharmaceutically acceptable carrier or diluent.

* * * * *